US009938345B2

(12) United States Patent
Papadopoulos et al.

(10) Patent No.: US 9,938,345 B2
(45) Date of Patent: Apr. 10, 2018

(54) HUMAN ANTIBODIES TO PD-L1

(71) Applicant: Regeneron Pharmaceuticals, Inc., Tarrytown, NY (US)

(72) Inventors: Nicholas J. Papadopoulos, LaGrangeville, NY (US); Andrew J. Murphy, Croton-on-Hudson, NY (US); Gavin Thurston, Briarcliff Manor, NY (US); Ella Ioffe, Bronx, NY (US); Elena Burova, Mount Kisco, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 197 days.

(21) Appl. No.: 14/603,808

(22) Filed: Jan. 23, 2015

(65) Prior Publication Data

US 2015/0203580 A1  Jul. 23, 2015

Related U.S. Application Data

(60) Provisional application No. 61/930,582, filed on Jan. 23, 2014, provisional application No. 62/089,549, filed on Dec. 9, 2014.

(51) Int. Cl.
*C07K 16/28* (2006.01)
*A61K 39/395* (2006.01)
*A61K 45/06* (2006.01)
*C07K 16/22* (2006.01)
*C07K 16/30* (2006.01)
*A61K 39/00* (2006.01)

(52) U.S. Cl.
CPC ...... *C07K 16/2827* (2013.01); *A61K 39/3955* (2013.01); *A61K 39/39558* (2013.01); *A61K 45/06* (2013.01); *C07K 16/22* (2013.01); *C07K 16/30* (2013.01); *A61K 2039/505* (2013.01); *A61K 2039/507* (2013.01); *C07K 2317/21* (2013.01); *C07K 2317/565* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,629,204 A | 5/1997 | Honjo et al. |
| 5,698,520 A | 12/1997 | Honjo et al. |
| 6,596,541 B2 | 7/2003 | Murphy et al. |
| 6,803,792 B2 | 10/2004 | Yasuda et al. |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,087,411 B2 | 8/2006 | Daly et al. |
| 7,101,550 B2 | 9/2006 | Wood et al. |
| 7,488,802 B2 | 2/2009 | Collins |
| 7,521,051 B2 | 4/2009 | Collins et al. |
| 7,563,869 B2 | 7/2009 | Honjo et al. |
| 7,595,048 B2 | 9/2009 | Honjo et al. |
| 7,635,757 B2 | 12/2009 | Freeman et al. |
| 7,638,492 B2 | 12/2009 | Wood et al. |
| 7,709,214 B2 | 5/2010 | Freeman et al. |
| 7,722,868 B2 | 5/2010 | Freeman et al. |
| 7,794,710 B2 | 9/2010 | Chen et al. |
| 7,943,742 B2 | 5/2011 | Violette et al. |
| 7,943,743 B2 | 5/2011 | Korman et al. |
| 7,998,479 B2 | 8/2011 | Honjo et al. |
| 8,008,449 B2 | 8/2011 | Korman et al. |
| 8,088,905 B2 | 1/2012 | Collins et al. |
| 8,168,179 B2 | 5/2012 | Honjo et al. |
| 8,168,757 B2 | 5/2012 | Finnefrock et al. |
| 8,216,996 B2 | 7/2012 | Minato et al. |
| 8,217,149 B2 | 7/2012 | Irving et al. |
| 8,246,955 B2 | 8/2012 | Honjo et al. |
| 8,246,995 B2 | 8/2012 | Dai et al. |
| 8,257,740 B1 | 9/2012 | Sung et al. |
| 8,287,856 B2 | 10/2012 | Li et al. |
| 8,354,509 B2 | 1/2013 | Carven et al. |
| 8,383,796 B2 | 2/2013 | Korman et al. |
| 8,460,927 B2 | 6/2013 | Chen |
| 8,552,154 B2 | 10/2013 | Freeman et al. |
| 8,574,872 B2 | 11/2013 | Minato et al. |
| 8,580,247 B2 | 11/2013 | Li et al. |
| 8,617,546 B2 | 12/2013 | Kang et al. |
| 8,709,416 B2 | 4/2014 | Langermann et al. |
| 8,728,474 B2 | 5/2014 | Honjo et al. |
| 8,741,295 B2 | 6/2014 | Olive |
| 8,779,105 B2 | 7/2014 | Korman et al. |
| 8,779,108 B2 | 7/2014 | Queva et al. |
| 9,359,437 B2 | 6/2016 | Davis et al. |

(Continued)

FOREIGN PATENT DOCUMENTS

EP  0 670 369 A2  9/1995
EP  1 591 527 A1  11/2005

(Continued)

OTHER PUBLICATIONS

Tsai et al. (2014) Human Vaccines & Immunotherapeutics 10: 3111-3116.*

(Continued)

*Primary Examiner* — Ilia I Ouspenski
(74) *Attorney, Agent, or Firm* — Aparna G. Patankar

(57) ABSTRACT

The present invention provides antibodies that bind to the T-cell co-inhibitor ligand programmed death-ligand1 (PD-L1) protein, and methods of use. In various embodiments of the invention, the antibodies are fully human antibodies that bind to PD-L1. In certain embodiments, the present invention provides multi-specific antigen-binding molecules comprising a first binding specificity that binds to PD-L1 and a second binding specificity that binds to a tumor cell antigen, an infected cell-specific antigen, or a T-cell co-inhibitor. In some embodiments, the antibodies of the invention are useful for inhibiting or neutralizing PD-L1 activity, thus providing a means of treating a disease or disorder such as cancer or viral infection.

8 Claims, 4 Drawing Sheets

(56) References Cited

U.S. PATENT DOCUMENTS

| | | |
|---|---|---|
| 2004/0101920 A1 | 5/2004 | Radziejewski et al. |
| 2007/0280945 A1 | 12/2007 | Stevens et al. |
| 2009/0055944 A1 | 2/2009 | Korman et al. |
| 2009/0274666 A1 | 11/2009 | Chen |
| 2009/0317368 A1 | 12/2009 | Chen |
| 2010/0203056 A1 | 8/2010 | Irving et al. |
| 2010/0331527 A1 | 12/2010 | Davis et al. |
| 2011/0008369 A1 | 1/2011 | Finnefrock et al. |
| 2011/0171215 A1 | 7/2011 | Davis et al. |
| 2011/0171220 A1 | 7/2011 | Davis |
| 2011/0177088 A1 | 7/2011 | Olive et al. |
| 2011/0195454 A1 | 8/2011 | McWhirter et al. |
| 2012/0027759 A1 | 2/2012 | Chen et al. |
| 2012/0121634 A1 | 5/2012 | Chen et al. |
| 2013/0017199 A1 | 1/2013 | Langermann |
| 2013/0022595 A1 | 1/2013 | Rotem-Yehudar et al. |
| 2013/0034559 A1 | 2/2013 | Queva et al. |
| 2013/0045200 A1 | 2/2013 | Irving et al. |
| 2013/0045201 A1 | 2/2013 | Irving et al. |
| 2013/0045202 A1 | 2/2013 | Irving et al. |
| 2013/0095098 A1 | 4/2013 | Tyson |
| 2013/0108651 A1 | 5/2013 | Carven et al. |
| 2013/0109843 A1 | 5/2013 | Carven et al. |
| 2013/0122014 A1 | 5/2013 | Korman et al. |
| 2013/0164294 A1 | 6/2013 | Honjo et al. |
| 2013/0291136 A1 | 10/2013 | Freeman et al. |
| 2013/0303250 A1 | 11/2013 | Moore |
| 2014/0088295 A1 | 3/2014 | Smith et al. |
| 2014/0212422 A1 | 7/2014 | Korman et al. |
| 2014/0243504 A1 | 8/2014 | Davis et al. |
| 2014/0271684 A1 | 9/2014 | Li et al. |
| 2014/0308299 A1 | 10/2014 | Allison et al. |
| 2015/0166661 A1 | 6/2015 | Chen et al. |
| 2015/0203579 A1 | 7/2015 | Papadopoulos et al. |
| 2016/0311903 A1* | 10/2016 | West ................. A61K 49/0021 |
| 2017/0044259 A1 | 2/2017 | Tipton |
| 2017/0174779 A1 | 6/2017 | Varghese et al. |

FOREIGN PATENT DOCUMENTS

| | | |
|---|---|---|
| EP | 1 210 424 B1 | 2/2007 |
| EP | 2 161 336 A1 | 3/2010 |
| EP | 2 172 219 A1 | 4/2010 |
| EP | 2 206 517 A1 | 7/2010 |
| EP | 1 537 878 B1 | 9/2010 |
| EP | 2262837 A2 | 12/2010 |
| EP | 1 576 014 B1 | 6/2011 |
| EP | 2 418 278 A2 | 2/2012 |
| EP | 2 468 765 A1 | 6/2012 |
| EP | 2504028 A2 | 10/2012 |
| EP | 2 535 354 A1 | 12/2012 |
| EP | 1 297 135 B1 | 1/2013 |
| WO | 01/39722 A2 | 6/2001 |
| WO | 02/078731 A1 | 10/2002 |
| WO | 03/042402 A2 | 5/2003 |
| WO | 2004/056875 A1 | 7/2004 |
| WO | 2005/103081 A2 | 11/2005 |
| WO | 2006/121168 A1 | 11/2006 |
| WO | 2007/002223 A2 | 1/2007 |
| WO | 2007/005874 A2 | 1/2007 |
| WO | 2008/156712 A1 | 12/2008 |
| WO | 2009/024531 A1 | 2/2009 |
| WO | 2009/101611 A1 | 8/2009 |
| WO | 2009/114335 A2 | 9/2009 |
| WO | 2010/029434 A1 | 3/2010 |
| WO | 2010/029435 A1 | 3/2010 |
| WO | 2010/036959 A2 | 4/2010 |
| WO | 2010/077634 A1 | 7/2010 |
| WO | 2010/089411 A2 | 8/2010 |
| WO | 2011/066342 A1 | 6/2011 |
| WO | 2011/066389 A1 | 6/2011 |
| WO | 2011/110604 A1 | 9/2011 |
| WO | 2011/110621 A1 | 9/2011 |
| WO | 2012/145493 A1 | 10/2012 |
| WO | 2013/014668 A1 | 1/2013 |
| WO | 2013/019906 A1 | 2/2013 |
| WO | 2013/079174 A1 | 6/2013 |
| WO | 2013/079945 A1 | 6/2013 |
| WO | 2013/166500 A1 | 11/2013 |
| WO | 2013/169693 A1 | 11/2013 |
| WO | 2013/173223 A1 | 11/2013 |
| WO | 2013/181452 A1 | 12/2013 |
| WO | 2014/055648 A1 | 4/2014 |
| WO | 2014/066834 A1 | 5/2014 |
| WO | 2014/127917 A1 | 8/2014 |
| WO | 2014/151006 A2 | 9/2014 |
| WO | 2014/159562 A1 | 10/2014 |
| WO | 2014/179664 A1 | 11/2014 |
| WO | 2014/194293 A1 | 12/2014 |
| WO | 2014/209804 A1 | 12/2014 |
| WO | 2015/009856 A2 | 1/2015 |
| WO | 2015/016718 A1 | 2/2015 |
| WO | 2015/026634 A1 | 2/2015 |
| WO | 2015/026684 A1 | 2/2015 |
| WO | 2015/042246 A1 | 3/2015 |
| WO | 2015/048312 A1 | 4/2015 |
| WO | 2015/112800 A1 | 7/2015 |
| WO | 2015/193352 A1 | 12/2015 |

OTHER PUBLICATIONS

Momtaz et al. (2014) Pharmacogenomics and Personalized Medicine 7: 357-365.*

Powell, M. et al., "Compendium of Excipients for Parenteral Formulations" PDA Journal of Pharmaceutical & Technology, vol. 52, No. 5, pp. 238-311 (Sep.-Oct. 1998).

Powles, T. et al., "MPDL3280A (anti-PD-L1) treatment leads to clinical activity in metastatic bladder cancer," Nature, vol. 515, pp. 558-562 (Nov. 27, 2014).

Raghuraman, S. et al., "Spontaneous Clearance of Chronic Hepatitis C Virus Infection is Associated with Appearance of Neutralizing Antibodies and Reversal of T-Cell Exhaustion," The Journal of Infectious Diseases, vol. 205, pp. 763-771 (Mar. 1, 2012).

Reddy, M. et al., "Elimination of Fc Receptor-Dependent Effector Functions of a Modified IgG4 Monoclonal Antibody to Human CD4," J. Immunol, vol. 164, pp. 1925-1933 (2000).

Reineke, U., "Antibody Epitope Mapping Using Arrays of Synthetic Peptides," Methods in Molecular Biology, vol. 248: Antibody Engineering: Methods and Protocols, pp. 443-463 (2004).

Rennert, P., "Last Week's Immune Checkpoint Papers in Nature are Complicated!," SugarCone Biotech, htt://www.sugarconebotech.com/?p=814, pp. 1-4 (Dec. 4, 2014).

Ribas, A., "Tumor Immunotherapy Directed at PD-1," The New England Journal of Medicine, vol. 366, No. 26, pp. 2517-2519 (Jun. 28, 2012).

Riella, L.V. et al., "Role of the PD-1 Pathway in the Immune Response," American Journal of Transplantation, vol. 12, pp. 2575-2587 (2012).

Riley, J., "PD-1 signaling in Primary T cells," Immunol. Rev., vol. 229, No. 1, pp. 114-125 (May 2009).

Schalper, K. et al., "In situ Tumor PD-L1 mRNA expression is associated with increased TILs and better outcome in breast carcinomas," Clinical Cancer Research, Author Manuscript Published OnlineFirst on Mar. 19, 2014; DOI: 10.1158/1078-0432.CCR-13-2702.

Sheridan, C., "Cautious optimism surrounds early clinical data for PD-1 blocker," Nature Biotechnology, vol. 30, No. 8, pp. 729-730 (Aug. 2012).

Shetty, R. et al., "PD-1 blockade during chronic SIV infection reduces hyperimmune activation and microbial translocation in rhesus macaques," The Journal of Clinical Investigation, vol. 122, No. 5, pp. 1712-1716 (May 2012).

Shields, R. et al., "Lack of Fucose on Human IgG1 N-Linked Oligosaccharide Improves Binding to Human FcγRIII and Antibody-dependent Cellular Toxicity," J. Biol. Chem., vol. 277, No. 30, pp. 23733-26740 (Jul. 26, 2002).

Sznol, M. et al., "Antagonist Antibodies to PD-1 and B7-H1 (PD-L1) in the Treatment of Advanced Human Cancer," Clinical Cancer Research, vol. 19, No. 5, pp. 1021-1034 (Mar. 1, 2013).

(56) References Cited

OTHER PUBLICATIONS

Third Party Submission Under 37 CFR 1.290 Concise Description of Relevance filed in U.S. Appl. No. 14/603,776 dated Jul. 4, 2016.
Topalian S., slides presented at MMS Annual Education Program May 9-11, 2013 in Boston MA.
Topalian, S. et al., "Targeting the PD-1/B7-H1(PD-L1) pathway to activate anti-tumor immunity," Current Opinion in Immunology, vol. 24, pp. 207-212 (2012).
Tumeh, P. et al., "PD-1 blockade induces responses by inhibiting adaptive immune resistance," Nature, vol. 515, pp. 568-571 (Nov. 27, 2014).
Tutt, A. et al., "Trispecific F(ab')3 derivatives that use cooperative signaling via the TCR/CD3 complex and CD2 to activate and redirect resting cytotoxic T cells," J. Immunol, vol. 147, No. 1, pp. 60-69 (Jul. 1, 1991).
Vajdos, F. et al., "Comprehensive Functional Maps of the Antigen-binding Site of an Anti-ErbB2 Antibody Obtained with Shotgun Scanning Mutagenesis," J. Mol. Biol., vol. 320, pp. 415-428 (2002).
Wang, X.F. et al., "PD-1/PDL1 and CD28/CD80 pathways modulate natural killer T cell function to inhibit hepatitis B virus replication," Journal of Viral Hepatitis, vol. 20 (Suppl. 1), p. 27-39 (2013).
Watanabe, N. et al., "Coinhibitory Molecules in Autoimmune Diseases," Clinical and Developmental Immunology, vol. 2012, Article ID 269756, 7 pages, doi:10.1155/2012/269756.
Weber, J., "Immune Checkpoint Proteins: A New Therapeutic Paradigm for Cancer—Preclinical Background: CTLA-4 and PD-1 Blockade," Semin Oncol, vol. 37, pp. 430-439 (2010).
Wu, G. et al., "Receptor-mediated in Vitro Gene Transformation by a Soluble DNA Carrier System," J. Biol. Chem., vol. 262, No. 10, pp. 4429-4432 (Apr. 5, 1987).
Zeng, J. et al., "Anti-PD-1 Blockade and Stereotactic Radiation Produce Long-Term Survival in Mice with Intracranial Gliomas," International Journal of Radiation Oncology, vol. 86, No. 2, pp. 1-7 (2013).
Zielinski, C. et al., "Rationale for targeting the immune system through checkpoint molecule blockade in the treatment of non-small-cell lung cancer," Annals of Oncology, vol. 24, No. 5, pp. 1170-1179 (May 2013).
Zoran, G. et al. "Programmed death 1 (PD-1) lymphocytes and ligand (PD-L1) in colorectal cancer and their relationship to microsatellite instability status," J Clin Oncol. vol. 32, No. 5s (suppl; abstr 3625), 2 pages (2014).
Zou, W. et al., "Inhibitory B7-family molecules in the tumour microenvironment," Nature Reviews|Immunology, vol. 8, pp. 467-477 (Jun. 2008).
Al-Lazikani, B. et al., "Standard Conformations for the Canonical Structures of Immunoglobulins," J. Mol. Biol., vol. 273, pp. 927-948 (1997).
Altschul, S. et al., "Basic Local Alignment Search Tool," J. Mol. Biol., vol. 215, pp. 403-410 (1990).
Altschul, S. et.al., "Gapped BLAST and PSI-BLAST: a new generation of protein database search programs," Nucleic Acids Research, vol. 25, No. 17, pp. 3389-3402 (1997).
Arruebo, M. et al., "Antibody-Conjugated Nanoparticles for Biomedical Applications," Journal of Nanomaterials, vol. 2009, Article ID 439389, 24 pages, doi:10.1155/2009/439389.
Badoual, C. et al., "PD-1-Expressing Tumor-Infiltrating T Cells are a Favorable Prognostic Biomarker in HPV-Associated Head and Neck Cancer," Cancer Research, vol. 73, No. 1, pp. 128-138 (Jan. 1, 2013).
Brahmer, J. et al., "Safety and Activity of Anti-PD-L1 Antibody in Patients with Advanced Cancer," The New England Journal of Medicine, vol. 366, No. 26, pp. 2455-2465 (Jun. 28, 2012).
Brusa, D. et al., "The PD-1/PD-L1 axis contributes to T cell dysfunction in chronic lymphocytic leukemia," Haematologica 2012 [Epub ahead of print], 48 pages (2012).
Chattopadhyay, K., "Sequence, structure, function, immunity: structural genomics of costimulation," Immunol. Rev., vol. 229, No. 1, pp. 356-386 (May 2009).

Chen, D. et al,. "Molecular Pathways: Next-Generation Immunotherapy—Inhibiting Programmed Death-Ligand 1 and Programmed Death-1," Clinical Cancer Research, vol. 18, No. 24, pp. 6580-6587 (Dec. 15, 2012) published online Oct. 19, 2012.
Chen, L. et al., "Molecular mechanisms of T cell co-stimulation and co-inhibition," Nature Rev Immunol., vol. 13, pp. 227-242 (Apr. 2013).
Chen, L. et al., "Molecular mechanisms of T cell co-stimulation and co-inhibition," Nature Rev Immunol., vol. 13, pp. 227-242 (Apr. 2013) NIH Public Access Author Manuscript; available in PMC Apr. 1, 2014.
da Silva, R. "Anti-PD-1 monoclonal antibody Cancer immunotheraphy," Drugs of the future, vol. 39, No. 1, pp. 15-24 (2014).
Dong, H. et al., "B7-H1, a third member of the B7 family, co-stimulates T-cell proliferation and interleukin-10 secretion," Nature Medicine, vol. 5, No. 12, pp. 1365-1369 (Dec. 1999).
Eggermont, A. et al., "Smart therapeutic strategies in immune-oncology," Nat. Rev. Clin. Oncol., Advance Online Publication, pp. 1-2 (Mar. 4, 2014).
Ehring, H., "Hydrogen Exchange/Electrospray Ionization Mass Spectrometry Studies of Structural Features of Proteins and Protein/Protein Interactions," Analytical Biochemistry, vol. 267, pp. 252-259 (1999).
Eisenhauer, E.A. et al., "New response evaluation criteria in solid tumours: Revised RECIST guideline (version 1.1)," European Journal of Cancer, vol. 45, pp. 228-247 (2009).
Engen, J. et al., "Investigating protein structure and dynamics by hydrogen exchange MS," Analytical Chemistry, vol. 73, No. 9, pp. 256A-265A (May 1, 2001).
Fife, B. et al., "The role of the PD-1 pathway in autoimmunity and peripheral tolerance," Ann. N.Y. Acad. Sci., vol. 1217, pp. 45-59 (2011).
Flies, D. et al., "Blockade of the B7-H1/PD-1 Pathway for Cancer Immunotherapy," Yale Journal of Biology and Medicine, vol. 84, pp. 409-421 (2011).
Francisco, L. et al., "The PD-1 Pathway in Tolerance and Autoimmunity," Immunol. Rev. vol. 236, pp. 219-242 (Jul. 2010).
Freeman, G., "Structures of PD-1 with its ligands: Sideways and dancing cheek to cheek," PNAS, vol. 105, No. 30, pp. 10275-10276 (Jul. 29, 2008).
GenBank Accession No. NP_005009 Mar. 15, 2015.
GenBank Accession No. NP_005182 Mar. 15, 2015.
GenBank Accession No. NP_009192 Mar. 15, 2015.
GenBank Accession No. NP_054862 Sep. 25, 2015.
Gonnet, G. et al., "Exhaustive Matching of the Entire Protein Sequence Database," Science, vol. 256, pp. 1443-1445 (Jun. 5, 1992).
Hamid, O. et al., "Anti-programmed death-1 and anti-programmed death-ligand 1 antibodies in cancer therapy," Expert Opin. Biol. Ther. [Early Online], pp. 1-15 (Copyright 2013).
Herbst, R. et al., "Predictive correlates of response to the anti-PD-L1 antibody MPDL3280A in cancer patients," Nature, vol. 515, pp. 563-567 (Nov. 27, 2014).
Hochleitner, E.et al. "Characterization of a discontinuous epitope of the human immunodeficiency virus (HIV) core protein p24 by epitope excision and differential chemical modification followed by mass spectrometric peptide mapping analysis," Protein Science, vol. 9, pp. 487-496 (2000).
Hofmeyer, K. et al., "The PD-1/PD-L1 (B7-H1) Pathway in Chronic Infection-Induced Cytotoxic T Lymphocyte Exhaustion," Journal of Biomedicine and Biotechnology, vol. 2011, Article ID 451694, 9 pages, doi:10.1155/2011/451694 (Copyright 2011).
International Search Report and Written Opinion for Application No. PCT/US2015/012595 mailed Apr. 14, 2015.
International Search Report and Written Opinion for Application No. PCT/US2015/012589 mailed dated Jul. 10, 2015.
Junghans, R.P. et al., "Anti-Tac-H, a Humanized Antibody to the Interleukin 2 Receptor with New Features for Immunotherapy in Malignant and Immune Disorders," Cancer Research, vol. 50, pp. 1495-1502 (1990).
Kabat, "Sequences of Proteins of Immunological Interest," National Institutes of Health, vol. 1, Bethesda, Md. (1991).

(56) References Cited

OTHER PUBLICATIONS

Kasagi, S. et al., "PD-1 and Autoimmunity," Critical Reviews™ in Immunology, vol. 31, No. 4, pp. 265-295 (2011).
Kazane, S. et al., "Self-Assembled Antibody Multimers through Peptide Nucleic Acid Conjugation," J. Am. Chem. Soc., vol. 135, pp. 340-346 (2013) published Dec. 4, 2012.
Keir, M. et al., "Programmed Death-1 (PD-1):PD-Ligand 1 Interactions Inhibit TCR-Mediated Positive Selection of Thymocytes," The Journal of Immunology, vol. 175, pp. 7372-7379 (2005).
Klein, C. et al., "Progress in overcoming the chain association issue in bispecific heterodimeric IgG antibodies," mAbs, vol. 4, No. 6, pp. 653-663 (Nov./Dec. 2012).
Kufer, P. et al., "A revival of bispecific antibodies," Trends in Biotechnology, vol. 22, No. 5, pp. 238-244 (May 2004).
Langer, R., "New Methods of Drug Delivery," Science, vol. 249, pp. 1527-1533 (Sep. 28, 1990).
Lin, D. et al., "The PD-1/PD-L1 complex resembles the antigen-binding Fv domains of antibodies and T cell receptors," PNAS, vol. 105, No. 8, pp. 3011-3016 (Feb. 26, 2008).
Lipson, E. et al., "Durable Cancer Regression Off-Treatment and Effective Reinduction Therapy with an Anti-PD-1 Antibody," Clinical Cancer Research, vol. 19, No. 2, pp. 462-468 (Jan. 15, 2013).
Martin, A. et al., "Modeling antibody hypervariable loops: A combined algorithm," Proc. Natl. Acad. Sci. USA, vol. 86, pp. 9268-9272 (Dec. 1989).
Nishino, M. et al., "Developing a Common Language for Tumor Response to Immunotherapy: Immune-Related Response Criteria Using Unidimensional Measurements," Clinical Cancer Research, vol. 19, No. 14, pp. 3936—(Jul. 15, 2013).
Padlan, E. et al., "Identification of specificity-determining residues in antibodies," FASEB J, vol. 9, pp. 133-139 (Jan. 1995).
Pardoll, D., "The blockade of immune checkpoints in cancer immunotherapy," Nature Reviews|Cancer, vol. 12, pp. 252-264 (Apr. 2012).
Pearson, W., "Chapter 26. Using the FASTA Program to Search Protein and DNA Sequence Databases," Methods in Molecular Biology, vol. 24: Computer Analysis of Sequence Data, Part 1, pp. 307-331 (1994).
Peggs, K. et al., "PD-1 blockade: promoting endogenous anti-tumor immunity," Expert Rev. Anticancer Ther., vol. 12, No. 10, pp. 1279-1282 (2012).
Peng, W., "PD-1 Blockade Enhances T-cell Migration to Tumors by Elevating IFN-γ Inducible Chemokines," Cancer Res., vol. 72, No. 20, pp. 5209-5218 (Published OnlineFirst Aug. 20, 2012).
Postow, M. et al., "Targeting Immune Checkpoints: Releasing the Restraints on Anti-tumor Immunity for Patients with Melanoma," Cancer J., vol. 18, No. 2, pp. 153-159 (2012).
U.S. Appl. No. 15/593,897, filed May 12, 2017.
U.S. Appl. No. 15/593,915, filed May 12, 2017.
International Search Report and Written Opinion for PCT/US20161068030 (dated May 26, 2017).
"Study of REGN2810 and REGN1979 in Patients with Lymphoma or Acute Lymphoblastic Leukemia," retrieved from the internet: https://apifiveclinicaltrials.com/trialpage?dcn=10963&city=Baltimore&country=UnitedStates&start=20&state=Maryland&conditions=lymphoma&id= 207048402254, 1 page (last updated Nov. 16, 2016).
"A Phase 1 Study to Access Safety and Tolerability of REGN1979, an anti-CD20 x anti-CD3 bispecific monoclonal antibody, and REGN2810, an anti-programmed death-1 (PD-1) monoclonal antibody", EU Clinical Trials Register, https://www.clinicaltrialsregister.eu/ctr-search/search?query=2015-001697-17, 3 pages (Start Date: Dec. 1, 2015).
"Clinical Trials Register: A Phase 1 Study to Access Safety and Tolerability of REGN1979, an anti-CD20 x anti-CD3 bispecific monoclonal antibody, and REGN2810, an anti-programmed death-1 (PD-1) monoclonal antibody, in Patients with B-cell Malignancies", EU Clinical Trials Register, https://www.clinicaltrialsregister.eu/ctr-search/trial/2015-001697-17/ES, 8 pages (Oct. 15, 2015).
"Study of REGN2810 and REGN1979 in Patients with Lymphoma or Acute Lymphoblastic Leukemia", Smart Patients, https://www.smartpatients.com/trials/NCT02651662, 3 pages (Start Date: Nov. 2015).
Feuchtinger et al., "Leukemia Related Co-Stimulation/Co-Inhibition Predict T-Cell Attack of Acute Lymphoblastic Leukemia Mediated by Blinatumomab," Blood, 126:3764 (2015) (Abstract).
Opposition for Colombian Patent Application No. NC2016/0000106 (dated May 5, 2017).
Topalian et al., Safety, activity, and immune correlates of anti-PD-1 antibody in cancer, The New England Journal of medicine: 366, 26: 2443-2454 (2012).
Anonymous, Safety, activity, and immune correlates of anti-PD-1 antibody in cancer, https://clinicaltrials.gov/archive/NCT02383212/2016_05_02 (2016).
Ahmed et al., Clinical outcomes of melanoma brain metastases treated with stereotactic radiation and anti-PD-1 therapy, Annals of Oncology 27, 3: 434-441 (2015).
Mohiuddin et al., High-Dose Radiation as a Dramatic, Immunological Primer in Locally Advanced Melanoma, CUREUS (2015).
Park et al., PD-1 Restrains Radiotherapy-Induced Abscopal Effect, Cancer Immunology Research, 3, 6: 610-619 (2015).
Liniker et al., Safety and Activity of Combined Radiation Therapy (RT) and Anti-PD-1 Antibodies (PD-1) in Patients (pts) With Metastatic Melanoma, International Journal of Radiation: Oncology Biology Phsics, 93, 3: E635 (2015).
Ramesh Rengan et al., Radiation Therapy Contraindications and Safety Panel: Re-irradiation, Novel Combination Therapies, and Hypofractionation, https://www.astro.org/uploadedFiles/_MAIN_SITE_Meeting_and_Education/Events_(ASTRO)/2016/Sample_ASTRO_Meeting/Content_Pieces/RTPaneCombined.pdf: 31-32 (2016).
International Search Report for PCT/US2017/032397, dated Jul. 11, 2017.
International Search Report for PCT/US2017/032408, dated Jul. 6, 2017.
Anonymous, NCT02760498: A Ogase 2 Study of REGN2810, a Fully Human Monoclonal Antibody to Programmed Death-1 (PD-1), in Patients With Advanced Cutaneous Squamous Cell Carcinoma, ClinicalTrials.gov rchive, https://clinicaltrials.gov/archive/NCT02760498/2016_05_02 (2016).
Mahoney et al, The Next Immune-Checkpoint Inhibitors: PD-1/PD-L1 Blockade in Melanoma, Clinical Therapeutics, 37, 4: 764-782 (2015).
ESMO 2014: Results of a Phase III Randomised Study of Nivolumab in Patients with Advanced Melanoma After Prior Anti-CTLA4 Therapy, European Society for Medical Oncology (2014).
Demaria et al., "Ionizing Radiation Inhibition of Distant Untreated Tumors (Abscopal Effect) is Immune Mediated," Int. J. Radiation Oncology Biol. Phys., 58(3):862-870 (2004).
Demaria et al "Immune-Mediated Inhibition of Metastases after Treatment with Local Radiation and CTLA-4 Blockade in a Mouse Model of Breast Cancer," Clinical Cancer Research, 11:728-734 (2005).
Lugade et al., "Local Radiation Therapy of B16 Melanoma Tumors Increases the Generation of Tumor Antigen-Specific Effector Cells That Traffic to the Tumor," J. Immunol, 174:7516-7523 (2005).
Dewan et al., "Fractionated but Not Single-Dose Radiotherapy Induces an Immune-Mediated Abscopal Effect when Combined with Anti-CTLA-4 Antibody," Clin. Cancer Res., 15(17):5379-5388 (2009).
Kachikwu et al., "Radiation Enhances Regulatory T Cell Representation," Int. J. Radiation Oncology Biol. Phys., 81 (4):1128-1135 (2011).
Postow et al., "Immunologic Correlates of the Abscopal Effect in a Patient with Melanoma," The New England Journal of Medicine, 366:925-931 (2012).
Kalbasi, "Radiation and immunotherapy: a synergistic combination," The Journal of Clinical Investigation, 123 (7):2756-2763 (2013).
Deng et al., "Irradiation and anti-PD-L1 treatment synergistically promote antitumor immunity in mice," The Journal of Clinical Investigation, 124(2):687-695 (2014).

(56) References Cited

OTHER PUBLICATIONS

Sharabi et al., "Stereotactic Radiation Therapy Augments Antigen-Specific PD-1 Mediated Anti-Tumor Immune Responses via Cross-Presentation of Tumor Antigen," Cancer Immunol Res, 3:345-355 (2014).
Crittenden et al., "Current Clinical Trials Testing Combinations of Immunotherapy and Radiation," Seminars in Radiation Oncology, 25:54-64 (2015).
Park et al., "PD-1 Restrains Radiotherapy-Induced Abscopal Effect", Cancer Immunol Res, 3(6):610-619 (2015).
Victor et al., "Radiation and dual checkpoint blockade activate non-redundant immune mechanisms in cancer," Nature, 520(7547):373-377 (2015).
Golden et al., "Local radiotherapy and granulocyte-macrophage colony-stimulating factor to generate abscopal responses in patients with metastatic solid tumours: a proof-of-principle trial", Lancet Oncol., 16:795-803 (2015).
Schoenhals et al., "Preclinical Rationale and Clinical Considerations for Radiotherapy Plus Immunotherapy: Going Beyond Local Control", The Cancer Journal, 22:130-137 (2016).
Bernstein et al., "Immunotherapy and stereotactic ablative radiotherapy (ISABR): a curative approach?", Nature Reviews, Clinical Oncology, 3:516-524 (2016).
Rodriguez-Ruiz et al., "Abscopal Effects of Radiotherapy Are Enhanced by Combined Immunostimulatory mAbs and Are Dependent on CD8 T Cells and Crosspriming", Cancer Res., 76:5994-6005 (2016).
Wang et al., "Suppression of type I IFN signaling in tumors mediates resistance to anti-PD-1 treatment that can be overcome by radiotherapy", Cancer Res., 77(4):839-850 (2016).
Vanpouille-Box, "Towards precision radiotherapy for use with immune checkpoint blockers", Clin. Cancer Res., clincanres.0037.2017 (2017).
Weichselbaum et al., "Radiotherapy and immunotherapy: a beneficial liaison?", Nat Rev Clin Oncol, 14(6):365-379 (2017).
Pearson, "Flexible Sequence Similarity Searching with the FASTA3 Program Package," Methods Mol Biol, 132:185-219 (2000).
Shields et al., "Lack of Fucose on Human IgG1 N-Linked Oligosaccharide Improves Binding to Human FcγRlll and Antibody-dependent Cellular Toxicity," J. Biol. Chem., 277(30):26733-26740 (Jul. 26, 2002).
Borradori et al., "Rescue therapy with anti-programmed cell death protein 1 inhibitors (PD-1) of advanced cutaneous squamous cell carcinoma and basosquamous carcinoma: preliminary experience in 5 cases," Br J Dermatol., 175(6):1382-1386 (2016).
Chang et al., "A Case Report of Unresectable Cutaneous Squamous Cell Carcinoma Responsive to Pembrolizumab, a Programmed Cell Death Protein 1 Inhibitor," JAMA Dermatology, Letters: E1-E3 (2015).
Crammer et al., "Treatment of Unresectable and Metastatic Cutaneous Squamous Cell Carcinoma," The Oncologist 15:1320-1328 (2010).
Jegache et al., "Major response to pembrolizumab in two patients with locally advanced cutaneous squamous cell carcinoma," JEADV, Letter to the Editor: 1-2 (2017).

Falchook et al., "Responses of metastatic basal cell and cutaneous squamous cell carcinomas to anti-PD1 monoclonal antibody REGN2810," J Immunother Cancer, 4(70):1-5 (2016).
Papadopoulos et al. "REGN2810, A Human Anti-PD-1 Monoclonal Antibody, for Patients with Unresectable Locally Advanced or Metastatic Cutaneous Squamous Cell Carcinoma (CSCC): Initial Safety and Efficacy," ASCO Annual Meeting (2017).
Fisher et al., "Suppressor T Lymphocytes Control the Development of Primary Skin Cancers in Ultraviolet-Irradiated Mice," Science, 216(4):1133-1134 (1982).
Freeman et al., "Comparative Immune Phenotypic Analysis of Cutaneous Squamous Cell Carcinoma and Intraepidermal Carcinoma in Immune-Competent Individuals: Proportional Representation of CD8+ T-Cells but Not FoxP3+ Regulatory T-Cells Is Associated with Disease Stage," PLOS ONE 9(10), e110928:1-9 (2014).
Mavropoulos et al., "Prospects for personalized targeted therapies for cutaneous squamous cell carcinoma," Seminars in Cutaneous Medicine and Surgery, 33:72-75 (2014).
Mühleisen et al., "Progression of cutaneous squamous cell carcinoma in immunosuppressed patients is associated with reduced CD123+ and FOXP3+ cells in the perineoplastic inflammatory infiltrate," Histopathology, 55:67-76 (2009).
Pickering et al., "Mutational landscape of aggressive cutaneous squamous cell carcinoma," Clin Cancer Res., 20 (24):6582-6592 (2014).
Schaper et al., "The Pattern and Clinicopathological Correlates of PD-L1 Expression in Cutaneous Squamous Cell carcinoma," Running head: PD-L1 expression in cutaneous squamous cell carcinoma, Research Letter (2016).
Slater et al., "PD-L1 expression in cutaneous squamous cell carcinoma correlates with risk of metastasis," Knoxville Dermatopathology Laboratory, J Cutan Path, 43(8):663-70 (2016).
Soura et al., "Programmed cell death protein-1 inhibitors for immunotherapy of advanced nonmelanoma skin cancer: showing early promise," British Journal of Dermatology 175(6):1150-1151 (2016).
Stevenson et al., "Expression of Programmed Cell Death Ligand in Cutaneous Squamous Cell Carcinoma and Treatment of Locally Advanced Disease With Pembrolizumab," JAMA Dermatol., 153(4):299-303 (2017).
Tran et al., "Follow-up on Programmed Cell Death 1 Inhibitor for Cutaneous Squamous Cell Carcinoma," JAMA Dermatology, Letters: E1-E3 (2016).
Anonymous, "Clinical Trails Register: A Phase I Study to Assess Safety and Tolerability of REGN1979, an anti-CD20 x anti-CD3 bispecific monoclonal antibody, and REGN2810, and anti-programmed death-1 (PD-1) monoclonal antibody, in Patients with B-cell Malignancies," p. 1, section A.3; p. 3, section E.1 [Retrieved from the Internet Mar. 14, 2017: <URL: https://www.clinicaltrialsregister.eu/ctr-search/trial/2015-001697-17/ES>].
Anonymous, "Study of REGN2810 and REGN1979 in Patientcs with Lymphoma or Acute Lymphoblastic Leukemia." [Retrieved from the Internet Mar. 15, 2017: <URL: https://www.api.liveclinicaltrials.com/trialpage?dcn=10963&city=Baltimore&country=UnitedStates&start=20&state=Maryland&conditions=lymphoma&id=207048402254>].

\* cited by examiner

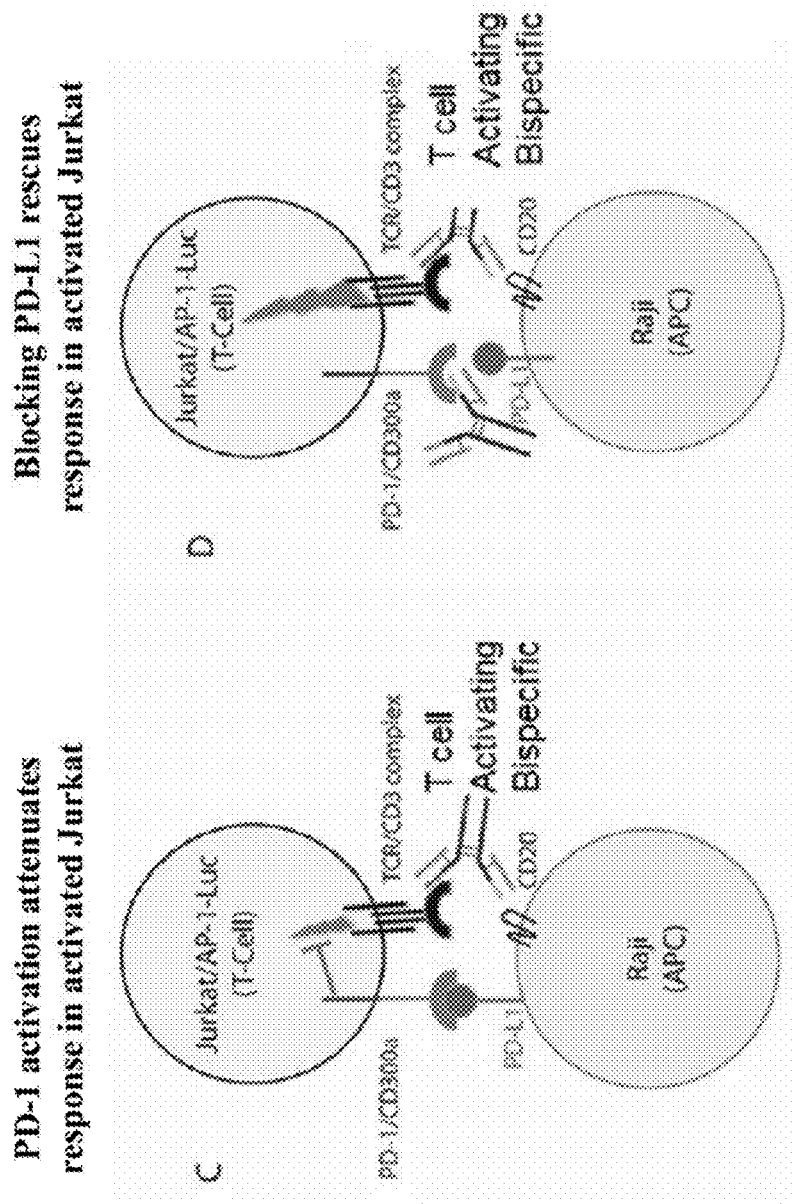
Figure 1 (Contd.)

HUMAN ANTIBODIES TO PD-L1

CROSS-REFERENCE TO RELATED APPLICATIONS

This application claims the benefit under 35 U.S.C. § 119(e) of US provisional application Nos. 61/930,582, filed on Jan. 23, 2014; and 62/089,549, filed on Dec. 9, 2014, the disclosures of each herein incorporated by reference in their entireties.

FIELD OF THE INVENTION

The present invention is related to human antibodies and antigen-binding fragments of human antibodies that specifically bind to the immunomodulatory receptor ligand programmed death-ligand 1 (PD-L1), and therapeutic and diagnostic methods of using those antibodies.

STATEMENT OF RELATED ART

Programmed death-ligand 1 (PD-L1) (also called B7-H1 or CD274) is a 290 amino acid protein receptor ligand expressed widely on both lymphoid and non-lymphoid tissues such as CD4 and CD8 T-cells, macrophage lineage cells, peripheral tissues as well as on tumor cells, and virally-infected cells (Dong et al 1999, Nature Med.). PD-L1 binds to receptors PD-1 and B7-1 which belong to the CD28/CTLA-4 (cytotoxic T lymphocyte antigen)/ICOS (inducible co-stimulator) family of T-cell co-inhibitory receptors (Chen et al 2013, Nature Rev. Immunol. 13: 227-242) and attenuates the immune response by inhibiting T-cell activation. PD-L1 binding to PD-1 or B7-1 results in decreased T-cell proliferation and cytokine secretion, compromising humoral and cellular immune responses in diseases such as cancer, and viral infection.

The expression of PD-L1 on tumor cells and virally-infected cells is exploited by tumors and chronic viral infections to evade immune response. PD-L1 is expressed on a wide variety of tumors and studies on animal models have shown that PD-L1 on tumors inhibits T-cell activation and lysis of tumor cells and may lead to increased death of tumor-specific T-cells. In chronic viral infections, PD-L1 expressed on virally-infected cells binds to PD-1 on virus-specific T-cells and these T-cells become "exhausted" with loss of effector functions and proliferative capacity (Freeman 2008, PNAS 105: 10275-10276). The PD-1: PD-L1 system also plays an important role in induced T-regulatory (Treg) cell development and in sustaining Treg function (Francisco et al 2010, Immunol. Rev. 236: 219-242).

Since PD-L1 plays an important role in tumor immunity and infectious immunity, it is an ideal target for immunotherapy. Blocking PD-L1 with antagonists, including monoclonal antibodies, has been studied in treatments of cancer and chronic viral infections (Ribas 2012, NEJM 366: 2517-2519; Freeman 2008, PNAS 105: 10275-10276; Sheridan 2012, Nature Biotechnology 30: 729-730).

Monoclonal antibodies to PD-L1 are known in the art and have been described, for example, in U.S. Pat. Nos. 7,943, 742, 8,383,796, 8,217,149, Publication Nos. 20090055944, 20120003056, 20130034559, 20130045200, 20130045201, 20130045202, and in WO2007005874, WO2011066389, WO2010077634, EP1907424, and EP1899379.

BRIEF SUMMARY OF THE INVENTION

The present invention provides antibodies and antigen-binding fragments thereof that bind PD-L1. The antibodies of the present invention are useful, inter alia, for targeting cells expressing PD-L1 such as cancer cells or virally-infected cells, and for modulating PD-L1 activity. In certain embodiments, the antibodies of the invention are useful for inhibiting or neutralizing PD-L1 activity and for stimulating T cell activation, e.g., under circumstances where T cell-mediated killing is beneficial or desirable. The anti-PD-L1 antibodies of the invention, or antigen-binding portions thereof, may be included as part of a multi-specific antigen-binding molecule, for example, to modulate the immune response and/or to target the antibodies to a specific cell type, such as a tumor cell, or a virally infected cell. The antibodies are useful in treating a disease or disorder such as cancer and viral infection.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933). In certain embodiments, the antibodies may be bispecific.

In a first aspect, the present invention provides isolated monoclonal antibodies or antigen-binding fragments thereof that bind specifically to PD-L1. Exemplary anti-PD-L1 antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-PD-L1 antibodies. Table 2 sets forth the nucleic acid sequence identifiers of the HCVRs, LCVRs, HCDR1, HCDR2 HCDR3, LCDR1, LCDR2 and LCDR3 of the exemplary anti-PD-L1 antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-PD-L1 antibodies listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/170, 186/194, 202/210, 218/226, 234/242, 250/258, 266/274, 282/274, 290/274, 298/274, 306/274, 314/274, 322/274, 330/274, and 338/274. In certain embodiments, the HCVR/LCVR amino acid sequence pair is selected from one of SEQ ID NOs: 82/90 (e.g., H2M8314N), 162/170 (e.g., H2M8718N), 306/274 (e.g., H1H9364P2), and 314/274 (e.g., H1H9373P2). In certain other embodiments, the HCVR/LCVR amino acid sequence pair is selected from one of SEQ ID NOs: 98/106 (e.g., H2M8316N), 146/154 (e.g., H2M8323N), 290/274 (e.g., H1H9351P2), and 330/274 (e.g., H1H9387P2).

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-PD-L1 antibodies listed in Table 1. In certain embodiments, the HCDR3/LCDR3 amino acid sequence pair is selected from the group consisting of SEQ ID NOs: 88/96 (e.g., H2M8314N), 168/176 (e.g., H2M8718N), 312/280 (e.g., H1H9364P2), and 320/280 (e.g., H1H9373P2). In certain other embodiments, the HCDR3/LCDR3 amino acid sequence pair is selected from the group consisting of SEQ ID NOs: 104/112 (e.g., H2M8316N), 152/160 (e.g., H2M8323N), 296/280 (e.g., H1H9351P2), and 336/280 (e.g., H1H9387P2).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-PD-L1 antibodies listed in Table 1. In certain embodiments, the HCDR1-HCDR2-HCDR3-LCDR1-LCDR2-LCDR3 amino acid sequence set is selected from the group consisting of SEQ ID NOs: 84-86-88-92-94-96 (e.g., H2M8314N); 164-166-168-172-174-176 (e.g., H2M8718N); 308-310-312-276-278-280 (e.g., H1H9364P2); and 316-318-320-276-278-280 (e.g., H1H9373P2). In certain other embodiments, the HCDR1-HCDR2-HCDR3-LCDR1-LCDR2-LCDR3 amino acid sequence set is selected from the group consisting of SEQ ID NOs: 100-102-104-108-110-112 (e.g., H2M8316N); 148-150-152-156-158-160 (e.g., H2M8323N); 292-294-296-276-278-280 (e.g., H1H9351P2); and 332-334-336-276-278-280 (e.g., H1H9387P2).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-PD-L1 antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 82/90 (e.g., H2M8314N), 98/106 (e.g., H2M8316N), 146/154 (e.g., H2M8323N), 162/170 (e.g., H2M8718N), 290/274 (e.g., H1H9351P2), 306/274 (e.g., H1H9364P2), 314/274 (e.g., H1H9373P2) and 330/274 (e.g., H1H9387P2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention includes anti-PD-L1 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

The present invention also provides for antibodies and antigen-binding fragments thereof that compete for specific binding to PD-L1 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides isolated antibodies and antigen-binding fragments thereof that block PD-L1 binding to PD-1 or to B7-1. In some embodiments, the antibody or antigen-binding fragment thereof that blocks PD-L1 binding to PD-1 or to B7-1 may bind to the same epitope on PD-L1 as PD-1/B7-1 or may bind to a different epitope on PD-L1 as PD-1/B7-1. In certain embodiments, the antibodies of the invention that block PD-L1 binding to PD-1 or to B7-1 comprise the CDRs of an HCVR having an amino acid sequence selected from the group consisting of HCVR sequences listed in Table 1; and the CDRs of a LCVR having an amino acid sequence selected from the group consisting of LCVR sequences listed in Table 1.

In alternate embodiments, the present invention provides antibodies and antigen-binding fragments thereof that do not block PD-L1 binding to PD-1 or to B7-1. In certain embodiments, the present invention provides isolated antibodies or antigen-binding fragments thereof that bind PD-L1, wherein the antibodies or antigen-binding fragments thereof enhance PD-L1 binding to PD-1 or to B7-1. In some embodiments, the isolated antibodies or antigen-binding fragments thereof that enhance PD-L1 binding to PD-1/B7-1 comprise the CDRs of a HCVR, wherein the HCVR has an amino acid sequence selected from the group consisting of SEQ ID NOs: 18, 66, 114, 130, 202, 218, 266, 282, 298, 322 and 338; and the CDRs of a LCVR, wherein the LCVR has an amino acid sequence selected from the group consisting of SEQ ID NOs: 26, 74, 122, 138, 210, 226, and 274. In some embodiments, the isolated antibodies or antigen-binding fragments thereof comprise an HCVR/LCVR amino acid sequence pair selected from the group consisting of SEQ ID NOs: 18/26 (e.g., H2M8307N), 66/74 (e.g., H2M8312N), 114/122 (e.g., H2M8317N), 130/138 (e.g., H2M8321N), 202/210 (e.g., H1H9323P), 218/226 (e.g., H1H9327P), 266/274 (e.g., H1H9344P2), 282/274 (e.g., H1H9345P2), 298/274 (e.g., H1H9354P2), 322/274 (e.g., H1H9382P2), and 338/274 (e.g., H1H9396P2).

The present invention also provides antibodies and antigen-binding fragments thereof that bind specifically to PD-L1 from human or other species. In certain embodiments, the antibodies may bind to human PD-L1 and/or to cynomolgus PD-L1.

The present invention also provides antibodies and antigen-binding fragments thereof that cross-compete for binding to PD-L1 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In one embodiment, the invention provides an isolated antibody or antigen-binding fragment that has one or more of the following characteristics: (a) blocks the binding of PD-L1 to PD-1 or to B7-1; (b) binds specifically to human PD-L1 and/or cynomolgus PD-L1; (c) inhibits T-cell proliferation in a mixed lymphocyte reaction (MLR) assay; and (d) increases IL-2 and/or interferon-gamma secretion in a MLR assay.

In some embodiments, the antibody or antigen binding fragment thereof may bind specifically to PD-L1 in an agonist manner, i.e., it may enhance or stimulate PD-L1 binding and/or activity; in other embodiments, the antibody may bind specifically to PD-L1 in an antagonist manner, i.e., it may block PD-L1 from binding to its receptor.

In certain embodiments, the antibodies or antigen-binding fragments of the present invention are bispecific comprising a first binding specificity to PD-L1 and a second binding specificity for a second target epitope. The second target epitope may be another epitope on PD-L1 or on a different protein such as a T-cell co-inhibitor. In certain embodiments, the target epitope may be on a different cell including e.g., a different T-cell, a B-cell, a tumor cell, an autoimmune tissue cell or a virally infected cell.

In a second aspect, the present invention provides nucleic acid molecules encoding anti-PD-L1 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-PD-L1 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-PD-L1 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-PD-L1 antibody listed in Table 1.

In a related aspect, the present invention provides recombinant expression vectors capable of expressing a polypeptide comprising a heavy or light chain variable region of an anti-PD-L1 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, the present invention provides multi-specific antigen-binding molecules and antigen-binding fragments thereof comprising a first antigen-binding specificity that binds specifically to PD-L1 and a second antigen-binding specificity that binds specifically to an antigen selected from the group consisting of PD-L1, a tumor cell-specific antigen, an infected-cell-specific antigen, and a T-cell co-inhibitor. In certain embodiments, the first antigen-binding specificity may comprise three CDRs derived from a HCVR with an amino acid sequence selected from the HCVR sequences in Table 1 and three CDRs derived from a LCVR with an amino acid sequence selected from the LCVR sequences in Table 1. In one embodiment, the first antigen-binding specificity may comprise an extracellular domain of PD-1 or of B7-1, or a fragment thereof. The second antigen-binding specificity may target an antigen on the same cell as PD-L1 or on a different cell of the same tissue type or of a different tissue type. For example, the multi-specific antigen-binding molecule may bind to a T-cell wherein the first antigen-binding specificity may bind specifically to PD-L1 and the second antigen-binding specificity may bind to a T-cell co-inhibitor on the T-cell. Alternatively, in another embodiment, the first antigen-binding specificity binds specifically to PD-L1 on a T-cell and the second antigen-binding specificity is targeted to an antigen/receptor on a B-cell or a macrophage or antigen-presenting cell. In certain embodiments, the second antigen-binding specificity is directed to an antigen on a tumor cell, or on a cell infected with a virus. In one embodiment, the first antigen-binding specificity comprises an extracellular domain of PD-1 and the second antigen-binding specificity binds to a different epitope on PD-L1. In certain embodiments, the first antigen-binding specificity binds to PD-L1 with a lower affinity, for example, with a $K_D$ more than $10^{-8}$ M, more than $10^{-7}$ M, more than $10^{-6}$ M, or more than $10^{-5}$ M.

In a fourth aspect, the invention provides a pharmaceutical composition comprising a recombinant human antibody or antigen-binding fragment thereof which specifically binds PD-L1 and a pharmaceutically acceptable carrier. In a related aspect, the invention features a composition which is a combination of an anti-PD-L1 antibody and a second therapeutic agent. In one embodiment, the second therapeutic agent is any agent that is advantageously combined with an anti-PD-L1 antibody. Exemplary agents that may be advantageously combined with an anti-PD-L1 antibody include, without limitation, other agents that bind and/or modulate PD-L1 signaling (including other antibodies or antigen-binding fragments thereof, etc.) and/or agents which do not directly bind PD-L1 but nonetheless modulate immune cell activation. Additional combination therapies and co-formulations involving the anti-PD-L1 antibodies and multi-specific antigen-binding molecules of the present invention are disclosed elsewhere herein.

In a fifth aspect, the invention provides methods to modulate the immune response in a subject, the method comprising administering a therapeutically effective amount of an anti-PD-L1 antibody or antigen-binding fragment thereof of the invention to the subject in need thereof. In certain embodiments, the invention provides methods to enhance the immune response in a subject, the methods comprising administering to the subject an effective amount of an antibody or fragment thereof of the invention that binds PD-L1 and blocks PD-L1 binding to PD-1 or to B7-1. In one embodiment, the invention provides a method to stimulate or enhance T-cell activation in a subject, the method comprising administering a blocking antibody or antigen-binding fragment thereof of the invention to the subject in need thereof. In one embodiment, the invention provides methods to inhibit a T-regulatory (Treg) cell in a subject, the methods comprising administering a blocking antibody or antigen-binding fragment thereof of the invention to the subject in need thereof. In certain embodiments, the subject in need thereof may suffer from a disease or disorder such as cancer or viral infection. In alternate embodiments, the present invention provides methods to inhibit T-cell activation, the methods comprising administering an activating antibody or antigen-binding fragment thereof of the invention to a subject in need thereof. In certain further embodiments, the subject in need thereof may suffer from an autoimmune disease.

In a sixth aspect, the invention provides therapeutic methods for treating a disease or disorder, for example, cancer or viral infection, in a subject using an anti-PD-L1 antibody or antigen-binding portion of an antibody of the invention, wherein the therapeutic methods comprise administering a therapeutically effective amount of a pharmaceutical composition comprising an antibody or fragment of an antibody of the invention to the subject in need thereof. The disorder treated is any disease or condition which is improved, ameliorated, inhibited or prevented by stimulation or inhibition of PD-L1 binding or activity. In certain embodiments, the antibody or antigen-binding fragment thereof the invention is administered in combination with a second therapeutic agent to the subject in need thereof. The second therapeutic agent may be selected from the group consisting of an antibody to a T-cell co-inhibitor, an antibody to a tumor cell antigen, an antibody to a T-cell receptor, an antibody to a Fc receptor, an antibody to an epitope on a virally infected cell, an antibody to PD-1, a cytotoxic agent, an anti-cancer drug, an anti-viral drug, an anti-inflammatory drug (e.g., corticosteroids), a VEGF antagonist, and any other drug or therapy known in the art. In certain embodiments, the second therapeutic agent may be an agent that helps to counteract or reduce any possible side effect(s) associated with an antibody or antigen-binding fragment thereof of the invention, if such side effect(s) should occur.

In certain embodiments, the present invention provides methods for suppressing tumor growth. In certain embodiments, the present invention provides methods to enhance survival of cancer patients. Examples of cancer include, but are not limited to, primary and/or recurrent cancer, including brain cancer (e.g., glioblastoma multiforme), lung cancer (e.g., non-small cell lung cancer), squamous cell carcinoma of head and neck, renal cell carcinoma, melanoma, multiple myeloma, prostate cancer, and colon cancer. The methods comprise administering a pharmaceutical composition comprising a therapeutically effective amount of an anti-PD-L1 antibody of the present invention in combination with a second therapeutic agent selected from the group consisting of a vascular endothelial growth factor (VEGF) antagonist (e.g., aflibercept, bevacizumab), an angiopoietin-2 (Ang2) inhibitor (e.g., an anti-Ang2 antibody such as nesvacumab), a lymphocyte activation gene 3 (LAG-3) inhibitor, a cytotoxic T-lymphocyte antigen 4 (CTLA-4) inhibitor (e.g., ipilimumab), a CCR4 inhibitor (e.g., mogamulizumab), a chemotherapeutic agent, and radiation therapy. Additional examples of additional therapies/therapeutic agents that can be used in combination with an anti-PD-L1 antibody of the invention for use in treating cancer are described elsewhere herein.

The antibody or fragment thereof may be administered subcutaneously, intravenously, intradermally, intraperitoneally, orally, intramuscularly, or intracranially. The antibody or fragment thereof may be administered at a dose of about 0.1 mg/kg of body weight to about 100 mg/kg of body weight of the subject.

The present invention also includes use of an anti-PD-L1 antibody or antigen-binding fragment thereof of the invention in the manufacture of a medicament for the treatment of a disease or disorder (e.g., cancer, and chronic viral infection) that would benefit from the blockade or enhancement of PD-L1 binding and/or signaling.

Other embodiments will become apparent from a review of the ensuing detailed description.

DETAILED DESCRIPTION

Figure 1:
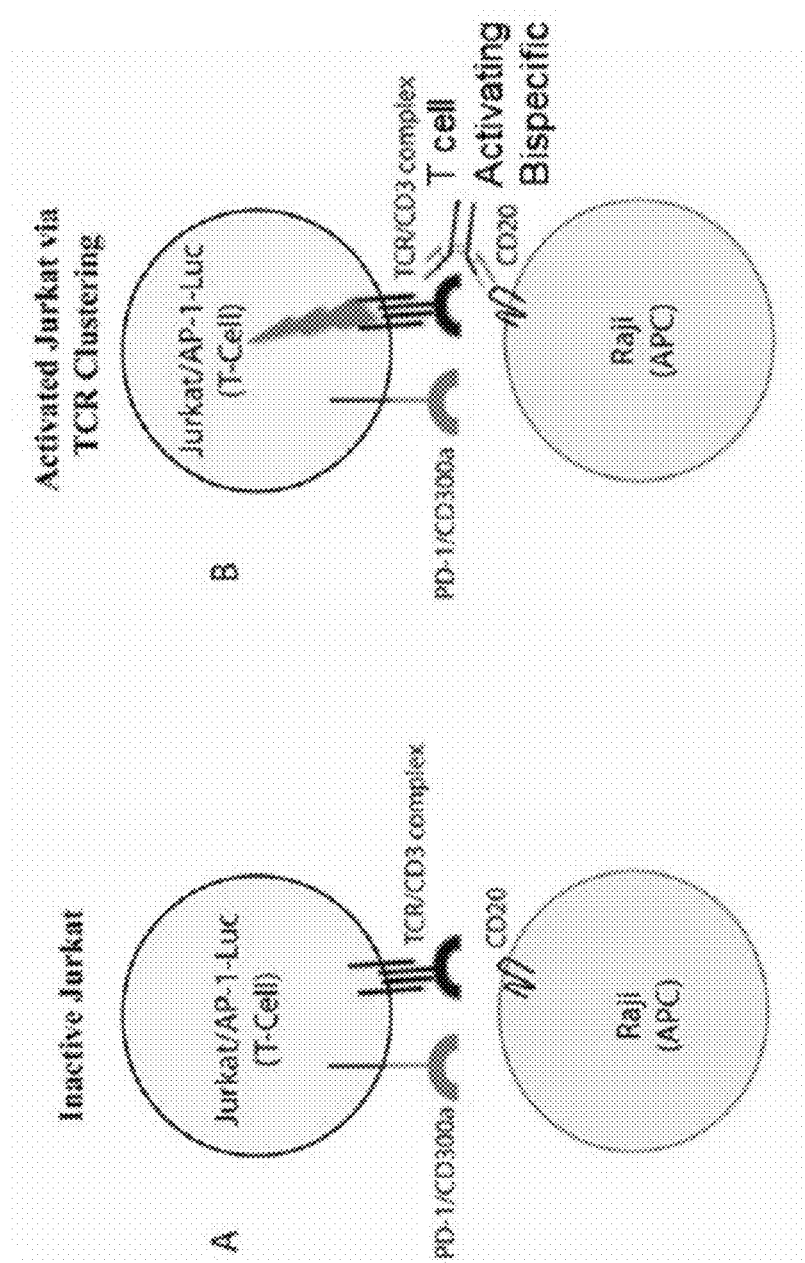
FIG. 1 is a schematic of the luciferase-based PD-L1 bioassay described in Example 8 herein. Panel A: Inactive Jurkat cells; Panel B: Jurkat cells are activated by T-cell receptor (TCR) clustering through the CD3xCD20 bispecific antibody; Panel C: PD-1 activation attenuates response in activated Jurkat cells; Panel D: Blocking PD-L1 rescues the response in activated Jurkat cells.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

The term "PD-L1" refers to programmed death-ligand 1, also known as CD274 and B7H1. The amino acid sequence of full-length PD-L1 is provided in GenBank as accession number NP_054862.1 and is also referred to herein as SEQ ID NO: 351. The term "PD-L1" also includes protein variants of PD-L1 having the amino acid sequence of SEQ ID NOs: 345, 346, 347 or 348. The term "PD-L1" includes recombinant PD-L1 or a fragment thereof. The term also encompasses PD-L1 or a fragment thereof coupled to, for example, histidine tag, mouse or human Fc, or a signal sequence such as ROR1. For example, the term includes sequences exemplified by SEQ ID NOs: 347 or 348, comprising a mouse Fc (mIgG2a) or human Fc (hIgG1) at the C-terminal, coupled to amino acid residues 19-239 of full-length PD-L1 (SEQ ID NO: 351; NP_054862.1). Protein variants as exemplified by SEQ ID NO: 345 comprise a histidine tag at the C-terminal, coupled to amino acid residues 19-239 of NP_054862.1. Unless specified as being from a non-human species, the term "PD-L1" means human PD-L1.

PD-L1 is a 290 amino acid protein with extracellular IgV-like and IgC-like domains (amino acids 19-239 of full length PD-L1), a transmembrane domain and an intracellular domain of approximately 30 amino acids. PD-L1 is constitutively expressed on many cells such as antigen presenting cells (e.g., dendritic cells, macrophages, and B-cells) and on hematopoietic and non-hematopoietic cells (e.g., vascular endothelial cells, pancreatic islets, and sites of immune privilege). PD-L1 is also expressed on a wide variety of tumors, and virally-infected cells and is a component of the immunosuppressive milieu (Ribas 2012, NEJM 366: 2517-2519). PD-L1 binds to one of two T-cell co-inhibitors PD-1 and B7-1.

The term "PD-1" refers to the programmed death-1 protein, a T-cell co-inhibitor, also known as CD279. The amino acid sequence of full-length PD-1 is provided in GenBank as accession number NP 005009.2 and is also referred to herein as SEQ ID NO: 352. The term also encompasses PD-1 or a fragment thereof coupled to, for example, histidine tag, mouse or human Fc, or a signal sequence such as ROR1. For example, the term includes sequences exemplified by SEQ ID NOs: 349 or 350, comprising a mouse Fc (mIgG2a) or human Fc (hIgG1) at the C-terminal, coupled to amino acid residues 25-170 of NP_005009.2 with a C93S change.

PD-1 is a member of the CD28/CTLA-4/ICOS family of T-cell co-inhibitors. PD-1 is a 288-amino acid protein with an extracellular N-terminal domain which is IgV-like, a transmembrane domain and an intracellular domain containing an immunoreceptor tyrosine-based inhibitory (ITIM) motif and an immunoreceptor tyrosine-based switch (ITSM) motif (Chattopadhyay et al 2009, Immunol. Rev.). The PD-1 receptor has two ligands, PD-L1 and PD-L2.

The term "B7-1" refers to the T-lymphocyte activation antigen, also known as costimulatory factor CD80. B7-1 is a 288 amino acid membrane receptor with an extracellular N-terminal domain which comprises IgV-like (aa 37-138) and IgC-like (aa 154-232) regions, a transmembrane domain (aa 243-263) and a C-terminal intracellular region (aa 263-288). The amino acid sequence of full-length B7-1 is provided in GenBank as accession number NP_005182.1.

As used herein, the term "T-cell co-inhibitor" refers to a ligand and/or receptor which modulates the immune response via T-cell activation or suppression. The term "T-cell co-inhibitor", also known as T-cell co-signaling molecule, includes, but is not limited to, PD-1, lymphocyte activation gene 3 protein (LAG-3, also known as CD223), cytotoxic T-lymphocyte antigen-4 (CTLA-4), B and T lymphocyte attenuator (BTLA), CD-28, 2B4, LY108, T-cell immunoglobulin and mucin-3 (TIM3), T-cell immunoreceptor with immunoglobulin and ITIM (TIGIT; also known as VSIG9), leucocyte associated immunoglobulin-like receptor 1 (LAIR1; also known as CD305), inducible T-cell costimulator (ICOS; also known as CD278), B7-1 (CD80), and CD160.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-PD-L1 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-PD-L1 monoclonal antibodies comprising variants of any of the HCVR, LCVR, and/or CDR amino acid sequences disclosed herein having one or more conservative substitutions. For example, the present invention includes anti-PD-L1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "multi-specific antigen-binding molecules", as used herein refers to bispecific, tri-specific or multi-specific antigen-binding molecules, and antigen-binding fragments thereof. Multi-specific antigen-binding molecules may be specific for different epitopes of one target polypeptide or may contain antigen-binding domains specific for epitopes of more than one target polypeptide. A multi-specific antigen-binding molecule can be a single multifunctional polypeptide, or it can be a multimeric complex of two or more polypeptides that are covalently or non-covalently associated with one another. The term "multi-specific antigen-binding molecules" includes antibodies of the present invention that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity. According to the present invention, the term "multi-specific antigen-binding molecules" also includes bi-specific, tri-specific or multi-specific antibodies or antigen-binding fragments thereof. In certain embodiments, an antibody of the present invention is functionally linked to another antibody or antigen-binding fragment thereof to produce a bispecific antibody with a second binding specificity. Bispecific and multi-specific antibodies of the present invention are described elsewhere herein.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to PD-L1. Moreover, multi-specific antibodies that bind to one domain in PD-L1 and one or more additional antigens or a bi-specific that binds to two different regions of PD-L1 are nonetheless considered antibodies that "specifically bind", as used herein.

The term "high affinity" antibody refers to those mAbs having a binding affinity to PD-L1, expressed as $K_D$, of at least $10^{-8}$ M; preferably $10^{-8}$ M; more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from PD-L1, with a rate constant of $1 \times 10^{-3}$ $s^{-1}$ or less, preferably $1 \times 10^{-4}$ $s^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to PD-L1.

In specific embodiments, antibody or antibody fragments of the invention may be conjugated to a moiety such a ligand or a therapeutic moiety ("immunoconjugate"), such as an antibiotic, a second anti-PD-L1 antibody, or an antibody to another antigen such a tumor-specific antigen, a virally-infected cell antigen, or a T-cell co-inhibitor, or an immunotoxin, or any other therapeutic moiety useful for treating a disease or condition including e.g., cancer, chronic viral infection or autoimmune disease.

An "isolated antibody", as used herein, is intended to refer to an antibody that is substantially free of other antibodies (Abs) having different antigenic specificities (e.g., an isolated antibody that specifically binds PD-L1, or a fragment thereof, is substantially free of Abs that specifically bind antigens other than PD-L1.

A "blocking antibody" or a "neutralizing antibody", as used herein (or an "antibody that neutralizes PD-L1 activity" or an "antagonist antibody"), is intended to refer to an antibody whose binding to PD-L1 results in inhibition of at least one biological activity of PD-L1. For example, an antibody of the invention may prevent or block PD-L1 binding to PD-1 or to B7-1.

An "activating antibody" or an "enhancing antibody", as used herein (or an "agonist antibody"), is intended to refer to an antibody whose binding to PD-L1 results in increasing or stimulating at least one biological activity of PD-L1. For example, an antibody of the invention may increase or enhance PD-L1 binding to PD-1 or to B7-1.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as chronic viral infection, cancer or autoimmune disease.

As used herein, "anti-cancer drug" means any agent useful to treat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), interferons and radioactive agents. As used herein, "a cytotoxin or cytotoxic agent" means any agent that is detrimental to cells. Examples include Taxol® (paclitaxel), cytochalasin B, gramicidin D, ethidium bromide, emetine, mitomycin, etoposide, tenoposide, vincristine, vinbiastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, the term "anti-viral drug" refers to any drug or therapy used to treat, prevent, or ameliorate a viral infection in a host subject. The term "anti-viral drug" includes, but is not limited to zidovudine, lamivudine, abacavir, ribavirin, lopinavir, efavirenz, cobicistat, tenofovir, rilpivirine, analgesics and corticosteroids. In the context of the present invention, the viral infections include long-term or chronic infections caused by viruses including, but not limited to, human immunodeficiency virus (HIV), hepatitis B virus (HBV), hepatitis C virus (HCV), human papilloma virus (HPV), lymphocytic choriomeningitis virus (LCMV), and simian immunodeficiency virus (SIV).

The antibodies and antigen-binding fragments of the present invention specifically bind to PD-L1 and modulate the interaction of PD-L1 with PD-1 or with B7-1. The anti-PD-L1 antibodies may bind to PD-L1 with high affinity or with low affinity. In certain embodiments, the antibodies of the present invention are blocking antibodies wherein the antibodies bind to PD-L1 and block the interaction of PD-L1 with PD-1 or with B7-1. In some embodiments, the blocking antibodies of the invention block the binding of PD-L1 to PD-1 or to B7-1 and/or stimulate or enhance T-cell activation. In some embodiments, the blocking antibodies are useful for stimulating or enhancing the immune response and/or for treating a subject suffering from cancer, or a chronic viral infection. The antibodies when administered to a subject in need thereof may reduce the chronic infection by a virus such as HIV, LCMV or HBV in the subject. They may be used to inhibit the growth of tumor cells in a subject. They may be used alone or as adjunct therapy with other therapeutic moieties or modalities known in the art for treating cancer, or viral infection. In certain embodiments, the anti-PD-L1 antibodies that bind to PD-L1 with a low affinity are used as multi-specific antigen-binding molecules wherein the first binding specificity binds to PD-L1 with a low affinity and the second binding specificity binds to an antigen selected from the group consisting of a different epitope of PD-L1, a T-cell co-inhibitor such as PD-1, a tumor specific antigen and an infected-cell-specific antigen.

In certain embodiments, the antibodies of the present invention are agonist antibodies, wherein the antibodies bind to PD-L1 and enhance the interaction of PD-L1 and PD-1/B7-1. In some embodiments, the activating antibodies enhance binding of PD-L1 to PD-1 or to B7-1 and/or inhibit or suppress T-cell activation. The activating antibodies of the present invention may be useful for inhibiting the immune response in a subject and/or for treating autoimmune disease.

In certain embodiments, the anti-PD-L1 antibodies are multi-specific antigen-binding molecules, wherein they comprise a first binding specificity to PD-L1 and a second binding specificity to an antigen selected from the group consisting of a different epitope of PD-L1, a T-cell co-inhibitor such as PD-1, a tumor specific antigen and an infected-cell-specific antigen. In certain embodiments, the first binding specificity binds to PD-L1 with low affinity, e.g., with a $K_D$ of $10^{-8}$ M, $10^{-7}$ M or more.

Certain anti-PD-L1 antibodies of the present invention are able to bind to and neutralize the activity of PD-L1, as determined by in vitro or in vivo assays. The ability of the antibodies of the invention to bind to and neutralize the activity of PD-L1 may be measured using any standard method known to those skilled in the art, including binding assays, or activity assays, as described herein.

Non-limiting, exemplary in vitro assays for measuring binding activity are illustrated in Example 3, herein. In Example 3, the binding affinities and kinetic constants of human anti-PD-L1 antibodies for human PD-L1 and cynomolgus PD-L1 were determined by surface plasmon resonance and the measurements were conducted on a T200 Biacore instrument. In Examples 4 and 5, blocking assays were used to determine the ability of the anti-PD-L1 antibodies to block PD-L1-binding ability of PD-1 or to B7-1 in vitro. In Example 6, blocking assays were used to determine cross-competition between different anti-PD-L1 antibodies. Example 7 describes the binding of the antibodies to cells overexpressing PD-L1. In Example 8, a luciferase assay was used to determine the ability of anti-PD-L1 antibodies to antagonize PD-1/PD-L1 signaling in T-cells.

In certain embodiments, the antibodies of the present invention are able to enhance or stimulate T-cell activation in vitro and in a subject with cancer or in a subject infected with a virus such as LCMV. In certain embodiments, the antibodies of the present invention are used in combination with a second therapeutic agent, such as an antibody to a tumor-specific antigen or a T-cell co-inhibitor, to enhance the immune response and inhibit tumor growth in a subject. In certain embodiments, the agonist antibodies of the invention able to enhance PD-L1 binding to PD-1 or to B7-1 and may inhibit T-cell activation in vitro and/or in a subject with autoimmune disease.

The antibodies specific for PD-L1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to PD-L1. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide or fragment thereof of a multi-specific antigen-binding molecule. In such embodiments, the term "antigen-binding fragment" includes, e.g., an extracellular domain of PD-1 which binds specifically to PD-L1. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$- $C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to PD-L1.

An immunogen comprising any one of the following can be used to generate antibodies to PD-L1. In certain embodiments, the antibodies of the invention are obtained from mice immunized with a primary immunogen, such as a full length PD-L1 [See GenBank accession number NP_054862.1 (SEQ ID NO: 351)] or with a recombinant form of PD-L1 or modified human PD-L1 fragments (SEQ ID NOs: 345, 347 or 348) or with modified cynomolgus PD-L1 fragments (SEQ ID NO: 346), followed by immunization with a secondary immunogen, or with an immunogenically active fragment of PD-L1.

In certain embodiments, the immunogen may be a peptide from the N terminal or C terminal end of PD-L1. In one embodiment, the immunogen is the extracellular IgV-like and/or IgC-like domain of PD-L1. In certain embodiments of the invention, the immunogen is a fragment of PD-L1 that ranges from about amino acid residues 19-239 of SEQ ID NO: 351 (NP_054862.1).

In some embodiments, the immunogen may be a recombinant PD-L1 peptide expressed in *E. coli* or in any other eukaryotic or mammalian cells such as Chinese hamster ovary (CHO) cells.

In certain embodiments, antibodies that bind specifically to PD-L1 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of PD-L1 specific antibodies.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to PD-L1 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Bioequivalents

The anti-PD-L1 antibodies and antibody fragments of the present invention encompass proteins having amino acid sequences that vary from those of the described antibodies, but that retain the ability to bind PD-L1. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-PD-L1 Antibodies Comprising Fc Variants

According to certain embodiments of the present invention, anti-PD-L1 antibodies are provided comprising an Fc domain comprising one or more mutations which enhance or diminish antibody binding to the FcRn receptor, e.g., at acidic pH as compared to neutral pH. For example, the present invention includes anti-PD-L1 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0).

Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-PD-L1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present invention includes anti-PD-L1 antibodies comprising an Fc domain comprising a S108P mutation in the hinge region of IgG4 to promote dimer stabilization. All possible combinations of the foregoing Fc domain mutations, and other mutations within the antibody variable domains disclosed herein, are contemplated within the scope of the present invention.

The present invention also includes anti-PD-L1 antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Ser. No. 14/170,166, filed Jan. 31, 2014, the disclosure of which is hereby incorporated by reference in its entirety).

Biological Characteristics of the Antibodies

In general, the antibodies of the present invention function by binding to PD-L1. The present invention includes anti-PD-L1 antibodies and antigen-binding fragments thereof that bind soluble monomeric or dimeric PD-L1 molecules with high affinity. For example, the present invention includes antibodies and antigen-binding fragments of antibodies that bind monomeric PD-L1 (e.g., at 25° C. or at 37° C.) with a $K_D$ of less than about 318 pM as measured by surface plasmon resonance, e.g., using the assay format as defined in Example 3 herein. In certain embodiments, the antibodies or antigen-binding fragments thereof bind monomeric PD-L1 with a $K_D$ of less than about 300 pM, less than about 250 pM, less than about 150 pM, less than about 100 pM, or less than about 50 pM, as measured by surface plasmon resonance, e.g., using the assay format as defined in Example 3 herein, or a substantially similar assay.

The present invention also includes antibodies and antigen-binding fragments thereof that bind dimeric PD-L1 (e.g., at 25° C. or at 37° C.) with a $K_D$ of less than about 15 pM as measured by surface plasmon resonance, e.g., using the assay format as defined in Example 3 herein. In certain embodiments, the antibodies or antigen-binding fragments thereof bind dimeric PD-L1 with a $K_D$ of less than about 12 pM, less than about 10 pM, less than about 8 pM, or less than about 5 pM, as measured by surface plasmon resonance, e.g., using the assay format as defined in Example 3 herein, or a substantially similar assay.

The present invention also includes antibodies or antigen-binding fragments thereof that bind cynomolgus (*Macaca fascicularis*) PD-L1 (e.g., at 25° C. or at 37° C.) with a $K_D$ of less than about 28 nM as measured by surface plasmon resonance, e.g., using the assay format as defined in Example 3 herein. In certain embodiments, the antibodies or antigen-binding fragments thereof bind cynomolgus PD-L1 with a $K_D$ of less than about 25 nM, less than about 20 nM, less than about 15 nM, less than about 10 nM, or less than about 5 nM, as measured by surface plasmon resonance, e.g., using the assay format as defined in Example 3 herein, or a substantially similar assay.

The present invention also includes antibodies and antigen-binding fragments thereof that bind PD-L1 with a dissociative half-life (t½) of greater than about 1 minute as measured by surface plasmon resonance at 25° C. or 37° C., e.g., using an assay format as defined in Example 3 herein, or a substantially similar assay. In certain embodiments, the antibodies or antigen-binding fragments of the present invention bind PD-L1 with a t½ of greater than about 5 minutes, greater than about 10 minutes, greater than about 30 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, or greater than about 800 minutes, as measured by surface plasmon resonance at 25° C. or 37° C., e.g., using an assay format as defined in Example 3 herein (e.g., mAb-capture or antigen-capture format), or a substantially similar assay.

The present invention also includes antibodies or antigen-binding fragments thereof that block PD-L1 binding to PD-1 with an $IC_{50}$ of less than about 770 pM as determined using a ELISA-based immunoassay assay, e.g., as shown in Example 4, or a substantially similar assay. The present invention also includes antibodies or antigen-binding fragments thereof that block PD-L1 binding to B7-1 with an $IC_{50}$ of less than about 10 nM as determined using a ELISA-based immunoassay assay, e.g., as shown in Example 4, or a substantially similar assay. The present invention also includes antibodies and antigen-binding fragments thereof that bind to PD-L1 and enhance the binding of PD-L1 to PD-1 or to B7-1.

In some embodiments, the antibodies of the present invention may bind to the extracellular domain of PD-L1 or to a fragment of the domain. In some embodiments, the antibodies of the present invention may bind to more than one domain (cross-reactive antibodies). In certain embodiments, the antibodies of the present invention may bind to an epitope located in the extracellular domain comprising amino acid residues 19-239 of NP_054862.1 (SEQ ID NO: 351). In some embodiments, the antibodies may bind to an epitope comprising one or more amino acids selected from the group consisting of amino acid residues 1-221 of SEQ ID NOs: 345-348, or 353.

In certain embodiments, the antibodies of the present invention may function by blocking or inhibiting the PD-1-binding or the B7-1-binding activity associated with PD-L1 by binding to any other region or fragment of the full length protein, the amino acid sequence of which is shown in SEQ ID NO: 351. In certain embodiments, the antibodies may attenuate or modulate the interaction between PD-L1 and PD-1/B7-1.

In certain embodiments, the antibodies of the present invention may be bi-specific antibodies. The bi-specific antibodies of the invention may bind one epitope in one domain and may also bind a second epitope in a different domain of PD-L1. In certain embodiments, the bi-specific antibodies of the invention may bind two different epitopes in the same domain. In one embodiment, the multi-specific antigen-binding molecule comprises a first antigen-binding specificity wherein the first binding specificity comprises the extracellular domain or fragment thereof of PD-1; and a second antigen-binding specificity to another epitope of PD-L1. In another embodiment, the multi-specific antigen-binding molecule comprises a first antigen-binding specificity wherein the first binding specificity comprises the extracellular domain or fragment thereof of B7-1; and a second antigen-binding specificity to another epitope of PD-L1.

In one embodiment, the invention provides a fully human monoclonal antibody or antigen-binding fragment thereof that binds to PD-L1, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 186, 202, 218, 234, 250, 258, 266, 274, 282, 290, 298, 306, 314, 322, 330 and 338, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 194, 210, 226, 242, 258, and 274, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 192, 208, 224, 240, 256, 272, 280, 288, 296, 304, 312, 320, 328, 336 and 344, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 200, 216, 232, 248, 264, and 280, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 188, 204, 220, 236, 252, 268, 284, 292, 300, 308, 316, 324, 332, and 340, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 190, 206, 222, 238, 254, 270, 286, 294, 302, 310, 318, 326, 334, and 342, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 196, 212, 228, 244, 260, and 276, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 198, 214, 230, 246, 262, and 278, or a substantially similar sequence thereof having at least 90%, at least 95%, at least 98% or at least 99% sequence identity; (v) is a multi-specific antigen-binding molecule comprising a first binding specificity to PD-L1 and a second binding specificity to an antigen selected from the group consisting of PD-L1, a tumor specific antigen, a virally infected cell antigen, and a T-cell co-inhibitor; (vi) binds to human PD-L1 with a $K_D$ of about 4 pM to about 645 nM; (vii) binds to cynomolgus PD-L1 with a $K_D$ of about 70 pM to about 400 nM; (viii) blocks or enhances the binding of PD-L1 to PD-1 with an IC50≤770 pM; (ix) blocks or enhances the binding of PD-L1 to B7-1 with an IC50≤10 nM; (x) blocks PD-1-induced T-cell down-regulation and/or rescues T-cell signaling in a T-cell/APC luciferase reporter assay; (xi) stimulates T-cell proliferation and activity in a mixed lymphocyte reaction (MLR) assay; (xii) induces IL-2 and/or IFNγ production in a MLR assay; and (xiii) suppresses tumor growth and increases survival in subjects with cancer.

In one embodiment, the invention provides a fully human monoclonal antibody or antigen-binding fragment thereof that blocks PD-L1 binding to PD-1 or to B7-1, wherein the antibody or fragment thereof exhibits one or more of the following characteristics: (i) comprises a HCVR having an amino acid sequence selected from the group consisting of SEQ ID NO: 82, 98, 146, 162, 290, 306, 314, and 330, or a substantially similar sequence thereof having at least 90%, at least 95%, at least 98% or at least 99% sequence identity; (ii) comprises a LCVR having an amino acid sequence selected from the group consisting of SEQ ID NO: 90, 106, 154, 170, and 274, or a substantially similar sequence thereof having at least 90%, at least 95%, at least 98% or at least 99% sequence identity; (iii) comprises a HCDR3 domain having an amino acid sequence selected from the group consisting of SEQ ID NO: 88, 104, 152, 168, 296, 312, 320, and 336, or a substantially similar sequence thereof having at least 90%, at least 95%, at least 98% or at least 99% sequence identity; and a LCDR3 domain having an amino acid sequence selected from the group consisting of SEQ ID NO: 96, 112, 160, 176, and 280, or a substantially similar sequence thereof having at least 90%, at least 95%, at least 98% or at least 99% sequence identity; (iv) comprises a HCDR1 domain having an amino acid sequence selected from the group consisting of SEQ ID NO: 84, 100, 148, 164, 292, 308, 316, and 332, or a substantially similar sequence thereof having at least 90%, at least 95%, at least 98% or at least 99% sequence identity; a HCDR2 domain having an amino acid sequence selected from the group consisting of SEQ ID NO: 86, 102, 150, 166, 294, 310, 318, and 334, or a substantially similar sequence thereof having at least 90%, at least 95%, at least 98% or at least 99% sequence identity; a LCDR1 domain having an amino acid sequence selected from the group consisting of SEQ ID NO: 92, 108, 156, 172, and 276, or a substantially similar sequence thereof having at least 90%, at least 95%, at least 98% or at least 99% sequence identity; and a LCDR2 domain having an amino acid sequence selected from the group consisting of SEQ ID NO: 94, 110, 158, 174, and 278, or a substantially similar sequence thereof having at least 90%, at least 95%, at least 98% or at least 99% sequence identity; (v) is a multi-specific antigen-binding molecule comprising a first binding specificity to PD-L1 and a second binding specificity to an antigen selected from the group consisting of a different epitope of PD-L1, a tumor specific antigen, a virally-infected cell antigen, and a T-cell co-inhibitor; (vi) binds to human PD-L1 with a $K_D \leq 10^{-10}$M; (vii) binds to cynomolgus PD-L1 with a $K_D \leq 10^{-7}$M; (viii) blocks the binding of PD-L1 to PD-1 or to B7-1; (ix) blocks PD-1-induced T-cell down-regulation and/or rescues T-cell signaling in a T-cell/APC luciferase reporter assay; (xi) stimulates T-cell proliferation and activity in a mixed lymphocyte reaction (MLR) assay; (xii) induces IL-2 and/or IFNγ production in a MLR assay; and (xiii) suppresses tumor growth and increases survival in subjects with cancer.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Species Selectivity and Species Cross-Reactivity

According to certain embodiments of the invention, the anti-PD-L1 antibodies bind to human PD-L1 but not to PD-L1 from other species. Alternatively, the anti-PD-L1 antibodies of the invention, in certain embodiments, bind to human PD-L1 and to PD-L1 from one or more non-human species. For example, the anti-PD-L1 antibodies of the invention may bind to human PD-L1 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee PD-L1. In certain embodiments, the anti-PD-L1 antibodies of the invention may bind to human and cynomolgus PD-L1 with the same affinities or with different affinities.

Epitope Mapping and Related Technologies

The present invention includes anti-PD-L1 antibodies which interact with one or more amino acids found within one or more domains of the PD-L1 molecule including, e.g., extracellular (IgV-like) domain, the extracellular IgC-like domain, a transmembrane domain, and an intracellular domain. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the PD-L1 molecule (e.g. a linear epitope in a domain). Alternatively, the epitope may consist of a plurality of non-contiguous amino acids (or amino acid sequences) located within either or both of the aforementioned domains of the PD-L1 molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-PD-L1 antibodies or antigen-binding fragments thereof bind an epitope within any one or more of the regions exemplified in PD-L1, either in natural form, as exemplified in SEQ ID NO: 351, or recombinantly produced, as exemplified in SEQ ID NOS: 345-348, or to a fragment thereof. In some embodiments, the antibodies of the invention bind to an extracellular region comprising one or more amino acids selected from the group consisting of amino acid residues 19-239 of PD-L1. In some embodiments, the antibodies of the invention bind to a region comprising one or more amino acids selected from the group consisting of amino acid residues 1-221 of cynomolgus PD-L1, as exemplified by SEQ ID NO: 346.

In certain embodiments, the antibodies of the invention, as shown in Table 1, interact with at least one amino acid sequence selected from the group consisting of amino acid residues ranging from about position 19 to about position 130 of SEQ ID NO: 351; or amino acid residues ranging from about position 130 to about position 153 of SEQ ID NO: 351; or amino acid residues ranging from about position 153 to about position 210 of SEQ ID NO: 351; or to amino acid residues ranging from about position 210 to about position 239 of SEQ ID NO: 351. These regions are partially exemplified in SEQ ID NOs: 345-348.

The present invention includes anti-PD-L1 antibodies that bind to the same epitope, or a portion of the epitope, as any of the specific exemplary antibodies described herein in Table 1, or an antibody having the CDR sequences of any of the exemplary antibodies described in Table 1. Likewise, the present invention also includes anti-PD-L1 antibodies that compete for binding to PD-L1 or a PD-L1 fragment with any of the specific exemplary antibodies described herein in Table 1, or an antibody having the CDR sequences of any of the exemplary antibodies described in Table 1. For example, the present invention includes anti-PD-L1 antibodies that cross-compete for binding to PD-L1 with one or more antibodies as defined in Example 6 herein (e.g., H2aM8309N, H1H9329P, H1H9336P, H2aM8314N, H2aM8316N, H2AM8718N, H1H9387P2, H1H9351P2, H1H9364P2, H1H9373P2, and H2aM8306N). The present invention also includes anti-PD-L1 antibodies that cross-compete for binding to PD-L1 with one or more antibodies as defined in Example 6 herein (e.g., H1H9396P2, H2aM8317N, H2aM8321N, H1H9323P, H1H9382P2, H1H9344P2, H1H9345P2 and H1H9354P2).

One can easily determine whether an antibody binds to the same epitope as, or competes for binding with, a reference anti-PD-L1 antibody by using routine methods known in the art. For example, to determine if a test antibody binds to the same epitope as a reference anti-PD-L1 antibody of the invention, the reference antibody is allowed to bind to a PD-L1 protein or peptide under saturating conditions. Next, the ability of a test antibody to bind to the PD-L1 molecule is assessed. If the test antibody is able to bind to PD-L1 following saturation binding with the reference anti-PD-L1 antibody, it can be concluded that the test antibody binds to a different epitope than the reference anti-PD-L1 antibody. On the other hand, if the test antibody is not able to bind to the PD-L1 protein following saturation binding with the reference anti-PD-L1 antibody, then the test antibody may bind to the same epitope as the epitope bound by the reference anti-PD-L1 antibody of the invention.

To determine if an antibody competes for binding with a reference anti-PD-L1 antibody, the above-described binding methodology is performed in two orientations: In a first orientation, the reference antibody is allowed to bind to a PD-L1 protein under saturating conditions followed by assessment of binding of the test antibody to the PD-L1 molecule. In a second orientation, the test antibody is allowed to bind to a PD-L1 molecule under saturating conditions followed by assessment of binding of the reference antibody to the PD-L1 molecule. If, in both orientations, only the first (saturating) antibody is capable of binding to the PD-L1 molecule, then it is concluded that the test antibody and the reference antibody compete for binding to PD-L1. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-PD-L1 monoclonal antibody conjugated to a therapeutic moiety ("immunoconjugate"), such as a cytotoxin or a chemotherapeutic agent to treat cancer. As used herein, the term "immunoconjugate" refers to an antibody which is chemically or biologically linked to a cytotoxin, a radioactive agent, a cytokine, an interferon, a target or reporter moiety, an enzyme, a toxin, a peptide or protein or a therapeutic agent. The antibody may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antibody drug conjugates and antibody-toxin fusion proteins. In one embodiment, the agent may be a second different antibody to PD-L1. In certain embodiments, the antibody may be conjugated to an agent specific for a tumor cell or a virally infected cell. The type of therapeutic moiety that may be conjugated to the anti-PD-L1 antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

In one aspect, the present invention includes multi-specific antigen-binding molecules or antigen-binding fragments thereof wherein one antigen-binding specificity of an immunoglobulin is specific for an epitope within the extracellular domain of PD-L1 (e.g., in the IgV-like region), or a fragment thereof, and the other antigen-binding specificity of the immunoglobulin is specific for binding to a different epitope in the extracellular domain of PD-L1 (e.g., in the IgC-like region), or a second therapeutic target, or is conjugated to a therapeutic moiety. In certain embodiments, the first antigen-binding specificity may comprise PD-1 or B7-1 or a fragment thereof. In one embodiment, the first antigen-binding specificity that binds to PD-L1 comprises the extracellular domain of PD-1. In certain embodiments of the invention, one antigen-binding specificity of an immunoglobulin is specific for an epitope within amino acid residues 19-239 of PD-L1 (SEQ ID NO: 351) or a fragment thereof, and the other specificity of the immunoglobulin is specific for a second target antigen. The second target antigen may be on the same cell as PD-L1 or on a different cell. In one embodiment, the second target cell is on an immune cell other than a T-cell such as a B-cell, antigen-presenting cell, monocyte, macrophage, or dendritic cell. In some embodiments, the second target antigen may be present on a tumor cell or on a virally infected cell.

In another aspect, the invention provides multi-specific antigen-binding molecules or antigen-binding fragments thereof comprising a first antigen-binding specificity that binds to PD-L1 and a second antigen-binding specificity that binds specifically to a target antigen on a tumor cell. In various embodiments, the tumor-specific antigen is one of CA9, CA125, melanoma-associated antigen (MAGE), carcinoembryonic antigen (CEA), vimentin, tumor-M2-PK, prostate-specific antigen (PSA), MART-1, or CA19-9. Non-limiting examples of other specific tumor-associated antigens include, e.g., AFP, ALK, BAGE proteins, β-catenin, brc-abl, BRCA1, BORIS, carbonic anhydrase IX, caspase-8, CCR5, CD19, CD20, CD30, CD40, CDK4, CTLA4, cyclin-B1, CYP1B1, EGFR, EGFRvIII, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), HLA-A2, MART-1, mesothelin, ML-IAP, Muc1, Muc2, Muc3, Muc4, Muc5, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, Steap-1, Steap-2, survivin, TAG-72, TGF-6, TMPRSS2, Tn, TRP-1, TRP-2, tyrosinase, and uroplakin-3. In other embodiments, the second antigen-binding specificity binds to a tumor antigen that is present on tumor cells specific to, but not limited to, renal cell carcinoma, prostate cancer, colorectal cancer, melanoma, breast cancer, kidney cancer, ovarian cancer, and pancreatic cancer. The antibodies of the invention, in this aspect, may inhibit the activity of PD-L1.

In another aspect, the invention provides multi-specific antigen-binding molecules or antigen-binding fragments thereof wherein the second antigen-binding specificity binds to an antigen specific to a virally-infected cell. In certain embodiments, the second antigen-binding specificity binds to an antigen specific to a cell infected with a virus selected from the group consisting of HIV, HBV, HCV, HPV, LCMV and SIV.

In another aspect, the invention provides multi-specific antigen-binding molecules or antigen-binding fragments thereof comprising a first antigen-binding specificity that binds to PD-L1 and a second antigen-binding specificity that binds to a T-cell co-inhibitor such as PD-1, LAG-3, TIM3, B7-1, CTLA-4, BTLA, CD-28, 2B4, LY108, TIGIT, LAIR1, ICOS and CD160.

Any of the multi-specific antigen-binding molecules, or variants thereof, may be constructed using standard molecular biological techniques (e.g., recombinant DNA and protein expression technology), as will be well known to a person of ordinary skill in the art.

In some embodiments, PD-L1-specific antibodies are generated in a bi-specific format (a "bi-specific") in which variable regions binding to distinct domains of PD-L1 are linked together to confer dual-domain specificity within a single binding molecule. Appropriately designed bi-specifics may enhance overall PD-L1 inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L 1$) can be combined with two different $V_H$ domains (e.g., $V_H 1$ and $V_H 2$) to generate a bi-specific comprised of two binding "arms" ($V_H 1$-$V_L 1$ and $V_H 2$-$V_L 1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domains and a second target, such as, but not limited to, for example, a second different anti-PD-L1 antibody, may be prepared in a bi-specific format using techniques described herein, or other techniques known to those skilled in the art. Antibody variable regions binding to distinct regions may be linked together with variable regions that bind to relevant sites on, for example, the extracellular domain of PD-L1, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H 3$ domain and a second Ig $C_H 3$ domain, wherein the first and second Ig $C_H 3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H 3$ domain binds Protein A and the second Ig $C_H 3$ domain contains a mutation that reduces or abolishes Protein A binding such as an H95R modification (by IMGT exon numbering; H435R by EU numbering). The second $C_H 3$ may further comprise a Y96F modification (by IMGT; Y436F by EU). Further modifications that may be found within the second $C_H 3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^e$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [*Epub*: Dec. 4, 2012]).

Therapeutic Administration and Formulations

The invention provides therapeutic compositions comprising the anti-PD-L1 antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 100 mg/kg body weight, more preferably about 5 to about 80, about 10 to about 60, or about 20 to about 50 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target tumor cells or autoimmune tissue cells or virally infected cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 100 mg and in about 10 to about 250 mg for the other dosage forms.

Therapeutic Uses of the Antibodies

The antibodies of the present invention are useful for the treatment, prevention, and/or amelioration of disease or disorder or condition such as cancer, autoimmune disease or a viral infection and/or for ameliorating at least one symptom associated with such disease, disorder or condition. In some embodiments of the invention, the antibodies described herein are useful for treating subjects suffering from primary or recurrent cancer, including for example, renal cell carcinoma, prostate cancer, ovarian cancer, kidney cancer, colorectal cancer, gastric cancer, breast cancer, head and neck cancer, non-small-cell lung cancer, brain cancer, multiple myeloma, and melanoma. The antibodies may be used to treat early stage or late-stage symptoms of cancer. In one embodiment, an antibody or fragment thereof of the invention may be used to treat metastatic cancer. The antibodies are useful in reducing or inhibiting or shrinking tumor growth of both solid tumors and blood cancers. In certain embodiments, the antibodies may be used to prevent relapse of a tumor. In certain embodiments, treatment with an antibody or antigen-binding fragment thereof of the invention may lead to more than 50% regression, more than 60% regression, more than 70% regression, more than 80% regression or more than 90% regression of a tumor in a subject. In certain embodiments, the antibodies may be used to increase survival of a subject suffering from cancer.

In certain embodiments, the antibodies of the invention are useful to treat subjects suffering from a chronic viral infection. In some embodiments, the antibodies of the invention are useful in decreasing viral titers in the host and/or rescuing exhausted T-cells. In one embodiment, an antibody or antigen-binding fragment thereof the invention may be administered at a therapeutic dose to a patient with an infection by human immunodeficiency virus (HIV) or human papilloma virus (HPV) or hepatitis B/C virus (HBV/HCV). In a related embodiment, an antibody or antigen-binding fragment thereof of the invention may be used to treat an infection by simian immunodeficiency virus (SIV) in a simian subject such as cynomolgus. In another embodiment, an antibody or fragment thereof of the invention may be used to treat chronic viral infection by lymphocytic choriomeningitis virus (LCMV).

In certain embodiments, a blocking antibody of the present invention may be administered in a therapeutically effective amount to a subject suffering from cancer or a viral infection.

In certain embodiments, the antibodies of the invention are useful for treating an autoimmune disease, including but not limited to, alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjögren's syndrome, systemic lupus erthyematosus, vitiligo, autoimmune pancreatitis, autoimmune urticaria, autoimmune thrombocytopenic purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis. In certain embodiments, an activating antibody of the invention may be used to treat a subject suffering from autoimmune disease.

One or more antibodies of the present invention may be administered to relieve or prevent or decrease the severity of one or more of the symptoms or conditions of the disease or disorder.

It is also contemplated herein to use one or more antibodies of the present invention prophylactically to patients at risk for developing a disease or disorder such as cancer, and chronic viral infection.

In a further embodiment of the invention the present antibodies are used for the preparation of a pharmaceutical composition for treating patients suffering from cancer, autoimmune disease or viral infection. In another embodiment of the invention, the present antibodies are used as adjunct therapy with any other agent or any other therapy known to those skilled in the art useful for treating cancer, autoimmune disease or viral infection.

Combination Therapies

Combination therapies may include an anti-PD-L1 antibody of the invention and any additional therapeutic agent that may be advantageously combined with an antibody of the invention, or with a biologically active fragment of an antibody of the invention.

The antibodies of the present invention may be combined synergistically with one or more anti-cancer drugs or therapy used to treat cancer, including, for example, renal cell carcinoma, ovarian cancer, prostate cancer, colorectal cancer, non-small-cell lung cancer, and melanoma. It is contemplated herein to use anti-PD-L1 antibodies of the invention in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

In various embodiments, one or more antibodies of the present invention may be used in combination with a second antibody to PD-L1, an antibody to PD-1 (e.g., nivolumab), a LAG-3 inhibitor, a CTLA-4 inhibitor (e.g., ipilimumab), a TIM3 inhibitor, a BTLA inhibitor, a TIGIT inhibitor, a CD47 inhibitor, an antagonist of another T-cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), an agonist to a co-stimulatory receptor (e.g., an agonist to glucocorticoid-induced TNFR-related protein), an antibody to a tumor-specific antigen (e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9), a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3×CD20 bispecific antibody, PSMAxCD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any palliative care to treat cancer. In certain embodiments, the anti-PD-L1 antibodies of the present invention may be used in combination with cancer vaccines including dendritic cell vaccines, oncolytic viruses, tumor cell vaccines, etc. to augment the anti-tumor response. Examples of cancer vaccines that can be used in combination with anti-PD-L1 antibodies of the present invention include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers). In certain embodiments, the anti-PD-L1 antibodies of the present invention may be used in combination with a dietary supplement such as anti-oxidants or any palliative care to treat cancer.

In certain embodiments, the anti-PD-L1 antibodies of the invention may be administered in combination with radiation therapy in methods to generate long-term durable anti-tumor responses and/or enhance survival of patients with cancer. In some embodiments, the anti-PD-L1 antibodies of the invention may be administered prior to, concomitantly or after administering radiation therapy to a cancer patient. For example, radiation therapy may be administered in one or more doses to tumor lesions followed by administration of one or more doses of anti-PD-L1 antibodies of the invention. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-PD-L1 antibody of the invention. For example, intracranial radiation may be administered to a patient with brain cancer (e.g., glioblastoma multiforme) along with systemic administration of an anti-PD-L1 antibody of the invention. In certain embodiments, the anti-PD-L1 antibodies of the invention may be administered in combination with radiation therapy and a chemotherapeutic agent (e.g., temozolomide) or a VEGF antagonist (e.g., aflibercept).

The antibodies or fragments thereof of the invention may be administered in combination with one or more anti-viral drugs known in the art, including but not limited to, zidovudine, lamivudine, abacavir, ribavirin, lopinavir, efavirenz, cobicistat, tenofovir, rilpivirine and corticosteroids. In some embodiments, the anti-PD-L1 antibodies of the invention may be administered in combination with a LAG3 inhibitor, a CTLA-4 inhibitor, a PD-1 inhibitor or any antagonist of another T-cell co-inhibitor to treat chronic viral infection.

The antibodies of fragments thereof of the invention may be used in combination with any drug or therapy known in the art (e.g., corticosteroids and other immunosuppressants) to treat an autoimmune disease or disorder including, but not limited to, alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjögren's syndrome, systemic lupus erthyematosus, vitiligo, autoimmune pancreatitis, autoimmune urticaira, autoimmune thrombocytopenic purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis.

The additional therapeutically active component(s) may be administered prior to, concurrent with, or after the administration of the anti-PD-L1 antibody of the present invention. For purposes of the present disclosure, such administration regimens are considered the administration of an anti-PD-L1 antibody "in combination with" a second therapeutically active component.

The additional therapeutically active component(s) may be administered to a subject prior to administration of an anti-PD-L1 antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-PD-L1 antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-PD-L1 antibody of the present invention. "Concurrent" administration, for purposes of the present invention, includes, e.g., administration of an anti-PD-L1 antibody and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-PD-L1 antibody and the additional therapeutically active component may be administered intravenously, subcutaneously, etc.); alternatively, each dosage form may be administered via a different route (e.g., the anti-PD-L1 antibody may be administered intravenously, and the additional therapeutically active component may be administered subcutaneously). In any event, administering the components in a single dosage from, in separate dosage forms by the same route, or in separate dosage forms by different routes are all considered "concurrent administration," for purposes of the present disclosure. For purposes of the present disclosure, administration of an anti-PD-L1 antibody "prior to", "concurrent with," or "after" (as those terms are defined herein above) administration of an additional therapeutically active component is considered administration of an anti-PD-L1 antibody "in combination with" an additional therapeutically active component).

The present invention includes pharmaceutical compositions in which an anti-PD-L1 antibody of the present invention is co-formulated with one or more of the additional therapeutically active component(s) as described elsewhere herein using a variety of dosage combinations.

In exemplary embodiments in which an anti-PD-L1 antibody of the invention is administered in combination with a VEGF antagonist (e.g., a VEGF trap such as aflibercept), including administration of co-formulations comprising an anti-PD-L1 antibody and a VEGF antagonist, the individual components may be administered to a subject and/or co-formulated using a variety of dosage combinations. For example, the anti-PD-L1 antibody may be administered to a subject and/or contained in a co-formulation in an amount selected from the group consisting of 0.01 mg, 0.02 mg, 0.03 mg, 0.04 mg, 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, 6.0 mg, 7.0 mg, 8.0 mg, 9.0 mg, and 10.0 mg; and the VEGF antagonist (e.g., a VEGF trap such as aflibercept) may be administered to the subject and/or contained in a co-formulation in an amount selected from the group consisting of 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg and 3.0 mg. The combinations/co-formulations may be administered to a subject according to any of the administration regimens disclosed elsewhere herein, including, e.g., twice a week, once every week, once every 2 weeks, once every 3 weeks, once every month, once every 2 months, once every 3 months, once every 4 months, once every 5 months, once every 6 months, etc.

Administrative Regimens

According to certain embodiments of the present invention, multiple doses of an anti-PD-L1 antibody (or a pharmaceutical composition comprising a combination of an anti-PD-L1 antibody and any of the additional therapeutically active agents mentioned herein) may be administered to a subject over a defined time course. The methods according to this aspect of the invention comprise sequentially administering to a subject multiple doses of an anti-PD-L1 antibody of the invention. As used herein, "sequentially administering" means that each dose of anti-PD-L1 antibody is administered to the subject at a different point in time, e.g., on different days separated by a predetermined interval (e.g., hours, days, weeks or months). The present invention includes methods which comprise sequentially administering to the patient a single initial dose of an anti-PD-L1 antibody, followed by one or more secondary doses of the anti-PD-L1 antibody, and optionally followed by one or more tertiary doses of the anti-PD-L1 antibody. The anti-PD-L1 antibody may be administered at a dose of between 0.1 mg/kg to about 100 mg/kg.

The terms "initial dose," "secondary doses," and "tertiary doses," refer to the temporal sequence of administration of the anti-PD-L1 antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-PD-L1 antibody, but generally may differ from one another in terms of frequency of administration. In certain embodiments, however, the amount of anti-PD-L1 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-PD-L1 antibody which is administered to a patient prior to the administration of the very next dose in the sequence with no intervening doses.

The methods according to this aspect of the invention may comprise administering to a patient any number of secondary and/or tertiary doses of an anti-PD-L1 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of, e.g., once a month (e.g., two, three, four, or more loading doses administered once a month), then the maintenance doses may be administered to the patient once every five weeks, once every six weeks, once every seven weeks, once every eight weeks, once every ten weeks, once every twelve weeks, etc.).

Diagnostic Uses of the Antibodies

The anti-PD-L1 antibodies of the present invention may be used to detect and/or measure PD-L1 in a sample, e.g., for diagnostic purposes. Some embodiments contemplate the use of one or more antibodies of the present invention in assays to detect a disease or disorder such as cancer, autoimmune disease or chronic viral infection. Exemplary diagnostic assays for PD-L1 may comprise, e.g., contacting a sample, obtained from a patient, with an anti-PD-L1 antibody of the invention, wherein the anti-PD-L1 antibody is labeled with a detectable label or reporter molecule or used as a capture ligand to selectively isolate PD-L1 from patient samples. Alternatively, an unlabeled anti-PD-L1 antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure PD-L1 in a sample include enzyme-linked immunosorbent assay (ELISA), radioimmunoassay (RIA), and fluorescence-activated cell sorting (FACS).

Samples that can be used in PD-L1 diagnostic assays according to the present invention include any tissue or fluid sample obtainable from a patient, which contains detectable quantities of either PD-L1 protein, or fragments thereof, under normal or pathological conditions. Generally, levels of PD-L1 in a particular sample obtained from a healthy patient (e.g., a patient not afflicted with cancer or an autoimmune disease) will be measured to initially establish a baseline, or standard, level of PD-L1. This baseline level of PD-L1 can then be compared against the levels of PD-L1 measured in samples obtained from individuals suspected of having a cancer-related condition, or symptoms associated with such condition.

The antibodies specific for PD-L1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Aspects of the invention relate to use of the disclosed antibodies as markers for predicting prognosis of cancer or an autoimmune disorder in patients. Antibodies of the present invention may be used in diagnostic assays to evaluate prognosis of cancer in a patient and to predict survival.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to PD-L1

Human antibodies to PD-L1 were generated using a fragment of PD-L1 that ranges from about amino acids 19-239 of SEQ ID NO: 351 (Genbank Accession No. NP_054862.1). The immunogen was administered directly, with an adjuvant to stimulate the immune response, to a VELOCIMMUNE® mouse comprising DNA encoding human Immunoglobulin heavy and kappa light chain variable regions. The antibody immune response was monitored by a PD-L1-specific immunoassay. When a desired immune response was achieved splenocytes were harvested and fused with mouse myeloma cells to preserve their viability and form hybridoma cell lines. The hybridoma cell lines were screened and selected to identify cell lines that produce PD-L1-specific antibodies. Using this technique, and the immunogen described above, several anti-PD-L1 chimeric antibodies (i.e., antibodies possessing human variable domains and mouse constant domains) were obtained; exemplary antibodies generated in this manner were designated as H2M8306N, H2M8307N, H2M8309N, H2M8310N, H2M8312N, H2M8314N, H2M8316N, H2M8317N, H2M8321N, H2M8323N, H2M8718N, H2M8718N2, and H2M8719N.

Anti-PD-L1 antibodies were also isolated directly from antigen-positive B cells without fusion to myeloma cells, as described in U.S. 2007/0280945A1, herein specifically incorporated by reference in its entirety. Using this method, several fully human anti-PD-L1 antibodies (i.e., antibodies possessing human variable domains and human constant domains) were obtained; exemplary antibodies generated in this manner were designated as follows: H1H9323P, H1H9327P, H1H9329P, H1H9336P, H1H9344P2, H1H9345P2, H1H9351P2, H1H9354P2, H1H9364P2, H1H9373P2, H1H9382P2, H1H9387P2, and H1H9396P2.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-PD-L1 antibodies of the invention. The corresponding nucleic acid sequence identifiers are set forth in Table 2.

TABLE 1

| Antibody Designation | Amino Acid Sequence Identifiers SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H2M8306N | 2 | 4 | 6 | 8 | 10 | 12 | 14 | 16 |
| H2M8307N | 18 | 20 | 22 | 24 | 26 | 28 | 30 | 32 |
| H2M8309N | 34 | 36 | 38 | 40 | 42 | 44 | 46 | 48 |
| H2M8310N | 50 | 52 | 54 | 56 | 58 | 60 | 62 | 64 |
| H2M8312N | 66 | 68 | 70 | 72 | 74 | 76 | 78 | 80 |
| H2M8314N | 82 | 84 | 86 | 88 | 90 | 92 | 94 | 96 |
| H2M8316N | 98 | 100 | 102 | 104 | 106 | 108 | 110 | 112 |
| H2M8317N | 114 | 116 | 118 | 120 | 122 | 124 | 126 | 128 |
| H2M8321N | 130 | 132 | 134 | 136 | 138 | 140 | 142 | 144 |
| H2M8323N | 146 | 148 | 150 | 152 | 154 | 156 | 158 | 160 |
| H2M8718N | 162 | 164 | 166 | 168 | 170 | 172 | 174 | 176 |
| H2M8718N2 | 178 | 180 | 182 | 184 | 170 | 172 | 174 | 176 |
| H2M8719N | 186 | 188 | 190 | 192 | 194 | 196 | 198 | 200 |
| H1H9323P | 202 | 204 | 206 | 208 | 210 | 212 | 214 | 216 |
| H1H9327P | 218 | 220 | 222 | 224 | 226 | 228 | 230 | 232 |
| H1H9329P | 234 | 236 | 238 | 240 | 242 | 244 | 246 | 248 |
| H1H9336P | 250 | 252 | 254 | 256 | 258 | 260 | 262 | 264 |
| H1H9344P2 | 266 | 268 | 270 | 272 | 274 | 276 | 278 | 280 |
| H1H9345P2 | 282 | 284 | 286 | 288 | 274 | 276 | 278 | 280 |

TABLE 1-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H9351P2 | 290 | 292 | 294 | 296 | 274 | 276 | 278 | 280 |
| H1H9354P2 | 298 | 300 | 302 | 304 | 274 | 276 | 278 | 280 |
| H1H9364P2 | 306 | 308 | 310 | 312 | 274 | 276 | 278 | 280 |
| H1H9373P2 | 314 | 316 | 318 | 320 | 274 | 276 | 278 | 280 |
| H1H9382P2 | 322 | 324 | 326 | 328 | 274 | 276 | 278 | 280 |
| H1H9387P2 | 330 | 332 | 334 | 336 | 274 | 276 | 278 | 280 |
| H1H9396P2 | 338 | 340 | 342 | 344 | 274 | 276 | 278 | 280 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H2M8306N | 1 | 3 | 5 | 7 | 9 | 11 | 13 | 15 |
| H2M8307N | 17 | 19 | 21 | 23 | 25 | 27 | 29 | 31 |
| H2M8309N | 33 | 35 | 37 | 39 | 41 | 43 | 45 | 47 |
| H2M8310N | 49 | 51 | 53 | 55 | 57 | 59 | 61 | 63 |
| H2M8312N | 65 | 67 | 69 | 71 | 73 | 75 | 77 | 79 |
| H2M8314N | 81 | 83 | 85 | 87 | 89 | 91 | 93 | 95 |
| H2M8316N | 97 | 99 | 101 | 103 | 105 | 107 | 109 | 111 |
| H2M8317N | 113 | 115 | 117 | 119 | 121 | 123 | 125 | 127 |
| H2M8321N | 129 | 131 | 133 | 135 | 137 | 139 | 141 | 143 |
| H2M8323N | 145 | 147 | 149 | 151 | 153 | 155 | 157 | 159 |
| H2M8718N | 161 | 163 | 165 | 167 | 169 | 171 | 173 | 175 |
| H2M8718N2 | 177 | 179 | 181 | 183 | 169 | 171 | 173 | 175 |
| H2M8719N | 185 | 187 | 189 | 191 | 193 | 195 | 197 | 199 |
| H1H9323P | 201 | 203 | 205 | 207 | 209 | 211 | 213 | 215 |
| H1H9327P | 217 | 219 | 221 | 223 | 225 | 227 | 229 | 231 |
| H1H9329P | 233 | 235 | 237 | 239 | 241 | 243 | 245 | 247 |
| H1H9336P | 249 | 251 | 253 | 255 | 257 | 259 | 261 | 263 |
| H1H9344P2 | 265 | 267 | 269 | 271 | 273 | 275 | 277 | 279 |
| H1H9345P2 | 281 | 283 | 285 | 287 | 273 | 275 | 277 | 279 |
| H1H9351P2 | 289 | 291 | 293 | 295 | 273 | 275 | 277 | 279 |
| H1H9354P2 | 297 | 299 | 301 | 303 | 273 | 275 | 277 | 279 |
| H1H9364P2 | 305 | 307 | 309 | 311 | 273 | 275 | 277 | 279 |
| H1H9373P2 | 313 | 315 | 317 | 319 | 273 | 275 | 277 | 279 |
| H1H9382P2 | 321 | 323 | 325 | 327 | 273 | 275 | 277 | 279 |
| H1H9387P2 | 329 | 331 | 333 | 335 | 273 | 275 | 277 | 279 |
| H1H9396P2 | 337 | 339 | 341 | 343 | 273 | 275 | 277 | 279 |

Antibodies are typically referred to herein according to the following nomenclature: Fc prefix (e.g. "H1H," "H2M," "H2aM," etc.), followed by a numerical identifier (e.g. "8306," "9323," etc., as shown in Table 1), followed by a "P," "N," "P2," or "N2" suffix. Thus, according to this nomenclature, an antibody may be referred to herein as, e.g., "H2M8306N," "H1H9344P2," etc. The H1H, H2M and H2aM prefixes on the antibody designations used herein indicate the particular Fc region isotype of the antibody. For example, an "H1H" antibody has a human IgG1 Fc, an "H1M" antibody has a mouse IgG1 Fc, and an "H2M" or "H2aM" antibody has a mouse IgG2 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties to antigen are expected to be identical or substantially similar regardless of the nature of the Fc domain.

Example 3: Antibody Binding to PD-L1 as Determined by Surface Plasmon Resonance Binding association and dissociation rate constants ($k_a$ and $k_d$, respectively), equilibrium dissociation constants and dissociation half-lives ($K_D$ and $t_{1/2}$, respectively) of antigen binding to purified anti-PD-L1 monoclonal antibodies were determined using a real-time surface plasmon resonance biosensor assay on a Biacore 4000 instrument. The Biacore sensor surface was either derivatized with polyclonal rabbit anti-mouse antibody (GE, # BR-1008-38) or with monoclonal mouse anti-human Fc antibody (GE, # BR-1008-39) to capture approximately 200-300 RUs of anti-PD-L1 monoclonal antibodies, expressed with either a mouse Fc or with human Fc, respectively. The PD-L1 reagents tested for binding to the anti-PD-L1 antibodies included recombinant human PD-L1 (amino acids 19-239 of accession number NP_054862.1) expressed with a C-terminal myc-myc-hexahistidine tag (hPD-L1-MMH; SEQ ID: 345), recombinant cynomolgus monkey PD-L1 expressed with a C-terminal myc-myc-hexahistidine tag (MfPD-L1-MMH; SEQ ID: 346), recombinant human PD-L1 (amino acids 19-239 of accession number NP_054862.1) expressed with either a C-terminal human IgG1 Fc tag (hPD-L1-hFc; SEQ ID: 347) or with a C-terminal mouse IgG2a Fc tag (hPD-L1-mFc; SEQ ID: 348), and recombinant cynomolgus monkey PD-L1 expressed with a C-terminal mouse IgG2a Fc tag (MfPD-L1-mFc; SEQ ID: 353). Different concentrations of PD-L1 reagents were injected over the anti-PD-L1 monoclonal antibody captured surface at a flow rate of 30 μL/min. The binding of the PD-L1 reagents to the captured monoclonal antibodies was monitored for 3 to 4 minutes while the dissociation of antibody bound PD-L1 reagents was monitored for 10 minutes in HBST running buffer (0.01 M HEPES pH 7.4, 0.15 M NaCl, 3 mM EDTA, 0.05% v/v Surfactant tween-20). Experiments were performed at either 25° C. or 37° C. Kinetic association ($k_a$) and dissociation ($k_d$) rate constants were determined by processing and fitting the data to a 1:1 binding model using Scrubber 2.0c curve fitting software. Binding dissociation equilibrium constants ($K_D$) and dissociative half-lives ($t_{1/2}$) were then calculated from the kinetic rate constants as: $K_D$ (M)=$k_d/k_a$ and $t_{1/2}$ (min)=[ln 2/(60*$k_d$)]. Binding kinetics parameters for different anti-PD-L1 monoclonal antibodies binding to different PD-L1 reagents at 25° C. and 37° C. are tabulated in Tables 3-8.

TABLE 3

Binding Kinetics parameters of anti-PD-L1 monoclonal antibodies binding to hPD-L1-MMH at 25° C.
hPD-L1-MMH Monomer Binding at 25° C.

| Antibody | $k_a$ (1/Ms) | $k_d$ (1/s) | $K_D$ (M) | $t^{1/2}$ (min) |
|---|---|---|---|---|
| H2aM8306N | 1.44E+05 | 1.00E−02 | 6.96E−08 | 1.2 |
| H2aM8307N | 3.27E+04 | 1.47E−04 | 4.50E−09 | 79 |
| H2aM8309N | 6.42E+05 | 1.04E−02 | 1.63E−08 | 1.1 |
| H2aM8310N | 8.86E+04 | 3.10E−04 | 3.50E−09 | 37 |
| H2aM8312N | 7.59E+04 | 7.22E−04 | 9.51E−09 | 16 |
| H2aM8314N | 9.25E+04 | 5.17E−05 | 5.58E−11 | 224 |
| H2aM8316N | 9.57E+05 | 1.12E−03 | 1.17E−09 | 10 |
| H2aM8317N | 9.40E+04 | 3.95E−02 | 4.21E−07 | 0.3 |
| H2aM8321N | 1.03E+05 | 3.59E−03 | 3.49E−08 | 3.2 |
| H2aM8323N | 9.37E+05 | 2.23E−04 | 2.38E−10 | 52 |
| H2aM8718N | 9.27E+05 | 8.01E−05 | 8.63E−11 | 144 |
| H2aM8719N | 8.64E+04 | 2.26E−03 | 2.62E−08 | 5.1 |
| H1H9323P | 5.51E+04 | 1.88E−02 | 3.41E−07 | 0.6 |
| H1H9327P | 4.19E+05 | 2.59E−04 | 6.19E−10 | 45 |
| H1H9329P | 1.77E+06 | 1.34E−01 | 7.58E−08 | 0.1 |
| H1H9336P | 7.92E+05 | 3.90E−04 | 4.92E−10 | 30 |
| H1H9345P2 | 9.02E+04 | 1.49E−02 | 1.65E−07 | 0.8 |
| H1H9351P2 | 4.56E+05 | 8.96E−04 | 1.96E−09 | 13 |
| H1H9354P2 | 4.76E+05 | 3.83E−04 | 8.04E−10 | 30 |
| H1H9364P2 | 9.32E+05 | 2.99E−04 | 3.21E−10 | 39 |
| H1H9373P2 | 2.65E+06 | 2.91E−04 | 1.10E−10 | 40 |
| H1H9382P2 | 7.90E+04 | 4.79E−03 | 6.06E−08 | 2.4 |
| H1H9387P2 | 2.64E+06 | 5.82E−02 | 2.21E−08 | 0.2 |
| H1H9396P2 | 1.72E+05 | 2.18E−03 | 1.27E−08 | 5.3 |

TABLE 4

Binding Kinetics parameters of anti-PD-L1 monoclonal antibodies binding to hPD-L1-MMH at 37° C.
hPD-L1-MMH Monomer Binding at 37° C.

| Antibody | $k_a$ (1/Ms) | $k_d$ (1/s) | $K_D$ (M) | $t^{1/2}$ (min) |
|---|---|---|---|---|
| H2aM8306N | 1.80E+05 | 3.10E−02 | 1.72E−07 | 0.4 |
| H2aM8307N | 5.35E+04 | 8.79E−04 | 1.64E−08 | 13 |
| H2aM8309N | 1.06E+06 | 3.14E−02 | 2.97E−08 | 0.4 |
| H2aM8310N | 1.32E+05 | 1.28E−03 | 9.70E−09 | 9.0 |
| H2aM8312N | 8.89E+04 | 4.03E−03 | 4.53E−08 | 2.9 |

TABLE 4-continued

Binding Kinetics parameters of anti-PD-L1 monoclonal antibodies binding to hPD-L1-MMH at 37° C.
hPD-L1-MMH Monomer Binding at 37° C.

| Antibody | $k_a$ (1/Ms) | $k_d$ (1/s) | $K_D$ (M) | $t^{1/2}$ (min) |
|---|---|---|---|---|
| H2aM8314N | 1.07E+06 | 1.50E−04 | 1.40E−10 | 77 |
| H2aM8316N | 1.01E+06 | 5.30E−03 | 5.24E−09 | 2.2 |
| H2aM8317N | 9.03E+04 | 5.85E−02 | 6.47E−07 | 0.2 |
| H2aM8321N | 1.01E+05 | 9.29E−03 | 9.16E−08 | 1.2 |
| H2aM8323N | 1.38E+06 | 6.84E−04 | 4.97E−10 | 17 |
| H2aM8718N | 1.08E+06 | 1.55E−04 | 1.44E−10 | 74 |
| H2aM8719N | 1.50E+05 | 5.76E−03 | 3.84E−08 | 2.0 |
| H1H9323P | 1.21E+05 | 4.25E−02 | 3.52E−07 | 0.3 |
| H1H9327P | 5.21E+05 | 4.29E−04 | 8.24E−10 | 27 |
| H1H9329P | 2.82E+06 | 3.29E−01 | 1.17E−07 | 0.04 |
| H1H9336P | 1.07E+06 | 7.88E−04 | 7.33E−10 | 15 |
| H1H9345P2 | 1.72E+05 | 3.40E−02 | 1.97E−07 | 0.3 |
| H1H9351P2 | 6.82E+05 | 1.68E−03 | 2.47E−09 | 6.9 |
| H1H9354P2 | 7.39E+04 | 1.14E−03 | 1.54E−08 | 10 |
| H1H9364P2 | 1.35E+06 | 5.63E−04 | 4.17E−10 | 21 |
| H1H9373P2 | 3.09E+06 | 5.58E−04 | 1.80E−10 | 21 |
| H1H9382P2 | 9.97E+04 | 1.07E−02 | 1.07E−07 | 1.1 |
| H1H9387P2 | 3.49E+06 | 1.37E−01 | 3.91E−08 | 0.08 |
| H1H9396P2 | 3.44E+05 | 1.13E−02 | 3.30E−08 | 1.0 |

TABLE 5

Binding Kinetics parameters of anti-PD-L1 monoclonal antibodies binding to human PD-L1 Dimer at 25° C.
Human PD-L1 Dimer Binding at 25° C.

| Antibody | $k_a$ (1/Ms) | $k_d$ (1/s) | $K_D$ (M) | $t^{1/2}$ (min) |
|---|---|---|---|---|
| H2aM8306N | 7.39E+05 | 3.09E−04 | 4.18E−10 | 37 |
| H2aM8307N | 1.89E+04 | 2.89E−05 | 1.54E−09 | 399 |
| H2aM8309N | 3.36E+06 | 1.44E−04 | 4.29E−11 | 80 |
| H2aM8310N | 3.13E+05 | 5.71E−05 | 1.83E−10 | 202 |
| H2aM8312N | 2.47E+05 | 1.02E−04 | 4.13E−10 | 113 |
| H2aM8314N | 3.16E+06 | 1.35E−05 | 4.26E−12 | 859 |
| H2aM8316N | 3.08E+06 | 1.44E−04 | 4.68E−11 | 80 |
| H2aM8317N | 3.59E+05 | 4.50E−04 | 1.25E−09 | 26 |
| H2aM8321N | 8.13E+05 | 2.87E−04 | 3.53E−10 | 40 |
| H2aM8323N | 2.91E+06 | 2.05E−05 | 7.04E−12 | 565 |
| H2aM8718N | 3.20E+06 | 1.62E−05 | 5.06E−12 | 713 |
| H2aM8719N | 3.42E+05 | 2.62E−04 | 7.67E−10 | 44 |
| H1H9323P | 2.24E+05 | 1.69E−04 | 7.54E−10 | 68 |
| H1H9327P | 4.66E+05 | 7.87E−05 | 1.69E−10 | 147 |
| H1H9329P | 2.97E+06 | 7.68E−04 | 2.59E−10 | 15 |
| H1H9336P | 1.38E+06 | 1.09E−04 | 7.86E−11 | 106 |
| H1H9345P2 | 5.00E+05 | 2.37E−04 | 4.74E−10 | 49 |
| H1H9351P2 | 9.16E+05 | 1.53E−04 | 1.67E−10 | 76 |
| H1H9354P2 | 1.68E+05 | 1.16E−04 | 6.89E−10 | 100 |
| H1H9364P2 | 2.42E+06 | 1.06E−04 | 4.37E−11 | 109 |
| H1H9373P2 | 4.08E+06 | 1.06E−04 | 2.60E−11 | 109 |
| H1H9382P2 | 2.23E+05 | 1.48E−04 | 6.63E−10 | 78 |
| H1H9387P2 | 5.07E+06 | 2.17E−04 | 4.27E−11 | 53 |
| H1H9396P2 | 7.76E+05 | 1.90E−04 | 2.45E−10 | 61 |

TABLE 6

Binding Kinetics parameters of anti-PD-L1 monoclonal antibodies binding to human PD-L1 Dimer at 37° C.
Human PD-L1 Dimer Binding at 37° C.

| Antibody | $k_a$ (1/Ms) | $k_d$ (1/s) | $K_D$ (M) | $t^{1/2}$ (min) |
|---|---|---|---|---|
| H2aM8306N | 9.97E+05 | 4.16E−04 | 4.17E−10 | 28 |
| H2aM8307N | 4.41E+04 | 2.21E−04 | 5.00E−09 | 52 |
| H2aM8309N | 4.41E+06 | 1.66E−04 | 3.76E−11 | 70 |
| H2aM8310N | 4.81E+05 | 1.24E−04 | 2.58E−10 | 93 |
| H2aM8312N | 3.57E+05 | 2.61E−04 | 7.32E−10 | 44 |

TABLE 6-continued

Binding Kinetics parameters of anti-PD-L1 monoclonal
antibodies binding to human PD-L1 Dimer at 37° C.
Human PD-L1 Dimer Binding at 37° C.

| Antibody | $k_a$ (1/Ms) | $k_d$ (1/s) | $K_D$ (M) | t½ (min) |
|---|---|---|---|---|
| H2aM8314N | 3.89E+06 | 2.30E-05 | 5.91E-12 | 503 |
| H2aM8316N | 4.06E+06 | 2.37E-04 | 5.85E-11 | 49 |
| H2aM8317N | 4.81E+05 | 6.57E-04 | 1.36E-09 | 18 |
| H2aM8321N | 9.46E+05 | 2.69E-04 | 2.85E-10 | 43 |
| H2aM8323N | 4.32E+06 | 1.21E-04 | 2.80E-11 | 96 |
| H2aM8718N | 3.72E+06 | 1.98E-05 | 5.32E-12 | 584 |
| H2aM8719N | 4.37E+05 | 2.91E-04 | 6.66E-10 | 40 |
| H1H9323P | 5.19E+05 | 2.03E-04 | 3.91E-10 | 57 |
| H1H9327P | 6.83E+05 | 1.36E-04 | 2.00E-10 | 85 |
| H1H9329P | 3.87E+06 | 2.67E-03 | 6.89E-10 | 4.3 |
| H1H9336P | 2.75E+06 | 8.31E-05 | 3.02E-11 | 139 |
| H1H9345P2 | 6.82E+05 | 2.03E-04 | 2.97E-10 | 57 |
| H1H9351P2 | 1.25E+06 | 1.46E-04 | 1.17E-10 | 79 |
| H1H9354P2 | 4.56E+05 | 1.45E-04 | 3.17E-10 | 80 |
| H1H9364P2 | 3.34E+06 | 6.96E-05 | 2.08E-11 | 166 |
| H1H9373P2 | 5.12E+06 | 8.97E-05 | 1.75E-11 | 129 |
| H1H9382P2 | 4.92E+05 | 1.37E-04 | 2.78E-10 | 84 |
| H1H9387P2 | 6.12E+06 | 3.92E-04 | 6.39E-11 | 29 |
| H1H9396P2 | 1.09E+06 | 2.58E-04 | 2.37E-10 | 45 |

TABLE 7

Binding Kinetics parameters of anti-PD-L1 monoclonal
antibodies binding to MfPD-L1-MMH at 25° C.
MfPD-L1-MMH Monomer Binding at 25° C.

| Antibody | $k_a$ (1/Ms) | $k_d$ (1/s) | $K_D$ (M) | t½ (min) |
|---|---|---|---|---|
| H2aM8306N | 1.65E+05 | 7.88E-03 | 4.77E-08 | 1.5 |
| H2aM8307N | 2.61E+04 | 1.07E-03 | 4.09E-08 | 11 |
| H2aM8309N | 8.70E+05 | 1.30E-02 | 1.49E-08 | 0.9 |
| H2aM8310N | 1.03E+05 | 3.06E-04 | 2.97E-09 | 38 |
| H2aM8312N | 7.09E+04 | 5.97E-04 | 8.42E-09 | 19 |
| H2aM8314N | 9.66E+05 | 7.00E-05 | 7.24E-11 | 165 |
| H2aM8316N | 9.71E+05 | 1.64E-03 | 1.69E-09 | 7.0 |
| H2aM8317N | 1.06E+05 | 2.38E-02 | 2.26E-07 | 0.5 |
| H2aM8321N | 1.34E+05 | 4.02E-03 | 2.99E-08 | 2.9 |
| H2aM8323N | 5.47E+05 | 8.68E-03 | 1.59E-08 | 1.3 |
| H2aM8718N | 9.04E+05 | 6.64E-05 | 7.35E-11 | 174 |
| H2aM8719N | 8.17E+04 | 2.68E-03 | 3.28E-08 | 4.3 |
| H1H9323P | 8.22E+04 | 2.40E-02 | 2.92E-07 | 0.5 |
| H1H9327P | 3.59E+05 | 3.33E-04 | 9.28E-10 | 35 |
| H1H9329P | 1.76E+06 | 1.35E-01 | 7.69E-08 | 0.09 |
| H1H9336P | 6.79E+05 | 5.94E-04 | 8.76E-10 | 19 |
| H1H9345P2 | 1.10E+05 | 8.50E-03 | 7.73E-08 | 1.4 |
| H1H9351P2 | 3.49E+05 | 1.11E-03 | 3.19E-09 | 10 |
| H1H9354P2 | 4.60E+04 | 3.05E-04 | 6.64E-09 | 38 |
| H1H9364P2 | 7.57E+05 | 3.12E-04 | 4.12E-10 | 37 |
| H1H9373P2 | 2.21E+06 | 2.82E-04 | 1.27E-10 | 41 |
| H1H9382P2 | 8.22E+04 | 1.29E-02 | 1.57E-07 | 0.9 |
| H1H9387P2 | 2.37E+06 | 6.04E-02 | 2.55E-08 | 0.2 |
| H1H9396P2 | 2.06E+05 | 2.52E-03 | 1.22E-08 | 4.6 |

TABLE 8

Binding Kinetics parameters of anti-PD-L1 monoclonal
antibodies binding to MfPD-L1-MMH at 37° C.
MfPD-L1-MMH Monomer Binding at 37° C.

| Antibody | $k_a$ (1/Ms) | $k_d$ (1/s) | $K_D$ (M) | t½ (min) |
|---|---|---|---|---|
| H2aM8306N | 2.74E+05 | 3.68E-02 | 1.34E-07 | 0.3 |
| H2aM8307N | 1.87E+05 | 1.43E-03 | 7.63E-09 | 8.1 |
| H2aM8309N | 1.07E+06 | 2.81E-02 | 2.63E-08 | 0.4 |
| H2aM8310N | 4.71E+05 | 1.07E-03 | 2.27E-09 | 11 |
| H2aM8312N | 1.01E+05 | 3.32E-03 | 3.27E-08 | 3.5 |

TABLE 8-continued

Binding Kinetics parameters of anti-PD-L1 monoclonal
antibodies binding to MfPD-L1-MMH at 37° C.
MfPD-L1-MMH Monomer Binding at 37° C.

| Antibody | $k_a$ (1/Ms) | $k_d$ (1/s) | $K_D$ (M) | t½ (min) |
|---|---|---|---|---|
| H2aM8314N | 1.07E+06 | 1.52E-04 | 1.42E-10 | 76 |
| H2aM8316N | 1.02E+06 | 5.38E-03 | 5.27E-09 | 2.1 |
| H2aM8317N | 2.66E+05 | 4.76E-02 | 1.79E-07 | 0.2 |
| H2aM8321N | 1.59E+05 | 8.16E-03 | 5.11E-08 | 1.4 |
| H2aM8323N | 9.56E+05 | 2.82E-02 | 2.95E-08 | 0.4 |
| H2aM8718N | 1.10E+06 | 1.46E-04 | 1.33E-10 | 79 |
| H2aM8719N | 1.35E+05 | 6.99E-03 | 5.19E-08 | 1.7 |
| H1H9323P | 1.25E+05 | 4.99E-02 | 3.98E-07 | 0.2 |
| H1H9327P | 4.77E+05 | 5.34E-04 | 1.12E-09 | 22 |
| H1H9329P | 2.66E+06 | 3.64E-01 | 1.37E-07 | 0.03 |
| H1H9336P | 9.09E+05 | 1.25E-03 | 1.38E-09 | 9.2 |
| H1H9345P2 | 1.64E+05 | 1.97E-02 | 1.21E-07 | 0.6 |
| H1H9351P2 | 5.60E+05 | 2.01E-03 | 3.59E-09 | 5.8 |
| H1H9354P2 | 8.59E+04 | 8.44E-04 | 9.82E-09 | 14 |
| H1H9364P2 | 1.12E+06 | 6.33E-04 | 5.66E-10 | 18 |
| H1H9373P2 | 2.81E+06 | 5.69E-04 | 2.03E-10 | 20 |
| H1H9382P2 | 1.30E+05 | 2.45E-02 | 1.89E-07 | 0.5 |
| H1H9387P2 | 3.20E+06 | 1.57E-01 | 4.89E-08 | 0.07 |
| H1H9396P2 | 3.94E+05 | 1.20E-02 | 3.05E-08 | 1.0 |

TABLE 9

Binding Kinetics parameters of anti-PD-L1 monoclonal
antibodies binding to monkey PD-L1-mFc at 25° C.
MfPD-L1-mFc Binding at 25° C.

| Antibody | $k_a$ (1/Ms) | $k_d$ (1/s) | $K_D$ (M) | t½ (min) |
|---|---|---|---|---|
| H1H8314N | 2.58E+06 | 6.77E-05 | 2.63E-11 | 171 |
| H1H8316N | 2.71E+06 | 5.23E-05 | 1.93E-11 | 221 |
| H1H8323N | 2.67E+06 | 6.16E-05 | 2.31E-11 | 188 |
| H1H9351P2 | 7.81E+05 | 7.19E-05 | 9.22E-11 | 161 |
| H1H9364P2 | 1.32E+06 | 7.75E-05 | 5.87E-11 | 149 |
| H1H9373P2 | 2.85E+06 | 4.96E-05 | 1.74E-11 | 233 |
| H1H9387P2 | 3.55E+06 | 1.61E-04 | 4.52E-11 | 72 |
| H1H9351P2 | 8.64E+05 | 7.80E-05 | 9.03E-11 | 148 |
| H1H9364P2 | 1.25E+06 | 5.80E-05 | 4.62E-11 | 199 |
| H1H9373P2 | 3.27E+06 | 6.55E-05 | 2.00E-11 | 176 |
| H1H9387P2 | 2.90E+06 | 2.12E-04 | 7.30E-11 | 55 |
| H1H9323P | 2.80E+05 | 1.45E-04 | 5.19E-10 | 79 |
| H1H9327P | 3.48E+05 | 1.02E-04 | 2.94E-10 | 113 |
| H1H9329P | 1.74E+06 | 6.72E-04 | 3.86E-10 | 17 |
| H1H9336P | 9.90E+05 | 6.16E-05 | 6.22E-11 | 188 |
| H1H9344P2 | 3.50E+05 | 1.38E-04 | 3.93E-10 | 84 |
| H1H9345P2 | 2.96E+05 | 1.51E-04 | 5.12E-10 | 76 |
| H1H9354P2 | 2.05E+05 | 9.14E-05 | 4.47E-10 | 126 |
| H1H9382P2 | 2.13E+05 | 1.33E-04 | 6.26E-10 | 87 |
| H1H9396P2 | 8.37E+05 | 1.88E-04 | 2.25E-10 | 61 |

TABLE 10

Binding Kinetics parameters of anti-PD-L1 monoclonal
antibodies binding to monkey PD-L1-mFc at 37° C.
MfPD-L1-mFc Binding at 37° C.

| Antibody | $k_a$ (1/Ms) | $k_d$ (1/s) | $K_D$ (M) | t½ (min) |
|---|---|---|---|---|
| H1H8314N | 2.89E+06 | 9.60E-05 | 3.33E-11 | 120 |
| H1H8316N | 2.96E+06 | 6.16E-05 | 2.08E-11 | 187 |
| H1H8323N | 2.99E+06 | 1.35E-04 | 4.51E-11 | 86 |
| H1H9351P2 | 1.06E+06 | 9.46E-05 | 8.91E-11 | 122 |
| H1H9364P2 | 2.36E+06 | 1.11E-04 | 4.71E-11 | 104 |
| H1H9373P2 | 3.15E+06 | 8.59E-05 | 2.73E-11 | 134 |
| H1H9387P2 | 3.41E+06 | 4.74E-04 | 1.39E-10 | 24 |
| H1H9351P2 | 1.61E+06 | 1.04E-04 | 6.47E-11 | 111 |
| H1H9364P2 | 2.41E+06 | 6.76E-05 | 2.80E-11 | 171 |

TABLE 10-continued

Binding Kinetics parameters of anti-PD-L1 monoclonal
antibodies binding to monkey PD-L1-mFc at 37° C.
MfPD-L1-mFc Binding at 37° C.

| Antibody | $k_a$ (1/Ms) | $k_d$ (1/s) | $K_D$ (M) | t½ (min) |
|---|---|---|---|---|
| H1H9373P2 | 3.86E+06 | 1.23E−04 | 3.19E−11 | 94 |
| H1H9387P2 | 2.90E+06 | 4.65E−04 | 1.61E−10 | 25 |
| H1H9323P | 3.84E+05 | 2.44E−04 | 6.36E−10 | 47 |
| H1H9327P | 7.64E+05 | 2.94E−04 | 3.85E−10 | 39 |
| H1H9329P | 2.18E+06 | 1.54E−03 | 7.08E−10 | 8 |
| H1H9336P | 1.86E+06 | 4.60E−05 | 2.47E−11 | 251 |
| H1H9344P2 | 9.05E+05 | 2.17E−04 | 2.40E−10 | 53 |
| H1H9345P2 | 8.61E+05 | 2.92E−04 | 3.39E−10 | 40 |
| H1H9354P2 | 2.72E+05 | 2.03E−04 | 7.46E−10 | 57 |
| H1H9382P2 | 2.84E+05 | 2.35E−04 | 8.25E−10 | 49 |
| H1H9396P2 | 1.57E+06 | 5.02E−04 | 3.19E−10 | 23 |

As shown in Table 3, at 25° C., all 25 anti-PD-L1 antibodies of the invention bound to hPD-L1-MMH with $K_D$ values ranging from 55.8 pM to 421 nM. As shown in Table 4, at 37° C., all 25 anti-PD-L1 antibodies of the invention bound to hPD-L1-MMH with $K_D$ values ranging from 140 pM to 647 nM. As shown in Table 5, at 25° C., all 25 anti-PD-L1 antibodies of the invention bound to hPD-L1 dimer with $K_D$ values ranging from 4.26 pM to 1.54 nM. As shown in Table 6, at 37° C., all 25 anti-PD-L1 antibodies of the invention bound to hPD-L1 dimer with $K_D$ values ranging from 5.32 pM to 5.0 nM. As shown in Table 7, at 25° C., all 25 anti-PD-L1 antibodies of the invention bound to MfPD-L1-MMH with $K_D$ values ranging from 72.4 pM to 292 nM. As shown in Table 8, at 37° C., all 25 anti-PD-L1 antibodies of the invention bound to MfPD-L1-MMH with $K_D$ values ranging from 133 pM to 398 nM. As shown in Table 9, at 25° C., all 20 anti-PD-L1 antibodies of the invention tested bound to MfPD-L1-mFc with $K_D$ values ranging from 17.4 pM to 626 pM. As shown in Table 10, at 37° C., all 20 anti-PD-L1 antibodies of the invention tested bound to MfPD-L1-mFc with $K_D$ values ranging from 20.8 pM to 825 pM.

Example 4: Blocking of PD-L1 Binding to PD-1 as Determined by ELISA

The ability of monoclonal anti-PD-L1 antibodies to block human PD-L1 from binding to its binding partners, the human PD-1 and the human B7-1 receptors, was measured using two competition sandwich ELISA formats.

A dimeric human PD-1 protein comprised of a portion of the extracellular domain (amino acids 25-170 of accession number NP_005009.2 with a C93S change) that was expressed with a C-terminal hFc tag (hPD-1-hFc; SEQ ID: 350) and a dimeric human B7-1 protein comprised of a portion of the extracellular domain expressed with C-terminal hFc tag and hexahistidine tags (hB7-1-hFc-6His; R&D Systems, #140-B1) were separately coated at 2 μg/mL on a 96-well microtiter plate in a PBS buffer overnight at 4° C. Nonspecific binding sites were subsequently blocked using a 0.5% (w/v) solution of BSA in PBS. A constant amount of 0.5 nM or 8.0 nM of a dimeric hPD-L1 protein comprised of a portion of the human PD-L1 extracellular domain that was expressed with a C-terminal mFc tag (hPD-L1-mFc; SEQ ID: 348) was separately titrated with concentrations of anti-PD-1 antibodies and isotype control antibodies ranging between 0-210 nM in serial dilution. These antibody-protein complexes were then incubated for 1 hour at room temperature (RT). Complexes with 0.5 nM constant hPD-L1-mFc were subsequently transferred to microtiter plates coated with hPD-1-hFc, and complexes with 8 nM constant hPD-L1-mFc were transferred to hB7-1-hFc-6His coated plates. The complexes were allowed to bind to the coated plates for 1 hour at RT. After the 1 hour incubation, the wells were washed and plate-bound hPD-L1-mFc was detected with an anti-mFc polyclonal antibody conjugated with horse-radish peroxidase (Jackson ImmunoResearch, #115-035-164). Samples were developed with a TMB solution (BD Biosciences, #51-2606KC and #51-2607KC) to produce a colorimetric reaction and neutralized with 1M sulfuric acid before measuring absorbance at 450 nm on a Victor X5 plate reader. Data analysis used a sigmoidal dose-response model within Prism™ software. The calculated $IC_{50}$ value, defined as the concentration of antibody required to block 50% of hPD-L1-mFc binding to hPD-1-hFc or hB7-1-hFc-6His, was used as an indicator of blocking potency. Maximum blocking values represent the ability of the antibodies to block hPD-L1-mFc binding relative to baseline. The absorbance measured at the constant amount of hPD-L1 on the dose curve is defined as 0% blocking and the absorbance with no added hPD-L1 is defined as 100% blocking. The absorbance values of the wells containing the highest concentration for each antibody were used to determine the blocking percent at maximum concentration antibody tested. Antibodies with a maximum percent blockade below 25% were characterized as non-blockers, and their $IC_{50}$ values were not reported in Table 11. Antibodies with a maximum percent blockade below −25% were characterized as non-blockers/enhancers.

TABLE 11

ELISA blocking of hPD-L1-mFc binding to hPD-1-hFc and hB7-1-hFc-6His by anti-PD-L1 antibodies

| Antibody | Highest Antibody concentration (nM) tested on hPD-1-hFc coat | Blocking 0.5 nM of hPD-L1-mFc binding to hPD-1-hFc, $IC_{50}$ (A) | Blocking 0.5 nM of hPD-L1-mFc binding to hPD-1-hFc, % maximum blocking | Highest Antibody concentration (nM) tested on hB7-1-hFc-6His coat | Blocking 8 nM of hPD-L1-mFc binding to hB7-1-hFc-6His, $IC_{50}$ (M) | Blocking 8 nM of hPD-L1-mFc binding to hB7-1-hFc-6His, % maximum blocking |
|---|---|---|---|---|---|---|
| H2aM8306N | 50 | <2.5E−10 (*) | 99 | 150 | <4.0E−09 (*) | 93 |
| H2aM8307N | 50 | IC | 29 | 150 | NBl/enhancer | −44 |
| H2aM8309N | 50 | <2.5E−10 (*) | 98 | 150 | <4.0E−09 (*) | 98 |
| H2aM8310N | 50 | 3.9E−10 | 76 | 150 | <4.0E−09 (*) | 98 |
| H2aM8312N | 50 | NBl | 23 | 150 | <4.0E−09 (*) | 98 |
| H2aM8314N | 50 | <2.5E−10 (*) | 93 | 150 | <4.0E−09 (*) | 97 |

TABLE 11-continued

ELISA blocking of hPD-L1-mFc binding to hPD-1-hFc and hB7-1-hFc-6His by anti-PD-L1 antibodies

| Antibody | Highest Antibody concentration (nM) tested on hPD-1-hFc coat | Blocking 0.5 nM of hPD-L1-mFc binding to hPD-1-hFc, IC$_{50}$ (A) | Blocking 0.5 nM of hPD-L1-mFc binding to hPD-1-hFc, % maximum blocking | Highest Antibody concentration (nM) tested on hB7-1-hFc-6His coat | Blocking 8 nM of hPD-L1-mFc binding to hB7-1-hFc-6His, IC$_{50}$ (M) | Blocking 8 nM of hPD-L1-mFc binding to hB7-1-hFc-6His, % maximum blocking |
|---|---|---|---|---|---|---|
| H2aM8316N | 50 | <2.5E−10 (*) | 96 | 150 | <4.0E−09 (*) | 98 |
| H2aM8317N | 50 | NBl | −11 | 150 | NBl/enhancer | −166 |
| H2aM8321N | 50 | NBl | 10 | 150 | NBl/enhancer | −124 |
| H2aM8323N | 50 | <2.5E−10 (*) | 100 | 150 | <4.0E−09 (*) | 99 |
| H2aM8718N | 50 | <2.5E−10 (*) | 97 | 150 | 1.0E−08 | 57 |
| H2aM8719N | 50 | 7.7E−10 | 95 | 150 | NBl/enhancer | −50 |
| H1H9323P | 50 | <2.5E−10 (*) | 43 | 210 | NBl/enhancer | −25 |
| H1H9327P | 50 | NBl/enhancer | −28 | 210 | IC | 41 |
| H1H9329P | 50 | <2.5E−10 (*) | 100 | 210 | 4.9E−09 | 100 |
| H1H9336P | 50 | <2.5E−10 (*) | 100 | 210 | 4.4E−09 | 99 |
| H1H9344P2 | 50 | NBl | 15 | 210 | NBl/enhancer | −51 |
| H1H9345P2 | 50 | <2.5E−10 (*) | 26 | 210 | NBl/enhancer | −34 |
| H1H9351P2 | 50 | <2.5E−10 (*) | 100 | 210 | 4.4E−09 | 100 |
| H1H9354P2 | 50 | 5.3E−10 | 34 | 210 | NBl | −13 |
| H1H9364P2 | 50 | <2.5E−10 (*) | 100 | 210 | 4.1E−09 | 101 |
| H1H9373P2 | 50 | <2.5E−10 (*) | 100 | 210 | 4.6E−09 | 101 |
| H1H9382P2 | 50 | <2.5E−10 (*) | 39 | 210 | NBl/enhancer | −30 |
| H1H9387P2 | 50 | <2.5E−10 (*) | 100 | 210 | <4.0E−09 (*) | 100 |
| H1H9396P2 | 50 | <2.5E−10 (*) | 59 | 210 | NBl | 8 |
| Isotype control-human IgG1 | 50 | NBl | −11 | 210 | NBl | −3 |
| Isotype control-mouse IgG2a | 50 | NBl | 5 | 210 | NBl | −3 |

(*) - below theoretical bottom of the assay; Assay theoretical bottom is 2.5E−10M for hPD-1-hFc coat and 4.0E−09M for hB7-1-hFc-6His coat;
NBl—non-blocker;
IC—inconclusive As shown in Table 11, 19 of the 25 anti-PD-L1 antibodies of the invention blocked 0.5 nM of hPD-L1-mFc from binding to hPD-1-hFc with IC$_{50}$ values ranging from less than 250 pM to 770 pM with maximum percent blockade ranging from 26% to 100%. Four of the 25 anti-PD-L1 antibodies tested were characterized as non-blockers of hPD-L1-mFc binding to hPD-1-hFc, while one antibody tested (H1H9327P) was characterized as a non-blocker/enhancer of hPD-L1-mFc binding to hPD-1-hFc. One antibody (H2aM8307N) demonstrated weak blocking of hPD-L1-mFc binding to hPD-1-hFc with a maximum percent blockade of 29%; however the IC$_{50}$ value could not be determined for this sample.

Further, 14 of the 25 anti-PD-L1 antibodies of the invention blocked 8 nM of hPD-L1-mFc from binding to hB7-1-hFc-6His with IC$_{50}$ values ranging from <4 nM to 10 nM with maximum percent blockade ranging from 57% to 101%. Two of the 25 anti-PD-L1 antibodies tested were characterized as non-blockers of hPD-L1-mFc binding to hB7-1-hFc-6His, while 8 antibodies tested were characterized as non-blockers/enhancers of hPD-L1-mFc binding to hB7-1-hFc-6His. One antibody (H1H9327P) demonstrated weak blocking of hPD-L1-mFc binding to hB7-1-hFc-6His with a maximum percent blockade of 41%; however the IC$_{50}$ value could not be determined for this sample.

Example 5: Blocking of PD-L1 Binding to PD-1 as Determined by Biosensor Assay and by Surface Plasmon Resonance Inhibition of human PD-L1 from binding to human PD-1 by different anti-PD-L1 monoclonal antibodies was studied either using real time bio-layer interferometry assay on an Octet Red96 biosensor instrument (Fortebio Inc.) or using a real-time surface plasmon resonance biosensor assay on a Biacore 3000 instrument.

Inhibition studies for anti-PD-L1 monoclonal antibodies expressed with mouse Fc were performed on an Octet Red96 instrument. First, 100 nM of a recombinant human PD-L1 expressed with a C-terminal mouse IgG2a Fc tag (hPD-L1-mFc; SEQ ID: 348) was incubated with 500 nM of each anti-PD-L1 monoclonal antibody for at least 1 hour before running the inhibition assay. Approximately 0.8 nm to 1.2 nm of recombinant human PD-1 expressed with a C-terminal human IgG1 Fc tag (hPD-1-hFc; SEQ ID: 350) was captured using anti-human IgG Fc capture biosensors. The Octet biosensors captured with hPD-1-hFc were subsequently submerged into wells containing the mixture of hPD-L1-mFc and different anti-PD-L1 monoclonal antibodies. The entire experiment was performed at 25° C. in Octet HBST buffer (0.01 M HEPES pH7.4, 0.15M NaCl, 3 mM EDTA, 0.05% v/v Surfactant P20, 0.1 mg/mL BSA) with a plate shaking at a speed of 1000 rpm. The biosensors were washed in Octet HBST buffer in between each step of the experiment. The real-time binding response was monitored during the course of the experiment and the binding response at the end of every step was recorded. Binding of hPD-L1-mFc to the captured hPD-1-hFc was compared in the presence and absence of different anti-PD-L1 monoclonal antibodies and was used to determine the blocking behavior of the tested antibodies as shown in Table 12.

TABLE 12

Inhibition of human PD-1 binding to human PD-L1 by different anti-PD-L1 monoclonal antibodies expressed with mouse Fc performed on Octet Red96 instrument.

| Anti-PD-L1 monoclonal antibody | Amount of hPD-1-hFc Captured (nm) | Binding of the mixture of 100 nM hPD-L1-mFc and 500 nM anti-PD-L1 monoclonal antibody (nm) | % Blocking |
|---|---|---|---|
| No antibody | 1.05 | 0.31 | 0 |
| H2aM8306N | 0.98 | 0.02 | 94 |
| H2aM8307N | 1.01 | 0.46 | −48 |
| H2aM8309N | 0.89 | 0.02 | 94 |
| H2aM8310N | 0.95 | 0.13 | 58 |
| H2aM8312N | 1.06 | 0.52 | −68 |
| H2aM8314N | 0.99 | 0.02 | 94 |
| H2aM8316N | 1.06 | 0.01 | 97 |
| H2aM8317N | 0.92 | 0.58 | −87 |
| H2aM8321N | 1.04 | 0.60 | −94 |
| H2aM8323N | 1.00 | 0.02 | 94 |
| H2aM8718N | 1.08 | 0.01 | 97 |
| H2aM8719N | 0.93 | 0.11 | 65 |
| Isotype control antibody | 1.10 | 0.35 | −13 |

As shown in Table 12, 8 of the 12 anti-PD-L1 antibodies tested on the Octet Red96 instrument demonstrated blocking of hPD-L1-mFc from binding to hPD-1-hFc ranging from 58% to 97%. Four anti-PD-L1 antibodies tested demonstrated the ability to enhance the binding of hPD-L1-mFc to hPD-1-hFc.

Next, inhibition studies for anti-PD-L1 monoclonal antibodies expressed with human Fc were performed on Biacore 3000 instrument. First, 100 nM of recombinant human PD-L1 expressed with a C-terminal human IgG1 Fc tag (hPD-L1-hFc; SEQ ID: 350) was incubated with 500 nM of each anti-PD-L1 monoclonal antibody for at least 1 hour before running the inhibition assay. A CM5 Biacore sensor surface was first derivatized with anti-mouse IgG2a specific polyclonal antibody (Southern Biotech, #1080-01) using the standard EDC-NHS chemistry. Around 230 RUs of recombinant human PD-1 expressed with a C-terminal mouse IgG2a Fc tag (hPD-1-mFc; SEQ ID: 348) was then captured and was followed by an injection of 100 nM of hPD-L1-hFc in the presence and absence of different anti-PD-L1 monoclonal antibodies at a flow rate of 25 µL/min for 2 minutes. The entire experiment was performed at 25° C. in HBST running buffer (0.01 M HEPES pH7.4, 0.15M NaCl, 3 mM EDTA, 0.05% v/v Surfactant P20). The real-time binding responses were monitored during the entire course of the experiment and the binding response at the end of every step was recorded. Binding of hPD-L1-hFc to the captured hPD-1-mFc was compared in the presence and absence of different anti-PD-L1 monoclonal antibodies and was used to determine the blocking behavior of the tested antibodies as shown in Table 13.

TABLE 13

Inhibition of human PD-1 binding to human PD-L1 by different anti-PD-L1 monoclonal antibodies expressed with human Fc performed on Biacore 3000 instrument.

| Anti-PD-L1 monoclonal antibody | Amount of hPD-1-mFc Captured (RU) | Binding of the mixture of 100 nM hPD-L1-hFc and 500 nM anti-PD-L1 monoclonal antibody (nm) | % Blocking |
|---|---|---|---|
| No mAb | 222 | 56 | 0 |
| H1H9323P | 224 | 262 | −368 |
| H1H9327P | 226 | 172 | −207 |
| H1H9329P | 227 | 2 | 97 |
| H1H9336P | 227 | 9 | 84 |
| H1H9345P2 | 229 | 292 | −422 |
| H1H9351P2 | 227 | 6 | 90 |
| H1H9354P2 | 229 | 296 | −428 |
| H1H9364P2 | 228 | 8 | 86 |
| H1H9373P2 | 227 | 6 | 89 |
| H1H9382P2 | 228 | 307 | −448 |
| H1H9387P2 | 228 | 5 | 91 |
| H1H9396P2 | 228 | 164 | −193 |
| Isotype control antibody | 228 | 56 | 0 |

As shown in Table 13, 6 out of 12 anti-PD-L1 antibodies of the invention tested on the Biacore 3000 instrument demonstrated blocking of hPD-L1-hFc from binding to hPD-1-mFc ranging from 84% to 97%. Six anti-PD-L1 antibodies tested demonstrated the ability to enhance the binding of hPD-L1-hFc to hPD-1-mFc.

Example 6: Octet Cross-Competition Between Anti-PD-L1 Antibodies

Binding competition between anti-PD-L1 monoclonal antibodies was determined using a real time, label-free bio-layer interferometry assay on an Octet RED384 biosensor (Pall ForteBio Corp.). The entire experiment was performed at 25° C. in Octet HBST buffer (0.01 M HEPES pH7.4, 0.15M NaCl, 3 mM EDTA, 0.05% v/v Surfactant P20, 0.1 mg/mL BSA) with the plate shaking at the speed of 1000 rpm. To assess whether 2 antibodies were able to compete with one another for binding to their respective epitopes on the recombinant human PD-L1 expressed with a C-terminal myc-myc-hexahistidine tag (hPD-L1-MMH; SEQ ID: 345), around ~0.3 nm of hPD-L1-MMH was first captured onto anti-Penta-His antibody coated Octet biosensor tips (Fortebio Inc, #18-5079) by submerging the tips for 5 minutes into well containing 20 µg/mL solution of hPD-L1-MMH. The antigen captured biosensor tips were then saturated with first anti-PD-L1 monoclonal antibody (subsequently referred to as mAb-1) by dipping into wells containing 50 µg/mL solution of mAb-1 for 5 minutes. The biosensor tips were then subsequently dipped into wells containing 50 µg/mL solution of a second anti-PD-L1 monoclonal antibody (subsequently referred to as mAb-2). The biosensor tips were washed in Octet HBST buffer in between every step of the experiment. The real-time binding response was monitored during the course of the experiment and the binding response at the end of every step was recorded as shown in FIG. 1. The response of mAb-2 binding to hPD-L1-MMH pre-complexed with mAb-1 was compared and competitive/non-competitive behavior of different anti-PD-L1 monoclonal antibodies was determined.

Under the experimental conditions used in this Example, (a) H2aM8309N, H1H9329P, H1H9336P, H2aM8314N, H2aM8316N, H2aM8718N, H1H9387P2, H1H9351P2, H1H9364P2, H1H9373P2, and H2aM8306N cross-competed with each other; (b) H2aM8310N, H2aM8321N and H2aM8312N cross-competed with each other; (c) H1H9396P2, H2aM8317N, H2aM8321N, H1H9323P, H1H9382P2, H1H9344P2, H1H9345P2, and H1H9354P2 cross-competed with each other; and (d) H1H9327P and H2aM8307N cross-competed with each other. In one instance, competition was observed in one orientation but not in the opposite orientation: i.e., H2aM8307N when applied first competed with H2aM8309N, H1H9329P, H1H9336P, H2aM8314N, H2aM8316N, H2aM8718N, H1H9387P2, H1H9351P2, H1H9364P2, H1H9373P2, and H2aM8306N; however, in the opposite orientation, H2aM8309N, H1H9329P, H1H9336P, H2aM8314N, H2aM8316N, H2aM8718N, H1H9387P2, H1H9351P2, H1H9364P2, H1H9373P2, and H2aM8306N when applied first did not compete with H2aM8307N.

Example 7: Antibody Binding to Cells Overexpressing PD-L1

The binding of anti-PD-L1 antibodies to a human embryonic kidney cell line (HEK293; ATCC, #CRL-1573) stably transfected with full length human PD-L1 (amino acids 1 to 290 of accession number NP_054862.1) (HEK293/hPD-L1) was determined by FACS.

For the assay, adherent cells were detached using enzyme-free dissociation buffer and blocked with complete medium. Cells were centrifuged and resuspended at a concentration of $2.8 \times 10^6$ cells/mL in cold PBS containing 2% FBS. HEK293 parental and HEK293/hPD-L1 cells were then incubated for 15 to 30 minutes on ice with 100 nM of each anti-PD-L1 antibody or an isotype control antibody. Unbound antibodies were removed by washing with D-PBS containing 2% FBS, and cells were subsequently incubated with a phycoerythrin-conjugated secondary Fcγ fragment specifically recognizing either human Fc (Jackson ImmunoResearch, #109-116-170) or mouse Fc (Jackson ImmunoResearch, #115-115-164) for 15 to 30 minutes on ice. Cells were washed with D-PBS containing 2% FBS to remove unbound secondary detection reagents and fluorescence measurements were acquired using a HyperCyte (IntelliCyt, Inc.) flow cytometer. Data was analyzed using HyperCyte software.

TABLE 14

FACS binding of anti-PD-L1 antibodies to HEK293/hPD-L1 cells and parental HEK293 cells

| Antibody | FACS on HEK293 parental cells [MFI] | FACS on HEK293/ hPD-L1 cells [MFI] | Ratio of HEK293/hPD-L1 to HEK293 parental cells |
|---|---|---|---|
| H1H9323P | 1909 | 154992 | 81 |
| H1H9327P | 2120 | 317592 | 150 |
| H1H9329P | 1504 | 282088 | 188 |
| H1H9336P | 2263 | 379009 | 168 |
| H1H9344P2 | 1691 | 200976 | 119 |
| H1H9345P2 | 1885 | 228406 | 121 |
| H1H9351P2 | 1685 | 289523 | 172 |
| H1H9354P2 | 2204 | 275839 | 125 |
| H1H9364P2 | 2066 | 323663 | 157 |
| H1H9373P2 | 2151 | 333236 | 155 |
| H1H9382P2 | 1473 | 205563 | 140 |
| H1H9387P2 | 1232 | 323793 | 263 |
| H1H9396P2 | 2340 | 227961 | 97 |
| H2aM8306N | 1286 | 316485 | 246 |
| H2aM8307N | 1382 | 73976 | 54 |
| H2aM8309N | 1160 | 192678 | 166 |
| H2aM8310N | 1357 | 14918 | 11 |
| H2aM8312N | 1380 | 158331 | 115 |
| H2aM8314N | 2053 | 194832 | 95 |
| H2aM8316N | 1601 | 172104 | 108 |
| H2aM8317N | 1270 | 67600 | 53 |
| H2aM8321N | 1322 | 112495 | 85 |
| H2aM8323N | 2250 | 163497 | 73 |
| H2aM8718N | 2225 | 194341 | 87 |
| H2aM8719N | 1272 | 133399 | 105 |
| mouse IgG Isotype control | 1273 | 1115 | 0.9 |
| human IgG1 Isotype control | 1179 | 1099 | 0.9 |
| human IgG4 Isotype control | 1991 | 1839 | 0.9 |

As shown in Table 14, all 25 anti-PD-L1 antibodies of the invention showed strong binding to the HEK293/hPD-L1 cells compared to binding on the parental HEK293 line.

Example 8: Blocking of PD-L1-Induced T-Cell Down-Regulation in a T-Cell/APC Luciferase Reporter Assay T-cell activation is achieved by stimulating T-cell receptors (TcR) that recognize specific peptides presented by major histocompatibility complex class I or II proteins on antigen-presenting cells (APC). Activated TcRs in turn initiate a cascade of signaling events that can be monitored by reporter genes driven by transcription factors such as activator-protein 1 (AP-1), Nuclear Factor of Activated T-cells (NFAT) or Nuclear factor kappa-light-chain-enhancer of activated B cells (NFκb). T-cell response is modulated via engagement of co-receptors expressed either constitutively or inducibly on T-cells. One such receptor is programmed cell death protein 1 (PD-1), a negative regulator of T-cell activity. PD-1 interacts with its ligand, PD-L1, which is expressed on target cells including APCs or cancer cells, and this interaction results in the delivery of inhibitory signals by recruiting phosphatases to the TcR signalosome, resulting in the suppression of positive signaling.

A bioassay was developed to measure T cell signaling induced by interaction between APC and T cells by utilizing a mixed culture derived from two mammalian cell lines: Jurkat cells (an immortalized T cell line) and Raji cells (a B cell line) (FIG. 1). For the first component of the bioassay, Jurkat Clone E6-1 cells (ATCC, #TIB-152) were transduced with the Cignal Lenti AP-1 Luc Reporter (Qiagen—Sabiosciences, #CLS-011L) as per the manufacturer's instructions. The lentivirus encodes the firefly luciferase gene under the control of a minimal CMV promoter, tandem repeats of the TPA-inducible transcriptional response element (TRE) and a puromycin resistance gene. The engineered Jurkat cell line was subsequently transduced with a PD-1 chimera comprising the extracellular domain of human PD-1 (amino acids from 1 to 170 of human PD1; accession number NP_005009.2) and the trans-membrane and cytoplasmic domains of human CD300a (amino acids from 181 to 299 of human CD300a; accession number NP_009192.2). The resulting stable cell line (Jurkat/AP1-Luc/hPD1-hCD300a)

was selected and maintained in RPMI/10% FBS/penicillin/streptomycin/glutamine supplemented with 500 ug/mL G418+1 ug/mL puromycin.

For the second component of the bioassay, Raji cells (ATCC, #CCL-86) were transduced with human PD-L1 gene (amino acids 1-290 of accession number NP_054862.1) that had been cloned into a lentiviral (pLEX) vector system (Thermo Scientific Biosystems, #OHS4735). Raji cells, positive for PD-L1 (Raji/hPD-L1) were isolated by FACS using a PD-L1 antibody and maintained in Iscove/ 10% FBS/penicillin/streptomycin/glutamine supplemented with 1 ug/mL puromycin.

To simulate the APC/T cell interaction, a bispecific antibody composed of one Fab arm that bindings to CD3 on T cells and the other one Fab arm binding that binds to CD20 on Raji cells (CD3×CD20 bispecific antibody; e.g., as disclosed in US20140088295) was utilized. The presence of the bispecific molecule in the assay results in the activation of the T cell and APC by bridging the CD3 subunits on T-cells to CD20 endogenously expressed on Raji cells. Ligation of CD3 with anti-CD3 antibodies has been demonstrated to lead to activation of T cells. In this bioassay, antibodies blocking the PD1/PD-L1 interaction rescue T-cell activity by disabling the inhibitory signaling and subsequently leading to increased AP1-Luc activation.

In the luciferase-based bioassay, RPMI1640 supplemented with 10% FBS and penicillin/streptomycin/glutamine was used as assay medium to prepare cell suspensions and antibody dilutions to carry out the screening of anti-PD-L1 monoclonal antibodies (mAbs). On the day of the screening, $EC_{50}$ values of anti-PD-L1 mAbs, in the presence of a fixed concentration of CD3×CD20 bispecific antibody (30 pM), as well as the $EC_{50}$ of the bispecific antibody alone, were determined. In the following order, cells and reagents were added to 96 well white, flat-bottom plates. For the anti-PD-L1 mAb $EC_{50}$ determinations, first a fixed concentration of CD3×CD20 bispecific antibody (final 30 pM) was prepared and added to the microtiter plate wells. Twelve-point serial dilutions of anti-PD-L1 mAbs and controls were then added (final concentrations ranging from 1.7 pM to 100 nM; plus wells with assay medium alone). For the bispecific antibody (alone) $EC_{50}$ determination, the bispecific antibody, at final concentrations ranging from 0.17 pM to 10 nM (plus wells with assay medium alone), was added to the microtiter plate wells. Subsequently, a 2.5×10^6/mL Raji/hPD-L1 cell suspension was prepared and 20 uL per well was added (final cell number/well 5×10^4 cells). Plates were left at room temperature (15-20 minutes), while a suspension of 2.5×10^6/mL of Jurkat/AP1-Luc/hPD1(ecto)-hCD300a(TM-Cyto) was prepared. 20 uL of the Jurkat suspension (final cell number/well 5×1^4 cells) was added per well. Plates containing the co-culture were incubated for 5 to 6 hours at 37° C. in 5% $CO_2$. Luciferase activity was then detected after the addition of ONE-Glo™ (Promega, # E6051) reagent and relative light units (RLUs) were measured on a Victor luminometer. All samples were tested in duplicates.

RLU values for each screened antibody were normalized by setting the assay condition with fixed (30 pM) concentration of the CD3/CD20 bispecific antibody, but without anti-PD-L1 antibody to 100%. This condition corresponds to the maximal AP1-Luc response elicited by the bispecific molecule in the presence of the PD-1/PD-L1 inhibitory signal. Upon addition of the anti-PD-L1 antibody, the inhibitory signal is suppressed, and the increased stimulation is shown here as $E_{max}$, the percentage increase in the signal in the presence of the highest antibody dose tested (100 nM).

To compare potency of the anti-PD-L1 antibodies tested, the concentration of antibody at which the normalized RLU value reached 125% activation was determined from a four-parameter logistic equation over a 12-point response curve using GraphPad Prism. The results are summarized in Table 15.

TABLE 15

Anti-PD-L1 antibody blocking PD-1/PD-L1 dependent inhibition of AP1-Luc signaling

| Antibody | Antagonistic assay Concentration [M] of Antibody at 125% activation | Antagonistic assay Emax mean [%] @ 100 nM |
|---|---|---|
| H2aM8306N | 3.78E−09 | 166.8 |
| H2aM8307N | N/A | 87.7 |
| H2aM8309N | 3.09E−10 | 180.9 |
| H2aM8310N | N/A | 112.8 |
| H2aM8312N | N/A | 75.6 |
| H2aM8314N | 1.44E−11 | 234.9 |
| H2aM8316N | 1.47E−10 | 177.4 |
| H2aM8317N | N/A | 109.2 |
| H2aM8321N | N/A | 116.8 |
| H2aM8323N | 2.20E−10 | 173.3 |
| H2aM8718N | 1.51E−10 | 182.0 |
| H1H9323P | N/A | 101.1 |
| H1H9327P | N/A | 77.1 |
| H1H9329P | N/A | 124.5 |
| H1H9336P | 9.81E−11 | 162.6 |
| H1H9344P2 | N/A | 98.3 |
| H1H9345P2 | N/A | 89.2 |
| H1H9351P2 | 3.44E−10 | 154.4 |
| H1H9354P2 | N/A | 89.9 |
| H1H9364P2 | 7.93E−11 | 164.5 |
| H1H9373P2 | 1.34E−10 | 150.2 |
| H1H9382P2 | N/A | 86.5 |
| H1H9387P2 | 1.86E−11 | 141.2 |
| H1H9396P2 | N/A | 102.6 |
| H1H8314N | 6.57E−11 | 147.9 |
| H1H9364P2 | 1.62E−10 | 158.1 |
| H1H9373P2 | 7.07E−11 | 152.5 |
| mIgG2a isotype control | N/A | 80.2 |
| hIgG1 isotype control | N/A | 96.8 |
| hIgG4 isotype control | N/A | 87.6 |

N/A = not applicable because at the concentrations tested these antibodies did not activate 125%

As shown in Table 15, 14 out of the 27 anti-PD-L1 antibodies of the invention tested blocked PD-1/PD-L1 inhibition with $E_{max}$ values ranging from 234.9 to 138.1. Thirteen out of the 27 anti-PD-L1 antibodies of the invention did not demonstrate substantial blockade of PD1/PD-L1 interaction when tested in this assay. Isotype controls did not interfere with the PD1/PD-L1 interaction.

Example 9: In Vivo Efficacy of Anti-PD-L1 Antibodies

To determine the effect of a select number of anti-PD-L1 antibodies of the invention in a relevant in vivo model, an MC38.ova tumor growth study, involving subcutaneous injection of tumor cells and started on different days, was conducted in mice that were homozygous for the expression of the extracellular domain of human PD-L1 in place of extracellular domain of mouse PD-L1 (PD-L1 Humin mice) on a 75% C57/B16/25% 129 strain background. MC38.Ova (mouse colon adenocarcinoma) cells were engineered to express chicken ovalbumin in order to increase tumor immunogenicity, and to allow monitoring of the T-cell immune responses to well-defined antigenic ovalbumin peptides. In a second step, MC38.Ova cells were transduced with a lentiviral vector expressing hPD-L1 under SFFV promoter.

MC38.Ova cells positive for hPD-L1 (MC38.Ova/hPD-L1) were isolated by FACS using hPD-L1-specific antibody. The cells were found to express low level of endogenous mouse PD-L1.

For a first study (study #1), mice were divided evenly according to body weight into 5 treatment or control groups (n=5 to 8 mice per group). At day 0, mice were anesthetized by isoflurane inhalation and then injected subcutaneously into the right flank with $1 \times 10^6$ MC38.ova/hPD-L1 cells in suspension of 100 uL of DMEM. Treatment groups were intraperitoneally injected with 500 ug of either one of three anti-PD-L1 antibodies of the invention, or one of two isotype control antibodies with irrelevant specificity on days 3, 7, 10, 14, and 17 of the experiment, while one group of mice was left untreated.

In a second study (study #2), PD-L1 humanized mice were randomized into 7 treatment groups (n=5 to 6 mice). On day 0, mice were subcutaneously implanted with 1×10^6 MC38.Ova/hPD-L1 cells. Mice were intraperitoneally administered with REGN a-PD-L1 ab (H1H8314N or H1H9364P2 or H1H9373P2), or isotype control abs hIgG4 mut or hIgG1 at doses of 10 mg/kg or 5 mg/kg. Groups of mice were administered antibody on days 3, 7, 10, 14, and 17. Tumor volumes were monitored by caliper measurement twice per week for the duration of the experiment (21 days). Experimental dosing and treatment protocol for groups of mice are shown in Table 16.

For the studies, average tumor volumes were monitored by caliper measurement twice per week for the duration of the experiment (17 days) and percent survival was recorded at the end of the experiment. In addition, the number of tumor-free mice was also assessed at the end of the study. Results, expressed as mean tumor volume $(mm^3)(\pm SD)$, percent survival, and number of tumor-free mice are shown in Tables 17 and 18.

TABLE 16

Experimental dosing and treatment protocol for groups of mice

| Study # | Samples tested | Dosage amount at each dosage time point | Dosing interval |
|---|---|---|---|
| 1 | Isotype control 1 | 500 μg | Days 3, 7, 10, 14, 17 |
|  | H1H8314N | 500 μg | Days 3, 7, 10, 14, 17 |
|  | H1H9364P2 | 500 μg | Days 3, 7, 10, 14, 17 |
|  | H1H9373P2 | 500 μg | Days 3, 7, 10, 14, 17 |
|  | Isotype control 2 | 500 μg | Days 3, 7, 10, 14, 17 |
| 2 | Isotype control 1 | 10 mg/kg | Days 3, 7, 10, 14, 17 |
|  | H1H8314N | 10 mg/kg | Days 3, 7, 10, 14, 17 |
|  | H1H8314N | 5 mg/kg | Days 3, 7, 10, 14, 17 |
|  | H1H9364P2 | 10 mg/kg | Days 3, 7, 10, 14, 17 |
|  | H1H9364P2 | 5 mg/kg | Days 3, 7, 10, 14, 17 |
|  | H1H9373P2 | 10 mg/kg | Days 3, 7, 10, 14, 17 |
|  | H1H9373P2 | 5 mg/kg | Days 3, 7, 10, 14, 17 |

TABLE 17

Mean tumor volume, percent survival and numbers of tumor-free mice in each treatment group from study # 1

| Antibody | Tumor Volume, mm³ mean (±SD) | | Survival, % | | Tumor-Free Mice |
|---|---|---|---|---|---|
|  | Days 10 | Day 17 | Day 10 | Day 17 | Day 17 |
| Isotype Control 1 | 65 (±27) | 148 (±109) | 100% | 100% | 0/5 (0%) |
| Isotype Control 2 | 54 (±44) | 80 (±63) | 100% | 100% | 0/5 (0%) |
| H1H8314N | 6 (±10) | 2 (±5) | 100% | 100% | 4/5 (80%) |
| H1H9364P2 | 16 (±17) | 0 (±0) | 100% | 100% | 5/5 (100%) |
| H1H9373P2 | 13 (±14) | 0 (±0) | 100% | 100% | 5/5 (100%) |

As shown in Table 17 for study #1, all three anti-PD-L1 antibodies of the invention were efficacious in promoting tumor regression at the dosage of 500 ug/mouse with all mice from treatment groups that received two of the antibodies, H1H9364P2 and H1H9373P2, being tumor free at day 17. In the treatment group that received one of the anti-PD-L1 antibodies of the invention, H1H8314N, 4 out of 5 mice were tumor free by day 17, whereas 0 out of 5 animals were tumor-free in the isotype control groups. One-way ANOVA with Dunnett's multiple comparison posttest revealed a significant difference in tumor volumes between treatments with anti-PD-L1 antibodies of the invention and the isotype control antibody with a p value <0.05.

TABLE 18

Mean tumor volume, percent survival and numbers of tumor-free mice in each treatment group from study #2

| Antibody | Tumor Volume, mm3 Mean (SD) | | | | Survival, % | | | | Tumor-free mice | Tumor-free mice |
|---|---|---|---|---|---|---|---|---|---|---|
|  | Day 10 10 MPK | Day 10 5 MPK | Day 21 10 MPK | Day 21 5 MPK | Day 10 10 MPK | Day 10 5 MPK | Day 21 10 MPK | Day 21 5 MPK | Day 21 10 MPK | Day 21 5 MPK |
| Isotype control 1 | 55 (37) | N/A | 534 (356) | N/A | 100% | N/A | 100% | N/A | 0/6 (0%) | N/A |
| H1H8314N | 14 (15) | 17 (4) | 19 (22) | 108 (101) | 100% | 100% | 100% | 100% | 3/6 (50%) | 2/5 (40%) |
| H1H9364P2 | 18 (10) | 23 (10) | 34 (81) | 231 (238) | 100% | 100% | 100% | 100% | 5/6 (83%) | 1/5 (20%) |
| H1H9373P2 | 10 (8) | 25 (29) | 7 (16) | 37 (59) | 100% | 100% | 100% | 100% | 5/6 (83%) | 3/5 (60%) |

As shown in Table 18, in study #2, administration of the selected anti-PD-L1 antibodies resulted in inhibition of tumor growth promoting tumor regression. All three anti-PD-L1 antibodies were efficacious at the 10 mg/kg dose and 5 mg/kg dose and promoted tumor regression in treated mice in a dose dependent manner throughout the course of the experiment, whereas 0 out of 5 animals were tumor-free in the control group. One-way ANOVA with Tukey's multiple comparison post-test revealed a significant difference in tumor volumes between treatments with the anti-PD-L1 antibodies and isotype control antibody with p value <0.05 or lower.

Example 10: Anti-Tumor Effects of a Combination of an Anti-PD-L1 Antibody and a VEGF Antagonist in a Mouse Early-Treatment Tumor Model An early-treatment tumor model was developed to test the efficacy of a combination of an anti-PD-L1 antibody and a VEGF antagonist. In this model, the combination therapy is administered shortly after tumor implantation. The experiment also used an anti-PD-1 antibody alone and in combination with the VEGF antagonist. The anti-PD-L1 antibody used in this experiment was an anti-PD-L1 monoclonal antibody with $V_H/V_L$ sequences of antibody "YW243.55S70" according to US20100203056A1 (Genentech, Inc.), with mouse IgG2a and which was cross-reactive with mouse PD-L1. The VEGF antagonist used in this experiment was aflibercept (a VEGF receptor-based chimeric molecule, also known as "VEGF-trap" or "VEGFR1R2-FcΔC1(a)," a full description of which is provided elsewhere herein). The anti-PD-1 antibody used in this experiment was anti-mouse PD-1 clone "RPMI-14" with rat IgG2b (Bio X Cell, West Lebanon, N.H.).

For this experimental model, $1.0\times10^6$ Colon-26 tumor cells were implanted sub-cutaneously into BALB/c mice at Day 0. Starting on Day 3, prior to the establishment of measurable tumors, mice were treated with one of the mono- or combination therapies, or control combination, as set forth in Table 19.

TABLE 19

Experimental Dosing and Treatment Groups

| Treatment Group | First Agent | Second Agent |
| --- | --- | --- |
| Control Combination | IgG2a isotype control (250 μg, IP) | hFc control (250 μg, SC) |
| VEGF Trap only | IgG2a isotype control (250 μg, IP) | Aflibercept (10 mg/kg, SC) |

TABLE 19-continued

Experimental Dosing and Treatment Groups

| Treatment Group | First Agent | Second Agent |
| --- | --- | --- |
| anti-PD-1 only | anti-PD-1 mAb RPMI-14 (250 μg, IP) | hFc control (250 μg, SC) |
| anti-PD-L1 only | anti-PD-L1 mAb (250 μg, IP) | hFc control (250 μg, SC) |
| VEGF Trap + anti-PD-1 | anti-PD-1 mAb RPMI-14 (250 μg, IP) | Aflibercept (10 mg/kg, SC) |
| VEGF Trap + anti-PD-L1 | anti-PD-L1 mAb (250 μg, IP) | Aflibercept (10 mg/kg, SC) |

The various therapies were administered at five different time points over a two week period (i.e., injections at Day 3, Day 6, Day 10, Day 13 and Day 19).

Animals in each therapy group were evaluated in terms of tumor incidence, tumor volume, median survival time, and number of tumor-free animals at Day 50. The extent of tumor growth is summarized in FIG. 2 (tumor growth curves) and FIG. 3 (tumor volume at Day 28). Results are also summarized in Table 20.

TABLE 20

Tumor-free mice upon treatment

| Treatment Group | No. of Tumor-Free Animals by Day 50 |
| --- | --- |
| Control Combination | 0/10 |
| VEGF Trap only | 3/10 |
| anti-PD-1 only | 4/10 |
| anti-PD-L1 only | 5/10 |
| VEGF Trap + anti-PD-1 | 7/10 |
| VEGF Trap + anti-PD-L1 | 9/10 |

Figure 2:
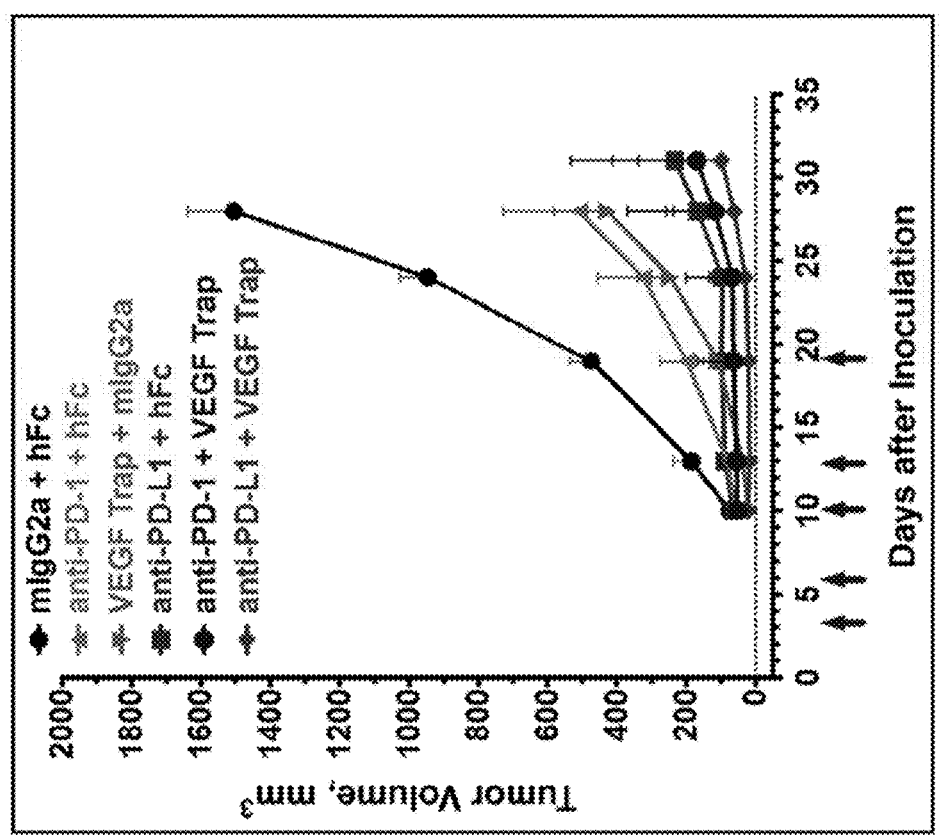
FIG. 2 illustrates tumor growth and survival results for mice implanted with Colon-26 tumor cells at Day 0 and treated with the indicated combinations of molecules by injection at Days 3, 6, 10, 13 and 19 ("early-treatment tumor model"). The graph depicts tumor volume (in $mm^3$) for the different experimental groups at various time points after implantation. Upward arrows along the X-axis indicate the timing of treatment injections. "mIgG2a" is IgG2 isotype control; "Fc" is human Fc control; "VEGF Trap" is aflibercept; "anti-PD-1" is anti-mouse PD-1 clone RPMI-14; "anti-PD-L1" is an anti-PD-L1 monoclonal antibody as described elsewhere herein.
Figure 3:
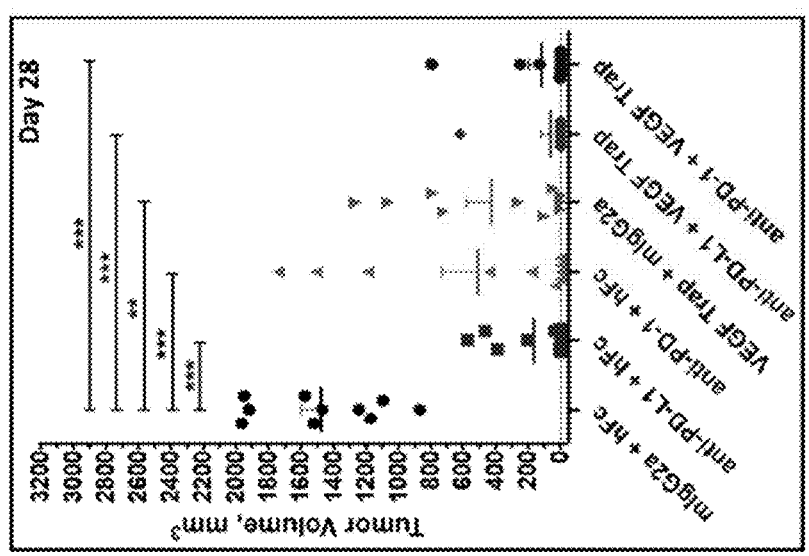
FIG. 3 illustrates tumor growth and survival results for mice implanted with Colon-26 tumor cells at Day 0 and treated with the indicated combinations of molecules by injection at Days 3, 6, 10, 13 and 19 ("early-treatment tumor model"). The graph shows the tumor volume (in $mm^3$) of individual mice in each experimental group at Day 28 after implantation. "mIgG2a" is IgG2 isotype control; "Fc" is human Fc control; "VEGF Trap" is aflibercept; "anti-PD-1" is anti-mouse PD-1 clone RPMI-14; "anti-PD-L1" is an anti-PD-L1 monoclonal antibody as described elsewhere herein.

Tumor growth was substantially reduced in animals treated with the combination of VEGF Trap+anti-PD-L1 antibody as compared with treatment regimens involving either therapeutic agent alone (see FIGS. 2 and 3). Furthermore, survival was substantially increased in the VEGF Trap+anti-PD-L1 antibody group, with 90% of animals surviving to at least day 50 after tumor implantation. By contrast, for the anti-PD-L1 and VEGF Trap monotherapy groups, survival to Day 50 was only 50% and 30% respectively (see FIG. 3 and Table 20).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated human monoclonal antibody or antigen-binding fragment thereof that binds specifically to human programmed death-ligand 1 (PD-L1) protein, wherein the antibody or antigen-binding fragment thereof comprises three heavy chain complementarity determining regions (CDRs) (HCDR1, HCDR2 and HCDR3) contained within a heavy chain variable region (HCVR) sequence of SEQ ID NO:82; and three light chain CDRs (LCDR1, LCDR2 and LCDR3) contained within a light chain variable region (LCVR) sequence of SEQ ID NO:90.

2. The isolated antibody or antigen-binding fragment thereof of claim 1, comprising:
   (a) a HCDR1 domain having an amino acid sequence of SEQ ID NO:84;
   (b) a HCDR2 domain having an amino acid sequence of SEQ ID NO:86;
   (c) a HCDR3 domain having an amino acid sequence of SEQ ID NO:88;
   (d) a LCDR1 domain having an amino acid sequence of SEQ ID NO:92;
   (e) a LCDR2 domain having an amino acid sequence of SEQ ID NO:94; and
   (f) a LCDR3 domain having an amino acid sequence of SEQ ID NO:96.

3. The isolated antibody or antigen-binding fragment thereof of claim 2, wherein the antibody or antigen-binding fragment thereof comprises an HCVR/LCVR amino acid sequence pair of SEQ ID NO:82/90.

4. The isolated antibody or antigen-binding fragment of claim 3, wherein the antibody or antigen-binding fragment thereof has one or more of the following properties:

(a) binds monomeric PD-L1 with a binding dissociation equilibrium constant ($K_D$) of less than about 310 pM as measured in a surface plasmon resonance assay at 37° C.;
   (b) binds monomeric human PD-L1 with a $K_D$ less than about 180 pM in a surface plasmon resonance assay at 25° C.;
   (c) binds dimeric human PD-L1 with a $K_D$ of less than about 15 pM as measured in a surface plasmon resonance assay at 37° C.; and
   (d) binds dimeric human PD-L1 with a $K_D$ less than about 8 pM in a surface plasmon resonance assay at 25° C.

5. The isolated antibody or antigen-binding fragment thereof of claim 1 that blocks PD-L1 binding to one of PD-1 or B7-1, as measured by a biosensor or surface plasmon resonance assay.

6. An isolated human monoclonal antibody or antigen-binding fragment thereof that competes for binding to human PD-L1 protein with a reference antibody comprising three CDRs of a HCVR, wherein the HCVR has an amino acid sequence of SEQ ID NO:82; and three CDRs of a LCVR, wherein the LCVR has an amino acid sequence of SEQ ID NO:90.

7. An isolated human monoclonal antibody or antigen-binding fragment thereof that binds to the same epitope on human PD-L1 protein as an antibody or antigen-binding fragment thereof which comprises three CDRs of a HCVR, wherein the HCVR has an amino acid sequence of SEQ ID NO:82; and three CDRs of a LCVR, wherein the LCVR has an amino acid sequence of SEQ ID NO:90.

8. A pharmaceutical composition comprising an isolated monoclonal antibody or antigen-binding fragment thereof that binds PD-L1 according to claim 1, and a pharmaceutically acceptable carrier or diluent.

* * * * *

SEQUENCE LISTING

<160> NUMBER OF SEQ ID NOS: 353

<210> SEQ ID NO 1
<211> LENGTH: 363
<212> TYPE: DNA
<213> ORGANISM: Artificial Sequence
<220> FEATURE:
<223> OTHER INFORMATION: Synthetic

<400> SEQUENCE: 1

```
gaggtgcagc tggtggagtc tgggggaggc ttggtccagc ctgggggtc cctgagactc      60 tcctgtgcag cctctggatt cacctttagt aggttttgga tgagctgggt ccgccaggct     120
```

```
ccagggaagg ggctggagtg ggtggccaac ataaaccaag atggaactga gaaatactat      180
gtggactctg tgaagggccg attcaccatc tccagagaca acgccaagaa ctcactgtat      240
ctgcaaatga acagcctgag agccggggac acggctgtgt attactgtgc gaatacgtat      300
tacgattttt ggagtggtca ctttgactac tggggccagg aaccctggt caccgtctcc      360 tca                                                                    363
```

<210> SEQ ID NO 2
<211> LENGTH: 121
<212> TYPE: PRT
<213> ORGANISM: Artificial Sequence
<220> FEATURE:
<223> OTHER INFORMATION: Synthetic

<400> SEQUENCE: 2

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Phe
            20                  25                  30

Trp Met Ser Trp Val Arg Gln Ala Pro Gly Lys Gly Leu Glu Trp Val
        35                  40                  45

Ala Asn Ile Asn Gln Asp Gly Thr Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gly Asp Thr Ala Val Tyr Tyr Cys
                85                  90                  95

Ala Asn Thr Tyr Tyr Asp Phe Trp Ser Gly His Phe Asp Tyr Trp Gly
            100                 105                 110

Gln Gly Thr Leu Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcacct ttagtaggtt ttgg                                             24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Phe Thr Phe Ser Arg Phe Trp
 1               5
```

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
ataaaccaag atggaactga gaaa                                              24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Asn Gln Asp Gly Thr Glu Lys
 1               5

<210> SEQ ID NO 7
<211> LENGTH: 42
<212> TYPE: DNA
<213> ORGANISM: Artificial Sequence
<220> FEATURE:
<223> OTHER INFORMATION: Synthetic

<400> SEQUENCE: 7
gcgaatacgt attacgattt ttggagtggt cactttgact ac                          42

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Ala Asn Thr Tyr Tyr Asp Phe Trp Ser Gly His Phe Asp Tyr
 1               5                  10

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccttccacc ctgtctgcat ctgtaggaga cagagtcacc        60
atcacttgtc gggccagtca gagtattagt aattggttgg cctggtatca gcagaaacca       120
gggaaagccc ctaagctcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgccaacag tatcatagtt attcgtacac ttttggccag       300
gggaccaagc tggagatcaa a                                                 321

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asn Trp
             20                  25                  30

Leu Ala Trp Tyr Gln Gln Lys Pro Gly Lys Ala Pro Lys Leu Leu Ile

```
                35                  40                  45
Tyr Lys Ala Ser Ser Leu Glu Ser Gly Val Pro Ser Arg Phe Ser Gly
         50                  55                  60
Ser Gly Ser Gly Thr Glu Phe Thr Leu Thr Ile Ser Ser Leu Gln Pro
 65                  70                  75                  80
Asp Asp Phe Ala Thr Tyr Tyr Cys Gln Gln Tyr His Ser Tyr Ser Tyr
                 85                  90                  95
Thr Phe Gly Gln Gly Thr Lys Leu Glu Ile Lys
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagtatta gtaattgg                                              18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Ile Ser Asn Trp
 1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 aaggcgtct                                                         9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Lys Ala Ser
 1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacagtatc atagttattc gtacact                                    27

<210> SEQ ID NO 16
<211> LENGTH: 9

```
<212> TYPE: PRT
<213> ORGANISM: Artificial Sequence
<220> FEATURE:
<223> OTHER INFORMATION: Synthetic

<400> SEQUENCE: 16

Gln Gln Tyr His Ser Tyr Ser Tyr Thr
  1               5

<210> SEQ ID NO 17
<211> LENGTH: 363
<212> TYPE: DNA
<213> ORGANISM: Artificial Sequence
<220> FEATURE:
<223> OTHER INFORMATION: Synthetic

<400> SEQUENCE: 17
caggagcacc tggtggagtc tgggggaggc gtggtccagc ctggagggtc cctgagactc      60
tcctgtgaag cgtctggatt caccttcagt aactttggca tgcactgggt ccgccaggct     120
ccaggcaagg ggctggagtg ggtggcagct ttatggtctg atggaagtaa taaatactat     180
gcagactccg tgaagggtcg agtcaccatc tccagagaca attccaagaa cacactgtat     240
ctgcaaatga acagcctgag agccgaggac acggctgtct attactgtgc gagagggaga     300 ggagccccccg gtattccgat ttttgggtac tggggccagg gaaccctggt caccgtctcc     360
tca                                                                   363

<210> SEQ ID NO 18
<211> LENGTH: 121
<212> TYPE: PRT
<213> ORGANISM: Artificial Sequence
<220> FEATURE:
<223> OTHER INFORMATION: Synthetic

<400> SEQUENCE: 18

Gln Glu His Leu Val Glu Ser Gly Gly Gly Val Val Gln Pro Gly Arg
  1               5                  10                  15

Ser Leu Arg Leu Ser Cys Glu Ala Ser Gly Phe Thr Phe Ser Asn Phe
                 20                  25                  30

Gly Met His Trp Val Arg Gln Ala Pro Gly Lys Gly Leu Glu Trp Val
             35                  40                  45

Ala Ala Leu Trp Ser Asp Gly Ser Asn Lys Tyr Tyr Ala Asp Ser Val
         50                  55                  60

Lys Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Gly Ala Pro Gly Ile Pro Ile Phe Gly Tyr Trp Gly
            100                 105                 110

Gln Gly Thr Leu Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct tcagtaactt tggc                                             24
```

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Ser Asn Phe Gly
 1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
ttatggtctg atggaagtaa taaa                                           24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Leu Trp Ser Asp Gly Ser Asn Lys
 1               5

<210> SEQ ID NO 23
<211> LENGTH: 42
<212> TYPE: DNA
<213> ORGANISM: Artificial Sequence
<220> FEATURE:
<223> OTHER INFORMATION: Synthetic

<400> SEQUENCE: 23
gcgagaggga gaggagcccc cggtattccg attttgggt ac                        42

<210> SEQ ID NO 24
<211> LENGTH: 14
<212> TYPE: PRT
<213> ORGANISM: Artificial Sequence
<220> FEATURE:
<223> OTHER INFORMATION: Synthetic

<400> SEQUENCE: 24

Ala Arg Gly Arg Gly Ala Pro Gly Ile Pro Ile Phe Gly Tyr
 1               5                   10

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccatcctcc ctgtctgcat ctgttggaga cagagtcacc     60
atcacttgcc gggcaagtca gggcattaga aatgatttag ctggtatca gcagaaacca    120 gggaaagccc ctaagcgcct gatctatact gcatccagtt tgcaaagtgg ggtcccatca    180

```
agattcagcg gcagtggatc tgggacagaa ttcactctca caatcagcag cctacagcct    240
gaagattttg caacttatta ctgtctacaa cataatagtt accctctcac attcggcgga    300
gggaccaagg tggcgatcaa a                                              321
```

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Thr Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Ala Ile Lys
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27

```
cagggcatta gaaatgat                                                   18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

```
Gln Gly Ile Arg Asn Asp
 1               5
```

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29

```
actgcatcc                                                              9
```

<210> SEQ ID NO 30
<211> LENGTH: 3
<212> TYPE: PRT

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Thr Ala Ser
 1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
ctacaacata atagttaccc tctcaca                                        27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Leu Gln His Asn Ser Tyr Pro Leu Thr
 1               5

<210> SEQ ID NO 33
<211> LENGTH: 390
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tgggggaggc ttggtaaagc ctgggggtc ccttagactc      60 tcctgtgcag cctctggatt cactttcagt aacgcctgga tgagctgggt ccgccaggct   120
ccagggaagg ggctggagtg ggttggccgt attaaaagga aaactgatgg tgggacaaca   180
gactacgctg cacccgtgaa aggcagattc accatctcaa gagatgattc aaaaaatacg   240
ctgcatctgc aaatgaacag cctgaaaacc gaggacacag ccgtgtatta ctgtaccaca   300
gatgatattg tagttgtacc agctgttatg agggaatact acttcggtat ggacgtctgg   360
ggccaaggga ccacggtcac cgtctcctca                                    390

<210> SEQ ID NO 34
<211> LENGTH: 130
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Arg Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu His Leu Gln Met Asn Ser Leu Lys Thr Glu Asp Thr Ala Val Tyr
                 85                  90                  95

Tyr Cys Thr Thr Asp Asp Ile Val Val Val Pro Ala Val Met Arg Glu
            100                 105                 110

Tyr Tyr Phe Gly Met Asp Val Trp Gly Gln Gly Thr Thr Val Thr Val
        115                 120                 125

Ser Ser
    130

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcactt tcagtaacgc ctgg                                          24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Asn Ala Trp
1               5

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
attaaaagga aaactgatgg tgggacaaca                                    30

<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Ile Lys Arg Lys Thr Asp Gly Gly Thr Thr
1               5                   10

<210> SEQ ID NO 39
<211> LENGTH: 63
<212> TYPE: DNA
<213> ORGANISM: Artificial Sequence
<220> FEATURE:
<223> OTHER INFORMATION: Synthetic

<400> SEQUENCE: 39
accacagatg atattgtagt tgtaccagct gttatgaggg aatactactt cggtatggac   60
gtc                                                                 63

<210> SEQ ID NO 40
<211> LENGTH: 21
<212> TYPE: PRT
<213> ORGANISM: Artificial Sequence
<220> FEATURE:
<223> OTHER INFORMATION: Synthetic

<400> SEQUENCE: 40

Thr Thr Asp Asp Ile Val Val Val Pro Ala Val Met Arg Glu Tyr Tyr
1               5                   10                  15

Phe Gly Met Asp Val
            20

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41
gacatccaga tgacccagtc tccatcctcc ctgtctgcat ctgtaggaga cagagtcacc      60
atcacttgcc ggacaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataataatt acccgtacac ttttggccag     300
gggaccaagc tggagatcaa a                                               321

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Tyr
                85                  90                  95

Thr Phe Gly Gln Gly Thr Lys Leu Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43

```
cagggcatta gaaatgat                                                    18
```

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Gly Ile Arg Asn Asp
 1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45

```
gctgcatcc                                                               9
```

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47

```
ctacagcata ataattaccc gtacact                                          27
```

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Leu Gln His Asn Asn Tyr Pro Tyr Thr
 1               5

<210> SEQ ID NO 49
<211> LENGTH: 363
<212> TYPE: DNA
<213> ORGANISM: Artificial Sequence
<220> FEATURE:
<223> OTHER INFORMATION: Synthetic

<400> SEQUENCE: 49

```
caggtgcaat tggtgcagtc tggggcggag gtgaagaagc ctggggcctc agtgcaggtc       60
tcctgcaagg cttctggata ctccttcacc ggctactata tacactgggt gcgacaggcc     120
```

```
cctggacaag gacttgagtg gatgggatgg atcaaccccta acagtggcac caaaaagtat    180
gcacacaagt tcagggcag ggtcaccatg accaggaca cgtccatcga cacagcctac      240
atgattttga gcagtctgat atccgacgac acggccgtgt attactgtgc gagagatgag    300
gactggaact tgggagctg gttcgactcc tggggccagg gaaccctggt caccgtctcc     360
tca                                                                  363
```

```
<210> SEQ ID NO 50
<211> LENGTH: 121
<212> TYPE: PRT
<213> ORGANISM: Artificial Sequence
<220> FEATURE:
<223> OTHER INFORMATION: Synthetic

<400> SEQUENCE: 50
```

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Ser Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Thr Lys Lys Tyr Ala His Lys Phe
    50                  55                  60

Gln Gly Arg Val Thr Met Thr Arg Asp Thr Ser Ile Asp Thr Ala Tyr
65                  70                  75                  80

Met Ile Leu Ser Ser Leu Ile Ser Asp Asp Thr Ala Val Tyr Tyr Cys
                85                  90                  95

Ala Arg Asp Glu Asp Trp Asn Phe Gly Ser Trp Phe Asp Ser Trp Gly
            100                 105                 110

Gln Gly Thr Leu Val Thr Val Ser Ser
        115                 120

```
<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggatactcct tcaccggcta ctat                                           24
```

```
<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52
```

Gly Tyr Ser Phe Thr Gly Tyr Tyr
1               5

```
<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
```
atcaacccta acagtggcac caaa                                              24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Asn Pro Asn Ser Gly Thr Lys
1               5

<210> SEQ ID NO 55
<211> LENGTH: 42
<212> TYPE: DNA
<213> ORGANISM: Artificial Sequence
<220> FEATURE:
<223> OTHER INFORMATION: Synthetic

<400> SEQUENCE: 55
gcgagagatg aggactggaa ctttgggagc tggttcgact cc                          42

<210> SEQ ID NO 56
<211> LENGTH: 14
<212> TYPE: PRT
<213> ORGANISM: Artificial Sequence
<220> FEATURE:
<223> OTHER INFORMATION: Synthetic

<400> SEQUENCE: 56

Ala Arg Asp Glu Asp Trp Asn Phe Gly Ser Trp Phe Asp Ser
1               5                   10

<210> SEQ ID NO 57
<211> LENGTH: 336
<212> TYPE: DNA
<213> ORGANISM: Artificial Sequence
<220> FEATURE:
<223> OTHER INFORMATION: Synthetic

<400> SEQUENCE: 57
gatattgtga tgacccagac tccactctcc tcacctgtca cccttggaca gccggcctcc       60
atctcctgca ggtctagtca aaccctcgta cacggtgatg aaacacgta cttgagttgg      120 attcagcaga ggccaggcca gcctccgaga ctcctcattt ataaggtttc taatcagttc      180
tctggggtcc cagacagatt cagtggcagt ggggcaggga cagatttcac actgaaaatc      240
agcagggtgg aagctgagga tgtcgggctt tatttctgca tgcaagctac acattttccg      300
atcaccttcg gccaagggac acgactggag attaaa                                336

<210> SEQ ID NO 58
<211> LENGTH: 112
<212> TYPE: PRT
<213> ORGANISM: Artificial Sequence
<220> FEATURE:
<223> OTHER INFORMATION: Synthetic

<400> SEQUENCE: 58

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Thr Leu Val His Gly
            20                  25                  30

Asp Gly Asn Thr Tyr Leu Ser Trp Ile Gln Gln Arg Pro Gly Gln Pro
            35                  40                  45

Pro Arg Leu Leu Ile Tyr Lys Val Ser Asn Gln Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Leu Tyr Phe Cys Met Gln Ala
                85                  90                  95

Thr His Phe Pro Ile Thr Phe Gly Gln Gly Thr Arg Leu Glu Ile Lys
            100                 105                 110

<210> SEQ ID NO 59
<211> LENGTH: 33
<212> TYPE: DNA
<213> ORGANISM: Artificial Sequence
<220> FEATURE:
<223> OTHER INFORMATION: Synthetic

<400> SEQUENCE: 59
caaaccctcg tacacggtga tggaaacacg tac                                33

<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60

Gln Thr Leu Val His Gly Asp Gly Asn Thr Tyr
1               5                   10

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 aaggtttct                                                           9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Lys Val Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
atgcaagcta cacattttcc gatcacc                                       27

<210> SEQ ID NO 64

```
<211> LENGTH: 9
<212> TYPE: PRT
<213> ORGANISM: Artificial Sequence
<220> FEATURE:
<223> OTHER INFORMATION: Synthetic

<400> SEQUENCE: 64

Met Gln Ala Thr His Phe Pro Ile Thr
 1               5

<210> SEQ ID NO 65
<211> LENGTH: 363
<212> TYPE: DNA
<213> ORGANISM: Artificial Sequence
<220> FEATURE:
<223> OTHER INFORMATION: Synthetic

<400> SEQUENCE: 65
caggtacacc tggtgcagtc tggggctgag gtgaagaagc ctggggcctc agtgaaggtc      60
tcctgcaagg cttctggata caccttcacc ggctactata cattgggt gcgacaggcc      120 cctggacacg gcttgagtg atgggatgg ctcaaccta atactggtac cacaaagtat       180
atacagaact ttcagggcag ggtcaccatg accaggaca cgtccagcag cacagcctac      240
atggagctga ccaggctgag atctgacgac acggccgtgt attactgtgc gagagatgag      300
gactggaatt atgggagctg gttcgacacc tggggccagg gaaccctggt cacagtctcc      360
tca                                                                 363

<210> SEQ ID NO 66
<211> LENGTH: 121
<212> TYPE: PRT
<213> ORGANISM: Artificial Sequence
<220> FEATURE:
<223> OTHER INFORMATION: Synthetic

<400> SEQUENCE: 66

Gln Val His Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Tyr Ile His Trp Val Arg Gln Ala Pro Gly His Gly Leu Glu Trp Met
            35                  40                  45

Gly Trp Leu Asn Pro Asn Thr Gly Thr Thr Lys Tyr Ile Gln Asn Phe
        50                  55                  60

Gln Gly Arg Val Thr Met Thr Arg Asp Thr Ser Ser Ser Thr Ala Tyr
65                  70                  75                  80

Met Glu Leu Thr Arg Leu Arg Ser Asp Asp Thr Ala Val Tyr Tyr Cys
                85                  90                  95

Ala Arg Asp Glu Asp Trp Asn Tyr Gly Ser Trp Phe Asp Thr Trp Gly
               100                 105                 110

Gln Gly Thr Leu Val Thr Val Ser Ser
           115                 120

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
```
ggatacacct tcaccggcta ctat                                              24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Tyr Thr Phe Thr Gly Tyr Tyr
 1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
ctcaacccta atactggtac caca                                              24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Leu Asn Pro Asn Thr Gly Thr Thr
 1               5

<210> SEQ ID NO 71
<211> LENGTH: 42
<212> TYPE: DNA
<213> ORGANISM: Artificial Sequence
<220> FEATURE:
<223> OTHER INFORMATION: Synthetic

<400> SEQUENCE: 71
gcgagagatg aggactggaa ttatgggagc tggttcgaca cc                          42

<210> SEQ ID NO 72
<211> LENGTH: 14
<212> TYPE: PRT
<213> ORGANISM: Artificial Sequence
<220> FEATURE:
<223> OTHER INFORMATION: Synthetic

<400> SEQUENCE: 72

Ala Arg Asp Glu Asp Trp Asn Tyr Gly Ser Trp Phe Asp Thr
 1               5                  10

<210> SEQ ID NO 73
<211> LENGTH: 336
<212> TYPE: DNA
<213> ORGANISM: Artificial Sequence
<220> FEATURE:
<223> OTHER INFORMATION: Synthetic

<400> SEQUENCE: 73
gatattgtaa tgacccagac tccactctcc tcacctgtca cccttggaca gccggcctcc       60
atctcctgca ggtctagtcc aagcctcgta cacagtgatg gaaacaccta cttgagttgg      120

```
cttcagcaga ggccaggcca gcctccaaga ctcctaattt ataagatttc taaccgattc    180
tctggggtcc cagacagatt cagtggcagt ggggcaggga cagatttcac gctgaaaatc    240
agcagggtgg aagctgagga tgtcggggtt tattactgca tgcaagctac acattttccg    300
atcaccttcg gccaagggac acgactggag attaga                              336
```

```
<210> SEQ ID NO 74
<211> LENGTH: 112
<212> TYPE: PRT
<213> ORGANISM: Artificial Sequence
<220> FEATURE:
<223> OTHER INFORMATION: Synthetic

<400> SEQUENCE: 74

Asp Ile Val Met Thr Gln Thr Pro Leu Ser Ser Pro Val Thr Leu Gly
1               5                   10                  15

Gln Pro Ala Ser Ile Ser Cys Arg Ser Ser Pro Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Phe Pro Ile Thr Phe Gly Gln Gly Thr Arg Leu Glu Ile Arg
            100                 105                 110

<210> SEQ ID NO 75
<211> LENGTH: 33
<212> TYPE: DNA
<213> ORGANISM: Artificial Sequence
<220> FEATURE:
<223> OTHER INFORMATION: Synthetic

<400> SEQUENCE: 75
ccaagcctcg tacacagtga tggaaacacc tac                                  33

<210> SEQ ID NO 76
<211> LENGTH: 11
<212> TYPE: PRT
<213> ORGANISM: Artificial Sequence
<220> FEATURE:
<223> OTHER INFORMATION: Synthetic

<400> SEQUENCE: 76

Pro Ser Leu Val His Ser Asp Gly Asn Thr Tyr
1               5                   10

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 aagatttct                                                              9

<210> SEQ ID NO 78
<211> LENGTH: 3
```

<212> TYPE: PRT
<213> ORGANISM: Artificial Sequence
<220> FEATURE:
<223> OTHER INFORMATION: Synthetic

<400> SEQUENCE: 78

Lys Ile Ser
 1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
atgcaagcta cacattttcc gatcacc                                              27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Met Gln Ala Thr His Phe Pro Ile Thr
 1               5

<210> SEQ ID NO 81
<211> LENGTH: 360
<212> TYPE: DNA
<213> ORGANISM: Artificial Sequence
<220> FEATURE:
<223> OTHER INFORMATION: Synthetic

<400> SEQUENCE: 81
gaggtgcagc tggtggaatc tgggggaggt gtggtgcggc ctggggggtc cctgagactc          60
tcctgtgcag cctctggatt cacttttgat gattatggca tgacctgggt ccgccaagct         120
ccagggaggg gcctggaatg ggtctctggt attcattgga tggtaaacg cacaggttat          180 gcagactctg tgaagggccg attcaccata tccagagaca cgccaagaa tccctgtat           240 ctgcaaatga acagtctgaa aggcgaggac acggccttgt atcattgtgt gaggggggga         300
atgagtacag gggactggtt cgaccctgg ggccagggaa ccctggtcat cgtctcctca          360

<210> SEQ ID NO 82
<211> LENGTH: 120
<212> TYPE: PRT
<213> ORGANISM: Artificial Sequence
<220> FEATURE:
<223> OTHER INFORMATION: Synthetic

<400> SEQUENCE: 82

Glu Val Gln Leu Val Glu Ser Gly Gly Gly Val Val Arg Pro Gly Gly
 1               5                  10                  15

Ser Leu Arg Leu Ser Cys Ala Ala Ser Gly Phe Thr Phe Asp Asp Tyr
                20                  25                  30

Gly Met Thr Trp Val Arg Gln Ala Pro Gly Arg Gly Leu Glu Trp Val
            35                  40                  45

Ser Gly Ile His Trp His Gly Lys Arg Thr Gly Tyr Ala Asp Ser Val
        50                  55                  60

Lys Gly Arg Phe Thr Ile Ser Arg Asp Asn Ala Lys Lys Ser Leu Tyr
 65                  70                  75                  80

Leu Gln Met Asn Ser Leu Lys Gly Glu Asp Thr Ala Leu Tyr His Cys
                 85                  90                  95

Val Arg Gly Gly Met Ser Thr Gly Asp Trp Phe Asp Pro Trp Gly Gln
            100                 105                 110

Gly Thr Leu Val Ile Val Ser Ser
            115                 120

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcactt ttgatgatta tggc                                              24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Thr Phe Asp Asp Tyr Gly
 1               5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
attcattggc atggtaaacg caca                                              24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile His Trp His Gly Lys Arg Thr
 1               5

<210> SEQ ID NO 87
<211> LENGTH: 39
<212> TYPE: DNA
<213> ORGANISM: Artificial Sequence
<220> FEATURE:
<223> OTHER INFORMATION: Synthetic

<400> SEQUENCE: 87 gtgaggggg gaatgagtac aggggactgg ttcgacccc                               39

<210> SEQ ID NO 88
<211> LENGTH: 13
<212> TYPE: PRT
<213> ORGANISM: Artificial Sequence
<220> FEATURE:
<223> OTHER INFORMATION: Synthetic

<400> SEQUENCE: 88

Val Arg Gly Gly Met Ser Thr Gly Asp Trp Phe Asp Pro
 1               5                  10

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccatcctcc ctgtctgcat ctctaggaga cagagtcacc      60
atcacttgcc gggcaagtca gagcattaac agttatttaa attggtatca gcagaaacca     120
gggaaagccc ctaaactcct gatctatgtt gcatccagtt tgcaaagtgg ggtcccatca     180
aggttcagtg gcagtggatc tgggacagaa ttcactctca ccatcagcaa tctgcaacct     240
gaagattttg caacttacta ctgtcaacag agttacagta cccctccgat caccttcggc     300
caagggacac gactggagat taaa                                            324

<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Leu Gly
 1               5                  10                  15

Asp Arg Val Thr Ile Thr Cys Arg Ala Ser Gln Ser Ile Asn Ser Tyr
             20                  25                  30

Leu Asn Trp Tyr Gln Gln Lys Pro Gly Lys Ala Pro Lys Leu Leu Ile
         35                  40                  45

Tyr Val Ala Ser Ser Leu Gln Ser Gly Val Pro Ser Arg Phe Ser Gly
     50                  55                  60

Ser Gly Ser Gly Thr Glu Phe Thr Leu Thr Ile Ser Asn Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagagcatta acagttat                                                    18

<210> SEQ ID NO 92
<211> LENGTH: 6
<212> TYPE: PRT
<213> ORGANISM: Artificial Sequence
<220> FEATURE:

<223> OTHER INFORMATION: Synthetic

<400> SEQUENCE: 92

Gln Ser Ile Asn Ser Tyr
 1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gttgcatcc                                                                        9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Val Ala Ser
 1

<210> SEQ ID NO 95
<211> LENGTH: 30
<212> TYPE: DNA
<213> ORGANISM: Artificial Sequence
<220> FEATURE:
<223> OTHER INFORMATION: Synthetic

<400> SEQUENCE: 95
caacagagtt acagtacccc tccgatcacc                                                30

<210> SEQ ID NO 96
<211> LENGTH: 10
<212> TYPE: PRT
<213> ORGANISM: Artificial Sequence
<220> FEATURE:
<223> OTHER INFORMATION: Synthetic

<400> SEQUENCE: 96

Gln Gln Ser Tyr Ser Thr Pro Pro Ile Thr
 1               5                  10

<210> SEQ ID NO 97
<211> LENGTH: 360
<212> TYPE: DNA
<213> ORGANISM: Artificial Sequence
<220> FEATURE:
<223> OTHER INFORMATION: Synthetic

<400> SEQUENCE: 97
gaggtgcagc tggtggagtc tgggggaggt gtggtacggc cggggggtc cctgagactc          60 tcctgtgcag cctctggatt cacctttgat gattatggca tgacctgggt ccgccaagtt         120
ccagggaagg ggctggagtg ggtctctggt attcattgga gtggtagaag cacaggttat        180
gcagactctg tgaagggccg attcaccatc tccagagaca cgccaagaa ctccctgtat          240 ctgcaaatga acagtctgag agccgaggac acggccttgt attactgtgc gagggggga          300 atgagtacgg gggactggtt cgaccctgg ggccagggaa ccctggtcac cgtctcctca          360

<210> SEQ ID NO 98
<211> LENGTH: 120
<212> TYPE: PRT
<213> ORGANISM: Artificial Sequence
<220> FEATURE:
<223> OTHER INFORMATION: Synthetic

<400> SEQUENCE: 98

```
Glu Val Gln Leu Val Glu Ser Gly Gly Val Val Arg Pro Gly Gly
 1               5                  10                  15

Ser Leu Arg Leu Ser Cys Ala Ala Ser Gly Phe Thr Phe Asp Asp Tyr
            20                  25                  30

Gly Met Thr Trp Val Arg Gln Val Pro Gly Lys Gly Leu Glu Trp Val
        35                  40                  45

Ser Gly Ile His Trp Ser Gly Arg Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Gly Met Ser Thr Gly Asp Trp Phe Asp Pro Trp Gly Gln
            100                 105                 110

Gly Thr Leu Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct ttgatgatta tggc    24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Phe Thr Phe Asp Asp Tyr Gly
 1               5
```

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
attcattgga gtggtagaag caca    24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile His Trp Ser Gly Arg Ser Thr
1               5

<210> SEQ ID NO 103
<211> LENGTH: 39
<212> TYPE: DNA
<213> ORGANISM: Artificial Sequence
<220> FEATURE:
<223> OTHER INFORMATION: Synthetic

<400> SEQUENCE: 103 gcgaggggg gaatgagtac gggggactgg ttcgacccc                              39

<210> SEQ ID NO 104
<211> LENGTH: 13
<212> TYPE: PRT
<213> ORGANISM: Artificial Sequence
<220> FEATURE:
<223> OTHER INFORMATION: Synthetic

<400> SEQUENCE: 104

Ala Arg Gly Gly Met Ser Thr Gly Asp Trp Phe Asp Pro
1               5                   10

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgtt gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaa                                             324

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagagcatta gcagctat                                                 18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Ser Ile Ser Ser Tyr
 1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gttgcatcc                                                            9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Val Ala Ser
 1

<210> SEQ ID NO 111
<211> LENGTH: 30
<212> TYPE: DNA
<213> ORGANISM: Artificial Sequence
<220> FEATURE:
<223> OTHER INFORMATION: Synthetic

<400> SEQUENCE: 111
caacagagtt acagtaccccc tccgatcacc                                    30

<210> SEQ ID NO 112
<211> LENGTH: 10
<212> TYPE: PRT
<213> ORGANISM: Artificial Sequence
<220> FEATURE:
<223> OTHER INFORMATION: Synthetic

<400> SEQUENCE: 112

Gln Gln Ser Tyr Ser Thr Pro Pro Ile Thr
 1               5                  10

<210> SEQ ID NO 113
<211> LENGTH: 345
<212> TYPE: DNA
<213> ORGANISM: Artificial Sequence
<220> FEATURE:
<223> OTHER INFORMATION: Synthetic

<400> SEQUENCE: 113

```
gaggtgcagt tggtggagtc tggaggaggc ttggtccagc ctgggggtc cctaagactc      60 tcctgtgcag cctctgggtt caccgtcggt agtaactaca tgaactgggt ccgtcaggct    120
ccagggaagg gactggagtg ggtctcagtt atttatagtg gtggtagtac atactacgca    180
gattccgtga agggccgatt caccatctcc agactcactt ccaagaacac actgtatctt    240
caaatgagca gcctgagacc tgaggacacg gccgtgtatt attgtgcgag agggattagg    300
ggtctggacg tctggggcca agggaccacg gtcaccgtct cttca                    345
```

<210> SEQ ID NO 114
<211> LENGTH: 115
<212> TYPE: PRT
<213> ORGANISM: Artificial Sequence
<220> FEATURE:
<223> OTHER INFORMATION: Synthetic

<400> SEQUENCE: 114

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Gly Ser Asn
             20                  25                  30

Tyr Met Asn Trp Val Arg Gln Ala Pro Gly Lys Gly Leu Glu Trp Val
         35                  40                  45

Ser Val Ile Tyr Ser Gly Gly Ser Thr Tyr Tyr Ala Asp Ser Val Lys
     50                  55                  60

Gly Arg Phe Thr Ile Ser Arg Leu Thr Ser Lys Asn Thr Leu Tyr Leu
 65                  70                  75                  80

Gln Met Ser Ser Leu Arg Pro Glu Asp Thr Ala Val Tyr Tyr Cys Ala
                 85                  90                  95

Arg Gly Ile Arg Gly Leu Asp Val Trp Gly Gln Gly Thr Thr Val Thr
            100                 105                 110

Val Ser Ser
        115
```

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115

```
gggttcaccg tcggtagtaa ctac                                            24
```

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Val Gly Ser Asn Tyr

<210> SEQ ID NO 117
<211> LENGTH: 21
<212> TYPE: DNA
<213> ORGANISM: Artificial Sequence
<220> FEATURE:
<223> OTHER INFORMATION: Synthetic

<400> SEQUENCE: 117
atttatagtg gtggtagtac a                                          21

<210> SEQ ID NO 118
<211> LENGTH: 7
<212> TYPE: PRT
<213> ORGANISM: Artificial Sequence
<220> FEATURE:
<223> OTHER INFORMATION: Synthetic

<400> SEQUENCE: 118

Ile Tyr Ser Gly Gly Ser Thr
1               5

<210> SEQ ID NO 119
<211> LENGTH: 27
<212> TYPE: DNA
<213> ORGANISM: Artificial Sequence
<220> FEATURE:
<223> OTHER INFORMATION: Synthetic

<400> SEQUENCE: 119
gcgagaggga ttagggggtct ggacgtc                                   27

<210> SEQ ID NO 120
<211> LENGTH: 9
<212> TYPE: PRT
<213> ORGANISM: Artificial Sequence
<220> FEATURE:
<223> OTHER INFORMATION: Synthetic

<400> SEQUENCE: 120

Ala Arg Gly Ile Arg Gly Leu Asp Val
1               5

<210> SEQ ID NO 121
<211> LENGTH: 324
<212> TYPE: DNA
<213> ORGANISM: Artificial Sequence
<220> FEATURE:
<223> OTHER INFORMATION: Synthetic

<400> SEQUENCE: 121
gacatccaga tgacccagtc tccatcctcc ctgtctgcat ctgtaggaga cagagtcacc    60
atcacttgcc gggcaagtca gaccattaac atctatttaa attggtatca gcagaaacca   120
gggagagccc ctaggctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaccag agttacagta cccctccgat caccttcggc   300
caagggacac gactggagat taaa                                          324

<210> SEQ ID NO 122
<211> LENGTH: 108
<212> TYPE: PRT
<213> ORGANISM: Artificial Sequence
<220> FEATURE:
<223> OTHER INFORMATION: Synthetic

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Ile Tyr
            20                  25                  30

Leu Asn Trp Tyr Gln Gln Lys Pro Gly Arg Ala Pro Arg Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Ser Tyr Ser Thr Pro Pro
                85                  90                  95

Ile Thr Phe Gly Gln Gly Thr Arg Leu Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagaccatta acatctat                                                    18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Thr Ile Asn Ile Tyr
1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 gctgcatcc                                                               9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Ala Ala Ser
1

<210> SEQ ID NO 127
<211> LENGTH: 30

<212> TYPE: DNA
<213> ORGANISM: Artificial Sequence
<220> FEATURE:
<223> OTHER INFORMATION: Synthetic

<400> SEQUENCE: 127
caccagagtt acagtacccc tccgatcacc      30

<210> SEQ ID NO 128
<211> LENGTH: 10
<212> TYPE: PRT
<213> ORGANISM: Artificial Sequence
<220> FEATURE:
<223> OTHER INFORMATION: Synthetic

<400> SEQUENCE: 128

His Gln Ser Tyr Ser Thr Pro Pro Ile Thr
 1               5                  10

<210> SEQ ID NO 129
<211> LENGTH: 345
<212> TYPE: DNA
<213> ORGANISM: Artificial Sequence
<220> FEATURE:
<223> OTHER INFORMATION: Synthetic

<400> SEQUENCE: 129
gaggaacggt tggtggagtc tggaggagac ttggtccagc ctgggggtc cctgagactc      60 tcctgtgcag cctctggcat caccgtcggt actaattata tgaactgggt ccgccaggct     120
ccagggaagg gactggagtg ggtctcagtt atttctagcg gtggtaatac acactacgca     180
gactccgtga agggccgatt cattatgtcc agacaaactt ccaaaaacac gctgtatctt     240
cagatgaata gcctggaaac tgaggacacg gccgtatatt attgtgcgag ggggatcaga     300
ggtttggacg tctggggcca aggaccatg gtcaccgtct cctca                      345

<210> SEQ ID NO 130
<211> LENGTH: 115
<212> TYPE: PRT
<213> ORGANISM: Artificial Sequence
<220> FEATURE:
<223> OTHER INFORMATION: Synthetic

<400> SEQUENCE: 130

Glu Glu Arg Leu Val Glu Ser Gly Gly Asp Leu Val Gln Pro Gly Gly
 1               5                  10                  15

Ser Leu Arg Leu Ser Cys Ala Ala Ser Gly Ile Thr Val Gly Thr Asn
            20                  25                  30

Tyr Met Asn Trp Val Arg Gln Ala Pro Gly Lys Gly Leu Glu Trp Val
        35                  40                  45

Ser Val Ile Ser Ser Gly Gly Asn Thr His Tyr Ala Asp Ser Val Lys
    50                  55                  60

Gly Arg Phe Ile Met Ser Arg Gln Thr Ser Lys Asn Thr Leu Tyr Leu
65                  70                  75                  80

Gln Met Asn Ser Leu Glu Thr Glu Asp Thr Ala Val Tyr Tyr Cys Ala
                85                  90                  95

Arg Gly Ile Arg Gly Leu Asp Val Trp Gly Gln Gly Thr Met Val Thr
            100                 105                 110

Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggcatcaccg tcggtactaa ttat                                    24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Ile Thr Val Gly Thr Asn Tyr
 1               5

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
atttctagcg gtggtaatac a                                       21

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Ile Ser Ser Gly Gly Asn Thr
 1               5

<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135 gcgagggga tcagaggttt ggacgtc                                  27

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136

Ala Arg Gly Ile Arg Gly Leu Asp Val
 1               5

<210> SEQ ID NO 137
<211> LENGTH: 324
<212> TYPE: DNA
<213> ORGANISM: Artificial Sequence
<220> FEATURE:
<223> OTHER INFORMATION: Synthetic

<400> SEQUENCE: 137

```
gacatccaga tgacccagtc tccatcctcc ctgtctgcat ctgtaggaga cagagtcacc      60
atcacttgcc gggcaagtca gagcatgagc agctatttaa attggtatca gcagaaacca     120
gggagagccc ctaagctcct gatctttgct gcatccagtt tgcaaagtgg ggtcccatca     180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324
```

<210> SEQ ID NO 138
<211> LENGTH: 108
<212> TYPE: PRT
<213> ORGANISM: Artificial Sequence
<220> FEATURE:
<223> OTHER INFORMATION: Synthetic

<400> SEQUENCE: 138

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Met Ser Ser Tyr
             20                  25                  30

Leu Asn Trp Tyr Gln Gln Lys Pro Gly Arg Ala Pro Lys Leu Leu Ile
         35                  40                  45

Phe Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139

```
cagagcatga gcagctat                                                   18
```

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

```
Gln Ser Met Ser Ser Tyr
  1               5
```

<210> SEQ ID NO 141
<211> LENGTH: 9
<212> TYPE: DNA
<213> ORGANISM: Artificial Sequence
<220> FEATURE:

<223> OTHER INFORMATION: Synthetic

<400> SEQUENCE: 141 gctgcatcc                                                             9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Ala Ser
 1

<210> SEQ ID NO 143
<211> LENGTH: 30
<212> TYPE: DNA
<213> ORGANISM: Artificial Sequence
<220> FEATURE:
<223> OTHER INFORMATION: Synthetic

<400> SEQUENCE: 143
caacagagtt acagtacccc tccgatcacc                                     30

<210> SEQ ID NO 144
<211> LENGTH: 10
<212> TYPE: PRT
<213> ORGANISM: Artificial Sequence
<220> FEATURE:
<223> OTHER INFORMATION: Synthetic

<400> SEQUENCE: 144

Gln Gln Ser Tyr Ser Thr Pro Pro Ile Thr
 1               5                  10

<210> SEQ ID NO 145
<211> LENGTH: 354
<212> TYPE: DNA
<213> ORGANISM: Artificial Sequence
<220> FEATURE:
<223> OTHER INFORMATION: Synthetic

<400> SEQUENCE: 145
caggtccagc tggtgcagtc tggggctgag gtgaagatgc ctgggtcctc ggtgagggtc     60
tcctgcaagg cttctggagg catcttcagc agttctacta tcagttgggt gcgacaggcc    120
cctggacaag ggcttgaatg gatgggagag atcatccctg tctttggtac agtaaactac    180
gcacagaagt tccaggacag agtcatattt accgcggacg aatctacgac tacagcctac    240
atggagctga gcagcctgaa atctggggac acggccgtat atttctgtgc gcgaaattgg    300
ggattaggct cttttatat ctggggccaa gggacaatgg tcaccgtctc ttca           354

<210> SEQ ID NO 146
<211> LENGTH: 118
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Gln Ser Gly Ala Glu Val Lys Met Pro Gly Ser
 1               5                  10                  15

```
Ser Val Arg Val Ser Cys Lys Ala Ser Gly Ile Phe Ser Ser Ser
            20                  25                  30

Thr Ile Ser Trp Val Arg Gln Ala Pro Gly Gln Gly Leu Glu Trp Met
        35                  40                  45

Gly Glu Ile Ile Pro Val Phe Gly Thr Val Asn Tyr Ala Gln Lys Phe
 50                  55                  60

Gln Asp Arg Val Ile Phe Thr Ala Asp Glu Ser Thr Thr Thr Ala Tyr
 65                  70                  75                  80

Met Glu Leu Ser Ser Leu Lys Ser Gly Asp Thr Ala Val Tyr Phe Cys
                85                  90                  95

Ala Arg Asn Trp Gly Leu Gly Ser Phe Tyr Ile Trp Gly Gln Gly Thr
            100                 105                 110

Met Val Thr Val Ser Ser
        115

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggaggcatct tcagcagttc tact                                           24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Gly Ile Phe Ser Ser Ser Thr
 1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atcatccctg tctttggtac agta                                           24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ile Pro Val Phe Gly Thr Val
 1               5

<210> SEQ ID NO 151
<211> LENGTH: 33
<212> TYPE: DNA
<213> ORGANISM: Artificial Sequence
<220> FEATURE:
<223> OTHER INFORMATION: Synthetic
```

<400> SEQUENCE: 151
gcgcgaaatt ggggattagg ctcttttat atc                              33

<210> SEQ ID NO 152
<211> LENGTH: 11
<212> TYPE: PRT
<213> ORGANISM: Artificial Sequence
<220> FEATURE:
<223> OTHER INFORMATION: Synthetic

<400> SEQUENCE: 152

Ala Arg Asn Trp Gly Leu Gly Ser Phe Tyr Ile
 1               5                  10

<210> SEQ ID NO 153
<211> LENGTH: 324
<212> TYPE: DNA
<213> ORGANISM: Artificial Sequence
<220> FEATURE:
<223> OTHER INFORMATION: Synthetic

<400> SEQUENCE: 153
gaaattgtgt tgacgcagtc tccaggcacc ctgtctttgt ctccagggga aagagccacc     60
ctctcctgca gggccagtca gagttttaac ttcaactact tagcctggta ccagcagaaa    120
cctggccagg ctcccagact cctcatctat ggtgcatcca gcagggccac tggcatccca    180
gacaggttca gtggcagtgg gtctgggaca gacttcactc tcaccatcaa caggctggag    240
cctgaagatt ttggagtgtt ttattgtcag cagtatgaaa gcgcaccttg acgttcggc     300 caagggacca aggtggaaat caaa                                           324

<210> SEQ ID NO 154
<211> LENGTH: 108
<212> TYPE: PRT
<213> ORGANISM: Artificial Sequence
<220> FEATURE:
<223> OTHER INFORMATION: Synthetic

<400> SEQUENCE: 154

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Phe Asn Phe Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Gly Val Phe Tyr Cys Gln Gln Tyr Glu Ser Ala Pro
                85                  90                  95

Trp Thr Phe Gly Gln Gly Thr Lys Val Glu Ile Lys
            100                 105

<210> SEQ ID NO 155
<211> LENGTH: 21
<212> TYPE: DNA
<213> ORGANISM: Artificial Sequence
<220> FEATURE:
<223> OTHER INFORMATION: Synthetic

<400> SEQUENCE: 155 cagagttttta acttcaacta c                                              21

<210> SEQ ID NO 156
<211> LENGTH: 7
<212> TYPE: PRT
<213> ORGANISM: Artificial Sequence
<220> FEATURE:
<223> OTHER INFORMATION: Synthetic

<400> SEQUENCE: 156

Gln Ser Phe Asn Phe Asn Tyr
 1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 ggtgcatcc                                                              9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Gly Ala Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
cagcagtatg aaagcgcacc ttggacg                                         27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Tyr Glu Ser Ala Pro Trp Thr
 1               5

<210> SEQ ID NO 161
<211> LENGTH: 345
<212> TYPE: DNA
<213> ORGANISM: Artificial Sequence
<220> FEATURE:
<223> OTHER INFORMATION: Synthetic

<400> SEQUENCE: 161
gaggtgcagc ttgtagagtc tggggggagac ttggtacatc ctggcaggtc cctgagactc    60
tcctgtgcag cctctggttt ccccttttgat gagtatgcca tgcactgggt ccggcaagtt   120

```
ccagggaagg gcctggagtg ggtctcaggt attagttgga gtaataataa cataggctat    180
gcggactctg tgaagggccg attcaccatc tccagagaca cgccaaaaa ctccctgtat     240 ctacaaatga acagtctgag acctgaggac acggccttt attactgtgc aaaatctgga    300
atctttgact cctggggcca gggaaccctg gtcaccgtct cctca                    345
```

```
<210> SEQ ID NO 162
<211> LENGTH: 115
<212> TYPE: PRT
<213> ORGANISM: Artificial Sequence
<220> FEATURE:
<223> OTHER INFORMATION: Synthetic

<400> SEQUENCE: 162
```

Glu Val Gln Leu Val Glu Ser Gly Gly Asp Leu Val His Pro Gly Arg
1               5                   10                  15

Ser Leu Arg Leu Ser Cys Ala Ala Ser Gly Phe Pro Phe Asp Glu Tyr
            20                  25                  30

Ala Met His Trp Val Arg Gln Val Pro Gly Lys Gly Leu Glu Trp Val
        35                  40                  45

Ser Gly Ile Ser Trp Ser Asn Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Phe Tyr Tyr Cys
                85                  90                  95

Ala Lys Ser Gly Ile Phe Asp Ser Trp Gly Gln Gly Thr Leu Val Thr
            100                 105                 110

Val Ser Ser
        115

```
<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
gtttccccct tgatgagta tgcc                                             24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164
```

Gly Phe Pro Phe Asp Glu Tyr Ala
1               5

```
<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
attagttgga gtaataataa cata                                            24
```

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Ser Trp Ser Asn Asn Asn Ile
1               5

<210> SEQ ID NO 167
<211> LENGTH: 24
<212> TYPE: DNA
<213> ORGANISM: Artificial Sequence
<220> FEATURE:
<223> OTHER INFORMATION: Synthetic

<400> SEQUENCE: 167
gcaaaatctg gaatctttga ctcc                                          24

<210> SEQ ID NO 168
<211> LENGTH: 8
<212> TYPE: PRT
<213> ORGANISM: Artificial Sequence
<220> FEATURE:
<223> OTHER INFORMATION: Synthetic

<400> SEQUENCE: 168

Ala Lys Ser Gly Ile Phe Asp Ser
1               5

<210> SEQ ID NO 169
<211> LENGTH: 315
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaagctcc tgatctatgc tgcatccagt ttgcaaagtg ggtcccatc acggttcagt    180 ggcggtggat ctgggacaga tttcactctc accatcagca gtctgcgacc tgaagatttt   240
gcaacttact actgtcaaca gagttactgt accctccga tcaccttcgg ccaagggaca    300
cgactggaga ttaaa                                                   315

<210> SEQ ID NO 170
<211> LENGTH: 105
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Leu Leu Ile Tyr Ala Ala
        35                  40                  45

Ser Ser Leu Gln Ser Gly Val Pro Ser Arg Phe Ser Gly Gly Gly Ser
        50                  55                  60

Gly Thr Asp Phe Thr Leu Thr Ile Ser Ser Leu Arg Pro Glu Asp Phe
65                  70                  75                  80

Ala Thr Tyr Tyr Cys Gln Gln Ser Tyr Cys Thr Pro Pro Ile Thr Phe
                85                  90                  95

Gly Gln Gly Thr Arg Leu Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
cagagcatta gcagctat                                                 18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Ser Ile Ser Ser Tyr
1               5

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gctgcatcc                                                            9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Ala Ala Ser
1

<210> SEQ ID NO 175
<211> LENGTH: 30
<212> TYPE: DNA
<213> ORGANISM: Artificial Sequence
<220> FEATURE:
<223> OTHER INFORMATION: Synthetic

<400> SEQUENCE: 175
caacagagtt actgtacccc tccgatcacc                                    30

<210> SEQ ID NO 176
<211> LENGTH: 10
<212> TYPE: PRT

```
<213> ORGANISM: Artificial Sequence
<220> FEATURE:
<223> OTHER INFORMATION: Synthetic

<400> SEQUENCE: 176

Gln Gln Ser Tyr Cys Thr Pro Pro Ile Thr
 1               5                  10

<210> SEQ ID NO 177
<211> LENGTH: 354
<212> TYPE: DNA
<213> ORGANISM: Artificial Sequence
<220> FEATURE:
<223> OTHER INFORMATION: Synthetic

<400> SEQUENCE: 177
gaggtgcagc tggtggagtc cggggggaggc gtggtccagc ctgggaggtc cctgagactc    60
tcctgtgcag cctctggatt caccttcagt agttatggca tgcactgggt ccgccaggct   120
ccaggcaagg gactggagtg ggtgacactt atatcatatg agggaaggaa taaatactat   180
gcagactccg tgaagggccg attcaccatt tccagagaca attccaagaa cacgctgtat   240
ctgcaaatga acagcctgag agctgaggac acggctgtat attactgtgc gaaagatagg   300
accctttacg gtatggacgt ctggggccaa ggaaccacgg tcaccgtctc ctca         354

<210> SEQ ID NO 178
<211> LENGTH: 118
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Thr Leu Ile Ser Tyr Glu Gly Arg Asn Lys Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Asp Arg Thr Leu Tyr Gly Met Asp Val Trp Gly Gln Gly Thr
            100                 105                 110

Thr Val Thr Val Ser Ser
        115

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggattcacct tcagtagtta tggc                                            24

<210> SEQ ID NO 180
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Ser Tyr Gly
 1               5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
atatcatatg agggaaggaa taaa                                               24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Ser Tyr Glu Gly Arg Asn Lys
 1               5

<210> SEQ ID NO 183
<211> LENGTH: 33
<212> TYPE: DNA
<213> ORGANISM: Artificial Sequence
<220> FEATURE:
<223> OTHER INFORMATION: Synthetic

<400> SEQUENCE: 183
gcgaaagata ggacccttta cggtatggac gtc                                     33

<210> SEQ ID NO 184
<211> LENGTH: 11
<212> TYPE: PRT
<213> ORGANISM: Artificial Sequence
<220> FEATURE:
<223> OTHER INFORMATION: Synthetic

<400> SEQUENCE: 184

Ala Lys Asp Arg Thr Leu Tyr Gly Met Asp Val
 1               5                  10

<210> SEQ ID NO 185
<211> LENGTH: 363
<212> TYPE: DNA
<213> ORGANISM: Artificial Sequence
<220> FEATURE:
<223> OTHER INFORMATION: Synthetic

<400> SEQUENCE: 185
caggtcacct tgagggagtc tggtcctgcg ctggtgaaaa ccacacagac cctcacactg         60
acctgcacct tctctgggtt ctcactcagc actaatagaa tgtgtgtgac ctggatccgt        120
cagcccccag ggaaggccct ggagtggctt gcgcgcattg attgggatgg tgttaaatac        180
tacaacacat ctctgaagac caggctcacc atctccaagg acacctccaa aaaccaggtg        240
```

```
gtccttacaa tgaccaacat ggaccctgtg dacacagcca ctttttactg tgcacggtcg    300
acttcgttga cttttactac ctttgactac tggggccagg gaaccctggt caccgtctcc    360
tca                                                                  363
```

<210> SEQ ID NO 186
<211> LENGTH: 121
<212> TYPE: PRT
<213> ORGANISM: Artificial Sequence
<220> FEATURE:
<223> OTHER INFORMATION: Synthetic

<400> SEQUENCE: 186

Gln Val Thr Leu Arg Glu Ser Gly Pro Ala Leu Val Lys Thr Thr Gln
1               5                   10                  15

Thr Leu Thr Leu Thr Cys Thr Phe Ser Gly Phe Ser Leu Ser Thr Asn
            20                  25                  30

Arg Met Cys Val Thr Trp Ile Arg Gln Pro Pro Gly Lys Ala Leu Glu
        35                  40                  45

Trp Leu Ala Arg Ile Asp Trp Asp Gly Val Lys Tyr Tyr Asn Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Phe Tyr
                85                  90                  95

Cys Ala Arg Ser Thr Ser Leu Thr Phe Tyr Tyr Phe Asp Tyr Trp Gly
            100                 105                 110

Gln Gly Thr Leu Val Thr Val Ser Ser
        115                 120

<210> SEQ ID NO 187
<211> LENGTH: 30
<212> TYPE: DNA
<213> ORGANISM: Artificial Sequence
<220> FEATURE:
<223> OTHER INFORMATION: Synthetic

<400> SEQUENCE: 187

```
gggttctcac tcagcactaa tagaatgtgt                                      30
```

<210> SEQ ID NO 188
<211> LENGTH: 10
<212> TYPE: PRT
<213> ORGANISM: Artificial Sequence
<220> FEATURE:
<223> OTHER INFORMATION: Synthetic

<400> SEQUENCE: 188

Gly Phe Ser Leu Ser Thr Asn Arg Met Cys
1               5                   10

<210> SEQ ID NO 189
<211> LENGTH: 21
<212> TYPE: DNA
<213> ORGANISM: Artificial Sequence
<220> FEATURE:
<223> OTHER INFORMATION: Synthetic

<400> SEQUENCE: 189

```
attgattggg atggtgttaa a                                               21
```

<210> SEQ ID NO 190

```
<211> LENGTH: 7
<212> TYPE: PRT
<213> ORGANISM: Artificial Sequence
<220> FEATURE:
<223> OTHER INFORMATION: Synthetic

<400> SEQUENCE: 190

Ile Asp Trp Asp Gly Val Lys
 1               5

<210> SEQ ID NO 191
<211> LENGTH: 39
<212> TYPE: DNA
<213> ORGANISM: Artificial Sequence
<220> FEATURE:
<223> OTHER INFORMATION: Synthetic

<400> SEQUENCE: 191
gcacggtcga cttcgttgac tttttactac tttgactac                              39

<210> SEQ ID NO 192
<211> LENGTH: 13
<212> TYPE: PRT
<213> ORGANISM: Artificial Sequence
<220> FEATURE:
<223> OTHER INFORMATION: Synthetic

<400> SEQUENCE: 192

Ala Arg Ser Thr Ser Leu Thr Phe Tyr Tyr Phe Asp Tyr
 1               5                  10

<210> SEQ ID NO 193
<211> LENGTH: 324
<212> TYPE: DNA
<213> ORGANISM: Artificial Sequence
<220> FEATURE:
<223> OTHER INFORMATION: Synthetic

<400> SEQUENCE: 193
gacatccaga tgacccagtc tccatcctcc ctgtctgcat ctgtaggaga cagagtcacc        60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat tcactctca  ccatcagcag tctgcaacct      240
gaagattttg caacttacta ctgtcaacag agttacagta cccctccgat caccttcggc      300
caagggacac gactggagat taaa                                             324

<210> SEQ ID NO 194
<211> LENGTH: 108
<212> TYPE: PRT
<213> ORGANISM: Artificial Sequence
<220> FEATURE:
<223> OTHER INFORMATION: Synthetic

<400> SEQUENCE: 194

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 195
<211> LENGTH: 18
<212> TYPE: DNA
<213> ORGANISM: Artificial Sequence
<220> FEATURE:
<223> OTHER INFORMATION: Synthetic

<400> SEQUENCE: 195
cagagcatta gcagctat         18

<210> SEQ ID NO 196
<211> LENGTH: 6
<212> TYPE: PRT
<213> ORGANISM: Artificial Sequence
<220> FEATURE:
<223> OTHER INFORMATION: Synthetic

<400> SEQUENCE: 196

Gln Ser Ile Ser Ser Tyr
1               5

<210> SEQ ID NO 197
<211> LENGTH: 9
<212> TYPE: DNA
<213> ORGANISM: Artificial Sequence
<220> FEATURE:
<223> OTHER INFORMATION: Synthetic

<400> SEQUENCE: 197 gctgcatcc         9

<210> SEQ ID NO 198
<211> LENGTH: 3
<212> TYPE: PRT
<213> ORGANISM: Artificial Sequence
<220> FEATURE:
<223> OTHER INFORMATION: Synthetic

<400> SEQUENCE: 198

Ala Ala Ser
1

<210> SEQ ID NO 199
<211> LENGTH: 30
<212> TYPE: DNA
<213> ORGANISM: Artificial Sequence
<220> FEATURE:
<223> OTHER INFORMATION: Synthetic

<400> SEQUENCE: 199
caacagagtt acagtacccc tccgatcacc         30

<210> SEQ ID NO 200
<211> LENGTH: 10
<212> TYPE: PRT
<213> ORGANISM: Artificial Sequence
<220> FEATURE:
<223> OTHER INFORMATION: Synthetic

<400> SEQUENCE: 200

Gln Gln Ser Tyr Ser Thr Pro Pro Ile Thr
1               5                   10

<210> SEQ ID NO 201
<211> LENGTH: 345
<212> TYPE: DNA
<213> ORGANISM: Artificial Sequence
<220> FEATURE:
<223> OTHER INFORMATION: Synthetic

<400> SEQUENCE: 201

```
gaggtgcagc tggtggagtc tgggggaggc ttggtccagc cggggggtc cctgagactc      60
tcctgtgcag cctctgagtt caccgtcggt accaaccaca tgaactgggt ccgccaggct    120
ccagggaagg gactggagtg ggtctcagtt atttatagcg gtggtaacac attctacgca    180
gactccgtga aggccgatt caccatctcc agacacactt ccaagaacac gctgtatctt    240
caaatgaaca gcctgacagc agaggacacg gccgtatatt actgtgcgcg aggattgggg    300
ggtatggacg tctggggcca agggaccacg gtcaccgtct cctca                    345
```

<210> SEQ ID NO 202
<211> LENGTH: 115
<212> TYPE: PRT
<213> ORGANISM: Artificial Sequence
<220> FEATURE:
<223> OTHER INFORMATION: Synthetic

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Val Gly Thr Asn
            20                  25                  30

His Met Asn Trp Val Arg Gln Ala Pro Gly Lys Gly Leu Glu Trp Val
        35                  40                  45

Ser Val Ile Tyr Ser Gly Gly Asn Thr Phe Tyr Ala Asp Ser Val Lys
    50                  55                  60

Gly Arg Phe Thr Ile Ser Arg His Thr Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Gly Leu Gly Gly Met Asp Val Trp Gly Gln Gly Thr Thr Val Thr
            100                 105                 110

Val Ser Ser
        115

<210> SEQ ID NO 203
<211> LENGTH: 24
<212> TYPE: DNA
<213> ORGANISM: Artificial Sequence
<220> FEATURE:
<223> OTHER INFORMATION: Synthetic

<400> SEQUENCE: 203
gagttcaccg tcggtaccaa ccac                                             24

<210> SEQ ID NO 204
<211> LENGTH: 8
<212> TYPE: PRT
<213> ORGANISM: Artificial Sequence
<220> FEATURE:
<223> OTHER INFORMATION: Synthetic

<400> SEQUENCE: 204

Glu Phe Thr Val Gly Thr Asn His
1               5

<210> SEQ ID NO 205
<211> LENGTH: 21
<212> TYPE: DNA
<213> ORGANISM: Artificial Sequence
<220> FEATURE:
<223> OTHER INFORMATION: Synthetic

<400> SEQUENCE: 205
atttatagcg gtggtaacac a                                      21

<210> SEQ ID NO 206
<211> LENGTH: 7
<212> TYPE: PRT
<213> ORGANISM: Artificial Sequence
<220> FEATURE:
<223> OTHER INFORMATION: Synthetic

<400> SEQUENCE: 206

Ile Tyr Ser Gly Gly Asn Thr
1               5

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
gcgcgaggat tgggggtat ggacgtc                                27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Ala Arg Gly Leu Gly Gly Met Asp Val
1               5

<210> SEQ ID NO 209
<211> LENGTH: 321
<212> TYPE: DNA
<213> ORGANISM: Artificial Sequence
<220> FEATURE:
<223> OTHER INFORMATION: Synthetic

<400> SEQUENCE: 209
gacatccaga tgacccagtc tccatcctcc ctgtctgcat ctgtaggaga cagagtcacc    60
atcacttgcc gggcgagtca ggtcattagc aattatttag cctggtatca gcagaaacca   120
gggaaagttc ctaggctcct gatctatgct gcatccactt tgcaatcagg ggtcccatct   180
cgtttcagtg gcagtggatc tgggacagat ttcactctca ccatcagcag cctgcagcct   240
gaagatgttg caacttatta ctgtcaaaag tataacagtg cccctcggac gttcggccaa   300
gggaccaagg tggaaatcaa a                                            321

<210> SEQ ID NO 210
<211> LENGTH: 107
<212> TYPE: PRT
<213> ORGANISM: Artificial Sequence
<220> FEATURE:
<223> OTHER INFORMATION: Synthetic

<400> SEQUENCE: 210

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Val Ile Ser Asn Tyr
             20                  25                  30

Leu Ala Trp Tyr Gln Gln Lys Pro Gly Lys Val Pro Arg Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Arg
                 85                  90                  95

Thr Phe Gly Gln Gly Thr Lys Val Glu Ile Lys
            100                 105
```

<210> SEQ ID NO 211
<211> LENGTH: 18
<212> TYPE: DNA
<213> ORGANISM: Artificial Sequence
<220> FEATURE:
<223> OTHER INFORMATION: Synthetic

<400> SEQUENCE: 211
caggtcatta gcaattat                                              18

<210> SEQ ID NO 212
<211> LENGTH: 6
<212> TYPE: PRT
<213> ORGANISM: Artificial Sequence
<220> FEATURE:
<223> OTHER INFORMATION: Synthetic

<400> SEQUENCE: 212

```
Gln Val Ile Ser Asn Tyr
  1               5
```

<210> SEQ ID NO 213
<211> LENGTH: 9
<212> TYPE: DNA
<213> ORGANISM: Artificial Sequence
<220> FEATURE:
<223> OTHER INFORMATION: Synthetic

<400> SEQUENCE: 213 gctgcatcc                                                         9

<210> SEQ ID NO 214
<211> LENGTH: 3
<212> TYPE: PRT
<213> ORGANISM: Artificial Sequence
<220> FEATURE:
<223> OTHER INFORMATION: Synthetic

<400> SEQUENCE: 214

-continued

Ala Ala Ser
 1

<210> SEQ ID NO 215
<211> LENGTH: 27
<212> TYPE: DNA
<213> ORGANISM: Artificial Sequence
<220> FEATURE:
<223> OTHER INFORMATION: Synthetic

<400> SEQUENCE: 215
caaaagtata acagtgcccc tcggacg                                          27

<210> SEQ ID NO 216
<211> LENGTH: 9
<212> TYPE: PRT
<213> ORGANISM: Artificial Sequence
<220> FEATURE:
<223> OTHER INFORMATION: Synthetic

<400> SEQUENCE: 216

Gln Lys Tyr Asn Ser Ala Pro Arg Thr
 1               5

<210> SEQ ID NO 217
<211> LENGTH: 360
<212> TYPE: DNA
<213> ORGANISM: Artificial Sequence
<220> FEATURE:
<223> OTHER INFORMATION: Synthetic

<400> SEQUENCE: 217
gaggtgcagc tggtggagtc tgggggaggc ttggtccagc gggggagtc cctgagactt      60 tactgtgcag cctctggatt cacctttagt aaatattgga tgaactgggt ccgccaggct    120
ccagggaagg ggctggagtg ggtggccaac ataaagggag atggaagtga aaatactat     180 gtggactctg tgaagggccg gttcaccatc tccagagaca acgccaagaa ctcactatat    240
ctacaaatga acagcctgag agccgaggac acggctgttt attactgtgc gagagattat    300
tggggatcag gctactactt tgacttctgg ggccagggaa ccctggtcac cgtctcctca    360

<210> SEQ ID NO 218
<211> LENGTH: 120
<212> TYPE: PRT
<213> ORGANISM: Artificial Sequence
<220> FEATURE:
<223> OTHER INFORMATION: Synthetic

<400> SEQUENCE: 218

Glu Val Gln Leu Val Glu Ser Gly Gly Gly Leu Val Gln Arg Gly Glu
 1               5                  10                  15

Ser Leu Arg Leu Tyr Cys Ala Ala Ser Gly Phe Thr Phe Ser Lys Tyr
                20                  25                  30

Trp Met Asn Trp Val Arg Gln Ala Pro Gly Lys Gly Leu Glu Trp Val
            35                  40                  45

Ala Asn Ile Lys Gly Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Trp Gly Ser Gly Tyr Tyr Phe Asp Phe Trp Gly Gln

```
                100             105             110
Gly Thr Leu Val Thr Val Ser Ser
        115                 120

<210> SEQ ID NO 219
<211> LENGTH: 24
<212> TYPE: DNA
<213> ORGANISM: Artificial Sequence
<220> FEATURE:
<223> OTHER INFORMATION: Synthetic

<400> SEQUENCE: 219
ggattcacct ttagtaaata ttgg                                         24

<210> SEQ ID NO 220
<211> LENGTH: 8
<212> TYPE: PRT
<213> ORGANISM: Artificial Sequence
<220> FEATURE:
<223> OTHER INFORMATION: Synthetic

<400> SEQUENCE: 220

Gly Phe Thr Phe Ser Lys Tyr Trp
1               5

<210> SEQ ID NO 221
<211> LENGTH: 24
<212> TYPE: DNA
<213> ORGANISM: Artificial Sequence
<220> FEATURE:
<223> OTHER INFORMATION: Synthetic

<400> SEQUENCE: 221
ataaagggag atggaagtga gaaa                                         24

<210> SEQ ID NO 222
<211> LENGTH: 8
<212> TYPE: PRT
<213> ORGANISM: Artificial Sequence
<220> FEATURE:
<223> OTHER INFORMATION: Synthetic

<400> SEQUENCE: 222

Ile Lys Gly Asp Gly Ser Glu Lys
1               5

<210> SEQ ID NO 223
<211> LENGTH: 39
<212> TYPE: DNA
<213> ORGANISM: Artificial Sequence
<220> FEATURE:
<223> OTHER INFORMATION: Synthetic

<400> SEQUENCE: 223
gcgagagatt attggggatc aggctactac tttgacttc                         39

<210> SEQ ID NO 224
<211> LENGTH: 13
<212> TYPE: PRT
<213> ORGANISM: Artificial Sequence
<220> FEATURE:
<223> OTHER INFORMATION: Synthetic

<400> SEQUENCE: 224

Ala Arg Asp Tyr Trp Gly Ser Gly Tyr Tyr Phe Asp Phe
1               5                   10
```

<210> SEQ ID NO 225
<211> LENGTH: 321
<212> TYPE: DNA
<213> ORGANISM: Artificial Sequence
<220> FEATURE:
<223> OTHER INFORMATION: Synthetic

<400> SEQUENCE: 225

```
gacatccaga tgacccagtc tccatcctcc ctgtctgcat ctgtaggaga cagagtcacc      60
atcacttgcc gggcaagtca gaacattaac aactatttaa attggtatca gcagaaacca     120
gggaaagccc ctaaactcct gatctatgct gcatccagtt tccaaaatgc ggtcccatca     180
aggttcagtg gcagtggatc tgggacagat ttcactctca ccatcagcag tctgcaacct     240
gaagattttg caacttacta ctgtcaacag agttacaata ccccgctcac tttcggcggg     300
gggaccaagg tggagatcaa a                                               321
```

<210> SEQ ID NO 226
<211> LENGTH: 107
<212> TYPE: PRT
<213> ORGANISM: Artificial Sequence
<220> FEATURE:
<223> OTHER INFORMATION: Synthetic

<400> SEQUENCE: 226

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asn Ile Asn Asn Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Phe Gln Asn Ala Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asn Thr Pro Leu
                 85                  90                  95

Thr Phe Gly Gly Gly Thr Lys Val Glu Ile Lys
            100                 105
```

<210> SEQ ID NO 227
<211> LENGTH: 18
<212> TYPE: DNA
<213> ORGANISM: Artificial Sequence
<220> FEATURE:
<223> OTHER INFORMATION: Synthetic

<400> SEQUENCE: 227

```
cagaacatta acaactat                                                    18
```

<210> SEQ ID NO 228
<211> LENGTH: 6
<212> TYPE: PRT
<213> ORGANISM: Artificial Sequence
<220> FEATURE:
<223> OTHER INFORMATION: Synthetic

<400> SEQUENCE: 228

```
Gln Asn Ile Asn Asn Tyr
  1               5
```

<210> SEQ ID NO 229
<211> LENGTH: 9
<212> TYPE: DNA
<213> ORGANISM: Artificial Sequence
<220> FEATURE:
<223> OTHER INFORMATION: Synthetic

<400> SEQUENCE: 229 gctgcatcc                                                                 9

<210> SEQ ID NO 230
<211> LENGTH: 3
<212> TYPE: PRT
<213> ORGANISM: Artificial Sequence
<220> FEATURE:
<223> OTHER INFORMATION: Synthetic

<400> SEQUENCE: 230

Ala Ala Ser
 1

<210> SEQ ID NO 231
<211> LENGTH: 27
<212> TYPE: DNA
<213> ORGANISM: Artificial Sequence
<220> FEATURE:
<223> OTHER INFORMATION: Synthetic

<400> SEQUENCE: 231
caacagagtt acaataccec gctcact                                            27

<210> SEQ ID NO 232
<211> LENGTH: 9
<212> TYPE: PRT
<213> ORGANISM: Artificial Sequence
<220> FEATURE:
<223> OTHER INFORMATION: Synthetic

<400> SEQUENCE: 232

Gln Gln Ser Tyr Asn Thr Pro Leu Thr
 1               5

<210> SEQ ID NO 233
<211> LENGTH: 390
<212> TYPE: DNA
<213> ORGANISM: Artificial Sequence
<220> FEATURE:
<223> OTHER INFORMATION: Synthetic

<400> SEQUENCE: 233
gaggtgcagc tggtggagtc tgggggaggc ttggtccagt ctgggggtc cctgagactc         60 tcctgtgcag cctctggatt caccttagt agctattgga tgagctgggt ccgccaggct        120
ccagggaagg ggctggagtg gtggccaac ataaagcaag atggaagtga aaatactat         180 gtggactctg tgaagggccg attcaccatc tccagagaca cgccaagaa ctcactgtat        240 ctgcaaatga acagcctgag agccgatgac acggctgtgt attactgtgc gagagatgat      300
attgtagtag taccagctcc tatgggatat tactactact acttcggtat ggacgtctgg     360
ggccaaggga ccacggtcac cgtctcctca                                       390

<210> SEQ ID NO 234
<211> LENGTH: 130
<212> TYPE: PRT
<213> ORGANISM: Artificial Sequence
<220> FEATURE:
<223> OTHER INFORMATION: Synthetic

<400> SEQUENCE: 234

Glu Val Gln Leu Val Glu Ser Gly Gly Gly Leu Val Gln Ser Gly Gly
1               5                   10                  15
Ser Leu Arg Leu Ser Cys Ala Ala Ser Gly Phe Thr Phe Ser Ser Tyr
            20                  25                  30
Trp Met Ser Trp Val Arg Gln Ala Pro Gly Lys Gly Leu Glu Trp Val
        35                  40                  45
Ala Asn Ile Lys Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Asp Asp Thr Ala Val Tyr Tyr Cys
                85                  90                  95
Ala Arg Asp Asp Ile Val Val Val Pro Ala Pro Met Gly Tyr Tyr Tyr
            100                 105                 110
Tyr Tyr Phe Gly Met Asp Val Trp Gly Gln Gly Thr Thr Val Thr Val
        115                 120                 125
Ser Ser
    130

<210> SEQ ID NO 235
<211> LENGTH: 24
<212> TYPE: DNA
<213> ORGANISM: Artificial Sequence
<220> FEATURE:
<223> OTHER INFORMATION: Synthetic

<400> SEQUENCE: 235
ggattcacct ttagtagcta ttgg                                      24

<210> SEQ ID NO 236
<211> LENGTH: 8
<212> TYPE: PRT
<213> ORGANISM: Artificial Sequence
<220> FEATURE:
<223> OTHER INFORMATION: Synthetic

<400> SEQUENCE: 236

Gly Phe Thr Phe Ser Ser Tyr Trp
1               5

<210> SEQ ID NO 237
<211> LENGTH: 24
<212> TYPE: DNA
<213> ORGANISM: Artificial Sequence
<220> FEATURE:
<223> OTHER INFORMATION: Synthetic

<400> SEQUENCE: 237
ataaagcaag atggaagtga gaaa                                      24

<210> SEQ ID NO 238
<211> LENGTH: 8
<212> TYPE: PRT
<213> ORGANISM: Artificial Sequence
<220> FEATURE:
<223> OTHER INFORMATION: Synthetic

<400> SEQUENCE: 238

Ile Lys Gln Asp Gly Ser Glu Lys
1               5

<210> SEQ ID NO 239
<211> LENGTH: 69
<212> TYPE: DNA
<213> ORGANISM: Artificial Sequence
<220> FEATURE:
<223> OTHER INFORMATION: Synthetic

<400> SEQUENCE: 239

```
gcgagagatg atattgtagt agtaccagct cctatgggat attactacta ctacttcggt    60
atggacgtc                                                            69
```

<210> SEQ ID NO 240
<211> LENGTH: 23
<212> TYPE: PRT
<213> ORGANISM: Artificial Sequence
<220> FEATURE:
<223> OTHER INFORMATION: Synthetic

<400> SEQUENCE: 240

Ala Arg Asp Asp Ile Val Val Val Pro Ala Pro Met Gly Tyr Tyr Tyr
1               5                   10                  15

Tyr Tyr Phe Gly Met Asp Val
            20

<210> SEQ ID NO 241
<211> LENGTH: 321
<212> TYPE: DNA
<213> ORGANISM: Artificial Sequence
<220> FEATURE:
<223> OTHER INFORMATION: Synthetic

<400> SEQUENCE: 241

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtacac ttttggccag   300
gggaccaagc tggagatcaa a                                             321
```

<210> SEQ ID NO 242
<211> LENGTH: 107
<212> TYPE: PRT
<213> ORGANISM: Artificial Sequence
<220> FEATURE:
<223> OTHER INFORMATION: Synthetic

<400> SEQUENCE: 242

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
            85                  90                  95

Thr Phe Gly Gln Gly Thr Lys Leu Glu Ile Lys
            100                 105

<210> SEQ ID NO 243
<211> LENGTH: 18
<212> TYPE: DNA
<213> ORGANISM: Artificial Sequence
<220> FEATURE:
<223> OTHER INFORMATION: Synthetic

<400> SEQUENCE: 243
cagggcatta gaaatgat                                                 18

<210> SEQ ID NO 244
<211> LENGTH: 6
<212> TYPE: PRT
<213> ORGANISM: Artificial Sequence
<220> FEATURE:
<223> OTHER INFORMATION: Synthetic

<400> SEQUENCE: 244

Gln Gly Ile Arg Asn Asp
1               5

<210> SEQ ID NO 245
<211> LENGTH: 9
<212> TYPE: DNA
<213> ORGANISM: Artificial Sequence
<220> FEATURE:
<223> OTHER INFORMATION: Synthetic

<400> SEQUENCE: 245 gctgcatcc                                                            9

<210> SEQ ID NO 246
<211> LENGTH: 3
<212> TYPE: PRT
<213> ORGANISM: Artificial Sequence
<220> FEATURE:
<223> OTHER INFORMATION: Synthetic

<400> SEQUENCE: 246

Ala Ala Ser
1

<210> SEQ ID NO 247
<211> LENGTH: 27
<212> TYPE: DNA
<213> ORGANISM: Artificial Sequence
<220> FEATURE:
<223> OTHER INFORMATION: Synthetic

<400> SEQUENCE: 247
ctacagcata atagttaccc gtacact                                       27

<210> SEQ ID NO 248
<211> LENGTH: 9
<212> TYPE: PRT
<213> ORGANISM: Artificial Sequence
<220> FEATURE:
<223> OTHER INFORMATION: Synthetic

<400> SEQUENCE: 248

Leu Gln His Asn Ser Tyr Pro Tyr Thr
  1               5

<210> SEQ ID NO 249
<211> LENGTH: 369
<212> TYPE: DNA
<213> ORGANISM: Artificial Sequence
<220> FEATURE:
<223> OTHER INFORMATION: Synthetic

<400> SEQUENCE: 249

```
gaagtgcagc tggtggagtc tgggggaggc ttggttcagc ctggcaggtc cctgagactc      60
tcctgtgcag cctctggatt cacctttgat gattttgcca tgcactgggt ccgacaagct     120
ccagggaagg gcctggagtg gtctcaggt attagttgga ctggtggtaa catggactat     180
gcgaactctg tgaagggccg attcaccatc tccagagagg acgccaagaa ttccctgtat     240
ctgcaaatga acagtctgag agctgcggac acggccttgt attactgtgt aaaagatata     300
agggggatag tggctacggg gggggctttt gatatctggg gccgaggcac aatggtcacc     360
gtctcttca                                                              369
```

<210> SEQ ID NO 250
<211> LENGTH: 123
<212> TYPE: PRT
<213> ORGANISM: Artificial Sequence
<220> FEATURE:
<223> OTHER INFORMATION: Synthetic

<400> SEQUENCE: 250

Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Phe
                 20                  25                  30

Ala Met His Trp Val Arg Gln Ala Pro Gly Lys Gly Leu Glu Trp Val
             35                  40                  45

Ser Gly Ile Ser Trp Thr Gly Gly Asn Met Asp Tyr Ala Asn Ser Val
         50                  55                  60

Lys Gly Arg Phe Thr Ile Ser Arg Glu Asp Ala Lys Asn Ser Leu Tyr
 65                  70                  75                  80

Leu Gln Met Asn Ser Leu Arg Ala Ala Asp Thr Ala Leu Tyr Tyr Cys
                 85                  90                  95

Val Lys Asp Ile Arg Gly Ile Val Ala Thr Gly Gly Ala Phe Asp Ile
                100                 105                 110

Trp Gly Arg Gly Thr Met Val Thr Val Ser Ser
            115                 120

<210> SEQ ID NO 251
<211> LENGTH: 24
<212> TYPE: DNA
<213> ORGANISM: Artificial Sequence
<220> FEATURE:
<223> OTHER INFORMATION: Synthetic

<400> SEQUENCE: 251

```
ggattcacct ttgatgattt tgcc                                              24
```

<210> SEQ ID NO 252
<211> LENGTH: 8
<212> TYPE: PRT
<213> ORGANISM: Artificial Sequence
<220> FEATURE:

<223> OTHER INFORMATION: Synthetic

<400> SEQUENCE: 252

Gly Phe Thr Phe Asp Asp Phe Ala
1               5

<210> SEQ ID NO 253
<211> LENGTH: 24
<212> TYPE: DNA
<213> ORGANISM: Artificial Sequence
<220> FEATURE:
<223> OTHER INFORMATION: Synthetic

<400> SEQUENCE: 253
attagttgga ctggtggtaa catg                                          24

<210> SEQ ID NO 254
<211> LENGTH: 8
<212> TYPE: PRT
<213> ORGANISM: Artificial Sequence
<220> FEATURE:
<223> OTHER INFORMATION: Synthetic

<400> SEQUENCE: 254

Ile Ser Trp Thr Gly Gly Asn Met
1               5

<210> SEQ ID NO 255
<211> LENGTH: 48
<212> TYPE: DNA
<213> ORGANISM: Artificial Sequence
<220> FEATURE:
<223> OTHER INFORMATION: Synthetic

<400> SEQUENCE: 255
gtaaaagata taagggggat agtggctacg ggggggctt ttgatatc                 48

<210> SEQ ID NO 256
<211> LENGTH: 16
<212> TYPE: PRT
<213> ORGANISM: Artificial Sequence
<220> FEATURE:
<223> OTHER INFORMATION: Synthetic

<400> SEQUENCE: 256

Val Lys Asp Ile Arg Gly Ile Val Ala Thr Gly Gly Ala Phe Asp Ile
1               5                   10                  15

<210> SEQ ID NO 257
<211> LENGTH: 321
<212> TYPE: DNA
<213> ORGANISM: Artificial Sequence
<220> FEATURE:
<223> OTHER INFORMATION: Synthetic

<400> SEQUENCE: 257
gacatccaga tgacccagtc tccatcctcc ctgtctgcat ctgtaggaga cagagtcacc    60
atctcttgcc gggcaagtca gaccattagc acttatttaa attggtttca gcagaaacca   120
gggaaagccc ctaagctcct gatctatgtt gtgtccagtt tgcaaagtgg ggtcccatca   180
aggttcagtg gcagtggatc tgggacagat ttcactctca ccatcagcag tctgcaacct   240
gaagattttg caacttatta ctgtcaacag agttacagta ccccattcac tttcggccct   300
gggaccaaag tggatatcaa a                                             321

<210> SEQ ID NO 258
<211> LENGTH: 107
<212> TYPE: PRT
<213> ORGANISM: Artificial Sequence
<220> FEATURE:
<223> OTHER INFORMATION: Synthetic

<400> SEQUENCE: 258

Asp Ile Gln Met Thr Gln Ser Pro Ser Leu Ser Ala Ser Val Gly
1               5                   10                  15

Asp Arg Val Thr Ile Ser Cys Arg Ala Ser Gln Thr Ile Ser Thr Tyr
            20                  25                  30

Leu Asn Trp Phe Gln Gln Lys Pro Gly Lys Ala Pro Lys Leu Leu Ile
        35                  40                  45

Tyr Val Val Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 259
<211> LENGTH: 18
<212> TYPE: DNA
<213> ORGANISM: Artificial Sequence
<220> FEATURE:
<223> OTHER INFORMATION: Synthetic

<400> SEQUENCE: 259
cagaccatta gcacttat                                              18

<210> SEQ ID NO 260
<211> LENGTH: 6
<212> TYPE: PRT
<213> ORGANISM: Artificial Sequence
<220> FEATURE:
<223> OTHER INFORMATION: Synthetic

<400> SEQUENCE: 260

Gln Thr Ile Ser Thr Tyr
1               5

<210> SEQ ID NO 261
<211> LENGTH: 9
<212> TYPE: DNA
<213> ORGANISM: Artificial Sequence
<220> FEATURE:
<223> OTHER INFORMATION: Synthetic

<400> SEQUENCE: 261 gttgtgtcc                                                         9

<210> SEQ ID NO 262
<211> LENGTH: 3
<212> TYPE: PRT
<213> ORGANISM: Artificial Sequence
<220> FEATURE:
<223> OTHER INFORMATION: Synthetic

<400> SEQUENCE: 262

Val Val Ser

<210> SEQ ID NO 263
<211> LENGTH: 27
<212> TYPE: DNA
<213> ORGANISM: Artificial Sequence
<220> FEATURE:
<223> OTHER INFORMATION: Synthetic

<400> SEQUENCE: 263
caacagagtt acagtacccc attcact                                    27

<210> SEQ ID NO 264
<211> LENGTH: 9
<212> TYPE: PRT
<213> ORGANISM: Artificial Sequence
<220> FEATURE:
<223> OTHER INFORMATION: Synthetic

<400> SEQUENCE: 264

Gln Gln Ser Tyr Ser Thr Pro Phe Thr
 1               5

<210> SEQ ID NO 265
<211> LENGTH: 345
<212> TYPE: DNA
<213> ORGANISM: Artificial Sequence
<220> FEATURE:
<223> OTHER INFORMATION: Synthetic

<400> SEQUENCE: 265
gaggtgcagc tggtggagtc tggaggaggc ttggtccagc cggggggggtc cctgagactc    60 tcctgtgcag cctctggatt caccgtcggt accaactaca tgaactgggt ccgccaggct   120
ccagggaagg gactggagtg gatctcagtt atttatagcg gtggtagcac attctacgca   180
gactccgtga agggccgatt caccatctcc agacagactt cccagaacac gctgtatctt   240
caaatgaaca gcctgagacc tgaggacacg gccgtatatt actgtgcgag aggtatacgt   300
ggttttgata tctggggcca agggacaatg gtcaccgtct cttca                  345

<210> SEQ ID NO 266
<211> LENGTH: 115
<212> TYPE: PRT
<213> ORGANISM: Artificial Sequence
<220> FEATURE:
<223> OTHER INFORMATION: Synthetic

<400> SEQUENCE: 266

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Gly Thr Asn
                20                  25                  30

Tyr Met Asn Trp Val Arg Gln Ala Pro Gly Lys Gly Leu Glu Trp Ile
            35                  40                  45

Ser Val Ile Tyr Ser Gly Gly Ser Thr Phe Tyr Ala Asp Ser Val Lys
        50                  55                  60

Gly Arg Phe Thr Ile Ser Arg Gln Thr Ser Gln Asn Thr Leu Tyr Leu
65                  70                  75                  80

Gln Met Asn Ser Leu Arg Pro Glu Asp Thr Ala Val Tyr Tyr Cys Ala
                85                  90                  95

Arg Gly Ile Arg Gly Phe Asp Ile Trp Gly Gln Gly Thr Met Val Thr
            100                 105                 110

Val Ser Ser
      115

<210> SEQ ID NO 267
<211> LENGTH: 24
<212> TYPE: DNA
<213> ORGANISM: Artificial Sequence
<220> FEATURE:
<223> OTHER INFORMATION: Synthetic

<400> SEQUENCE: 267
ggattcaccg tcggtaccaa ctac                                         24

<210> SEQ ID NO 268
<211> LENGTH: 8
<212> TYPE: PRT
<213> ORGANISM: Artificial Sequence
<220> FEATURE:
<223> OTHER INFORMATION: Synthetic

<400> SEQUENCE: 268

Gly Phe Thr Val Gly Thr Asn Tyr
1               5

<210> SEQ ID NO 269
<211> LENGTH: 21
<212> TYPE: DNA
<213> ORGANISM: Artificial Sequence
<220> FEATURE:
<223> OTHER INFORMATION: Synthetic

<400> SEQUENCE: 269
atttatagcg gtggtagcac a                                            21

<210> SEQ ID NO 270
<211> LENGTH: 7
<212> TYPE: PRT
<213> ORGANISM: Artificial Sequence
<220> FEATURE:
<223> OTHER INFORMATION: Synthetic

<400> SEQUENCE: 270

Ile Tyr Ser Gly Gly Ser Thr
1               5

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
gcgagaggta tacgtggttt tgatatc                                      27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Ala Arg Gly Ile Arg Gly Phe Asp Ile
1               5

<210> SEQ ID NO 273
<211> LENGTH: 324
<212> TYPE: DNA
<213> ORGANISM: Artificial Sequence
<220> FEATURE:
<223> OTHER INFORMATION: Synthetic

<400> SEQUENCE: 273

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324
```

<210> SEQ ID NO 274
<211> LENGTH: 108
<212> TYPE: PRT
<213> ORGANISM: Artificial Sequence
<220> FEATURE:
<223> OTHER INFORMATION: Synthetic

<400> SEQUENCE: 274

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Pro
                85                  90                  95
Ile Thr Phe Gly Gln Gly Thr Arg Leu Glu Ile Lys
            100                 105
```

<210> SEQ ID NO 275
<211> LENGTH: 18
<212> TYPE: DNA
<213> ORGANISM: Artificial Sequence
<220> FEATURE:
<223> OTHER INFORMATION: Synthetic

<400> SEQUENCE: 275

```
cagagcatta gcagctat                                                  18
```

<210> SEQ ID NO 276
<211> LENGTH: 6
<212> TYPE: PRT
<213> ORGANISM: Artificial Sequence
<220> FEATURE:
<223> OTHER INFORMATION: Synthetic

<400> SEQUENCE: 276

```
Gln Ser Ile Ser Ser Tyr
 1               5
```

```
<210> SEQ ID NO 277
<211> LENGTH: 9
<212> TYPE: DNA
<213> ORGANISM: Artificial Sequence
<220> FEATURE:
<223> OTHER INFORMATION: Synthetic

<400> SEQUENCE: 277 gctgcatcc                                                                  9

<210> SEQ ID NO 278
<211> LENGTH: 3
<212> TYPE: PRT
<213> ORGANISM: Artificial Sequence
<220> FEATURE:
<223> OTHER INFORMATION: Synthetic

<400> SEQUENCE: 278

Ala Ala Ser
 1

<210> SEQ ID NO 279
<211> LENGTH: 30
<212> TYPE: DNA
<213> ORGANISM: Artificial Sequence
<220> FEATURE:
<223> OTHER INFORMATION: Synthetic

<400> SEQUENCE: 279
caacagagtt acagtacccc tccgatcacc                                          30

<210> SEQ ID NO 280
<211> LENGTH: 10
<212> TYPE: PRT
<213> ORGANISM: Artificial Sequence
<220> FEATURE:
<223> OTHER INFORMATION: Synthetic

<400> SEQUENCE: 280

Gln Gln Ser Tyr Ser Thr Pro Pro Ile Thr
 1               5                  10

<210> SEQ ID NO 281
<211> LENGTH: 345
<212> TYPE: DNA
<213> ORGANISM: Artificial Sequence
<220> FEATURE:
<223> OTHER INFORMATION: Synthetic

<400> SEQUENCE: 281
gaggtgcagc tggtggagtc tggaggaggc ttggtccagc cggggggtc cctgagactc          60 tcctgtgcag cctctgggtt taccatcagt accaactaca tgaactgggt ccgccaggct        120
ccagggaagg ggctggagtg ggtcgcagtt atttatagca gtggttccac atactatatc        180
gactccgtga agggccgatt caccatctcc agactcactt ccaagaacac ggtgtatctt        240
caaatgagca gcctgaattc tgaagacacg gccgtgtatt actgtgcgag ggggatcagg        300
ggttttgata tttggggcca aggacaatg gtcaccgtct cttca                         345

<210> SEQ ID NO 282
<211> LENGTH: 115
<212> TYPE: PRT
<213> ORGANISM: Artificial Sequence
<220> FEATURE:
<223> OTHER INFORMATION: Synthetic
```

<400> SEQUENCE: 282

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Ile Ser Thr Asn
            20                  25                  30

Tyr Met Asn Trp Val Arg Gln Ala Pro Gly Lys Gly Leu Glu Trp Val
        35                  40                  45

Ala Val Ile Tyr Ser Ser Gly Ser Thr Tyr Tyr Ile Asp Ser Val Lys
    50                  55                  60

Gly Arg Phe Thr Ile Ser Arg Leu Thr Ser Lys Asn Thr Val Tyr Leu
65              70                  75                  80

Gln Met Ser Ser Leu Asn Ser Glu Asp Thr Ala Val Tyr Tyr Cys Ala
            85                  90                  95

Arg Gly Ile Arg Gly Phe Asp Ile Trp Gly Gln Gly Thr Met Val Thr
        100                 105                 110

Val Ser Ser
        115

<210> SEQ ID NO 283
<211> LENGTH: 24
<212> TYPE: DNA
<213> ORGANISM: Artificial Sequence
<220> FEATURE:
<223> OTHER INFORMATION: Synthetic

<400> SEQUENCE: 283
gggtttacca tcagtaccaa ctac                                      24

<210> SEQ ID NO 284
<211> LENGTH: 8
<212> TYPE: PRT
<213> ORGANISM: Artificial Sequence
<220> FEATURE:
<223> OTHER INFORMATION: Synthetic

<400> SEQUENCE: 284

Gly Phe Thr Ile Ser Thr Asn Tyr
1               5

<210> SEQ ID NO 285
<211> LENGTH: 21
<212> TYPE: DNA
<213> ORGANISM: Artificial Sequence
<220> FEATURE:
<223> OTHER INFORMATION: Synthetic

<400> SEQUENCE: 285
atttatagca gtggttccac a                                         21

<210> SEQ ID NO 286
<211> LENGTH: 7
<212> TYPE: PRT
<213> ORGANISM: Artificial Sequence
<220> FEATURE:
<223> OTHER INFORMATION: Synthetic

<400> SEQUENCE: 286

Ile Tyr Ser Ser Gly Ser Thr
1               5

<210> SEQ ID NO 287
<211> LENGTH: 27

```
<212> TYPE: DNA
<213> ORGANISM: Artificial Sequence
<220> FEATURE:
<223> OTHER INFORMATION: Synthetic

<400> SEQUENCE: 287
gcgaggggga tcagggttt tgatatt                                              27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Ala Arg Gly Ile Arg Gly Phe Asp Ile
 1               5

<210> SEQ ID NO 289
<211> LENGTH: 372
<212> TYPE: DNA
<213> ORGANISM: Artificial Sequence
<220> FEATURE:
<223> OTHER INFORMATION: Synthetic

<400> SEQUENCE: 289
gaagtgcagc tggtggagtc gggggggaggc ttggtacagc ctggcaggtc cctgagactc         60
tcctgtgcag cctctggatt caccattgat gatagtgcca tgcactgggt ccggcaaact        120
ccagggaagg gcctggagtg gtctcaggt attagttgga aaagtggtag cataggttat         180
gcggactctg tgaggggccg attcaccatc tccagagaca cgccaagaa ttccctctat         240 ctgcaaatga acagtctgag agttgaggac acggccttgt attactgtgt aaaagatata        300
aggggcaact ggaactacgg gggaaactgg ttcgaccct ggggccaggg aaccctggtc         360
actgtctcct ca                                                            372

<210> SEQ ID NO 290
<211> LENGTH: 124
<212> TYPE: PRT
<213> ORGANISM: Artificial Sequence
<220> FEATURE:
<223> OTHER INFORMATION: Synthetic

<400> SEQUENCE: 290

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Ile Asp Asp Ser
            20                  25                  30

Ala Met His Trp Val Arg Gln Thr Pro Gly Lys Gly Leu Glu Trp Val
        35                  40                  45

Ser Gly Ile Ser Trp Lys Ser Gly Ser Ile Gly Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Val Lys Asp Ile Arg Gly Asn Trp Asn Tyr Gly Gly Asn Trp Phe Asp
            100                 105                 110

Pro Trp Gly Gln Gly Thr Leu Val Thr Val Ser Ser
        115                 120
```

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacca ttgatgatag tgcc                                      24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Ile Asp Asp Ser Ala
 1               5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attagttgga aaagtggtag cata                                      24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Ser Trp Lys Ser Gly Ser Ile
 1               5

<210> SEQ ID NO 295
<211> LENGTH: 51
<212> TYPE: DNA
<213> ORGANISM: Artificial Sequence
<220> FEATURE:
<223> OTHER INFORMATION: Synthetic

<400> SEQUENCE: 295
gtaaaagata taaggggcaa ctggaactac gggggaaact ggttcgaccc c         51

<210> SEQ ID NO 296
<211> LENGTH: 17
<212> TYPE: PRT
<213> ORGANISM: Artificial Sequence
<220> FEATURE:
<223> OTHER INFORMATION: Synthetic

<400> SEQUENCE: 296

Val Lys Asp Ile Arg Gly Asn Trp Asn Tyr Gly Gly Asn Trp Phe Asp
 1               5                  10                  15

Pro

<210> SEQ ID NO 297
<211> LENGTH: 345
<212> TYPE: DNA
<213> ORGANISM: Artificial Sequence
<220> FEATURE:
<223> OTHER INFORMATION: Synthetic

<400> SEQUENCE: 297

```
gaggtgcagc tggtggagtc tggaggaggc ttggtccagc ctggggggtc cctgagactc    60
tcatgtgaag cctctgggtt caccgtcggt gtcaaccaca tgaactgggt ccgccaggct   120
ccagggaagg gtctggagtg gtctcagtt attttcagta gtggtaggac attctacgga   180
gactacgtga aggggcgatt aaccatcttc agacaaacct cccagaacac ggtgtatctt   240
caaatgaata gcctgagaag tgaggacacg gccatatatt actgtgcgag agggattggc   300
ggtttggaca tctggggccg aggacaatg gtcaccgtct cttca                    345
```

<210> SEQ ID NO 298
<211> LENGTH: 115
<212> TYPE: PRT
<213> ORGANISM: Artificial Sequence
<220> FEATURE:
<223> OTHER INFORMATION: Synthetic

<400> SEQUENCE: 298

```
Glu Val Gln Leu Val Glu Ser Gly Gly Gly Leu Val Gln Pro Gly Gly
 1               5                  10                  15

Ser Leu Arg Leu Ser Cys Glu Ala Ser Gly Phe Thr Val Gly Val Asn
            20                  25                  30

His Met Asn Trp Val Arg Gln Ala Pro Gly Lys Gly Leu Glu Trp Val
        35                  40                  45

Ser Val Ile Phe Ser Ser Gly Arg Thr Phe Tyr Gly Asp Tyr Val Lys
    50                  55                  60

Gly Arg Leu Thr Ile Phe Arg Gln Thr Ser Gln Asn Thr Val Tyr Leu
65                  70                  75                  80

Gln Met Asn Ser Leu Arg Ser Glu Asp Thr Ala Ile Tyr Tyr Cys Ala
                85                  90                  95

Arg Gly Ile Gly Gly Leu Asp Ile Trp Gly Arg Gly Thr Met Val Thr
            100                 105                 110

Val Ser Ser
        115
```

<210> SEQ ID NO 299
<211> LENGTH: 24
<212> TYPE: DNA
<213> ORGANISM: Artificial Sequence
<220> FEATURE:
<223> OTHER INFORMATION: Synthetic

<400> SEQUENCE: 299

```
gggttcaccg tcggtgtcaa ccac                                           24
```

<210> SEQ ID NO 300
<211> LENGTH: 8
<212> TYPE: PRT
<213> ORGANISM: Artificial Sequence
<220> FEATURE:
<223> OTHER INFORMATION: Synthetic

<400> SEQUENCE: 300

```
Gly Phe Thr Val Gly Val Asn His
 1               5
```

<210> SEQ ID NO 301
<211> LENGTH: 21
<212> TYPE: DNA
<213> ORGANISM: Artificial Sequence
<220> FEATURE:
<223> OTHER INFORMATION: Synthetic

<400> SEQUENCE: 301
attttcagta gtggtaggac a                                              21

<210> SEQ ID NO 302
<211> LENGTH: 7
<212> TYPE: PRT
<213> ORGANISM: Artificial Sequence
<220> FEATURE:
<223> OTHER INFORMATION: Synthetic

<400> SEQUENCE: 302

Ile Phe Ser Ser Gly Arg Thr
 1               5

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
gcgagaggga ttggcggttt ggacatc                                        27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Ala Arg Gly Ile Gly Gly Leu Asp Ile
 1               5

<210> SEQ ID NO 305
<211> LENGTH: 369
<212> TYPE: DNA
<213> ORGANISM: Artificial Sequence
<220> FEATURE:
<223> OTHER INFORMATION: Synthetic

<400> SEQUENCE: 305
gaagtgcagc tggtggagtc tgggggaggc ttggttcagc ctggcaggtc cctaagactc    60
tcctgtgcag cctctggatt cacctttgat gattatgcct tgcactgggt ccggcaagct   120
ccagggaagg gcctggagtg gtctcaggt attagttgga ctggtggtac tatagactat    180
gcggactctg tgaagggccg attcaccatc tccagagaca cgccaagaa ctccctgtat    240 ctgcaaatga gcagtctgag aactgaggac acggccatat attactgtac aagagatatc   300
cgggggaact ggaagtacgg aggctggttc gaccccctggg gccagggaac cctggtcacc   360
gtctcctca                                                           369

<210> SEQ ID NO 306
<211> LENGTH: 123
<212> TYPE: PRT

<213> ORGANISM: Artificial Sequence
<220> FEATURE:
<223> OTHER INFORMATION: Synthetic

<400> SEQUENCE: 306

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Ile Ser Trp Thr Gly Gly Thr Ile Asp Tyr Ala Asp Ser Val
    50                  55                  60

Lys Gly Arg Phe Thr Ile Ser Arg Asp Asn Ala Lys Asn Ser Leu Tyr
65              70                  75                  80

Leu Gln Met Ser Ser Leu Arg Thr Glu Asp Thr Ala Ile Tyr Tyr Cys
                85                  90                  95

Thr Arg Asp Ile Arg Gly Asn Trp Lys Tyr Gly Gly Trp Phe Asp Pro
            100                 105                 110

Trp Gly Gln Gly Thr Leu Val Thr Val Ser Ser
        115                 120

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
ggattcacct ttgatgatta tgcc                                      24

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Gly Phe Thr Phe Asp Asp Tyr Ala
1               5

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309
attagttgga ctggtggtac tata                                      24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Ser Trp Thr Gly Gly Thr Ile
1               5

<210> SEQ ID NO 311
<211> LENGTH: 48
<212> TYPE: DNA
<213> ORGANISM: Artificial Sequence
<220> FEATURE:
<223> OTHER INFORMATION: Synthetic

<400> SEQUENCE: 311
acaagagata tccgggggaa ctggaagtac ggaggctggt tcgacccc                48

<210> SEQ ID NO 312
<211> LENGTH: 16
<212> TYPE: PRT
<213> ORGANISM: Artificial Sequence
<220> FEATURE:
<223> OTHER INFORMATION: Synthetic

<400> SEQUENCE: 312

Thr Arg Asp Ile Arg Gly Asn Trp Lys Tyr Gly Gly Trp Phe Asp Pro
 1               5                  10                  15

<210> SEQ ID NO 313
<211> LENGTH: 360
<212> TYPE: DNA
<213> ORGANISM: Artificial Sequence
<220> FEATURE:
<223> OTHER INFORMATION: Synthetic

<400> SEQUENCE: 313
caggtgcagc tggtgcagtc tgggactgag gtgaagaagc ctggggcctc agtgaaggtc     60
tcctgcaagg cttctggata caccttcacc gcctactata tgcactgggt gcgacaggcc    120
cctggtcaag gacttgactg gatgggatgg atcagcccta acagtggttt cacaaactat    180
gcacagaagt tcagggcag ggtcaccatg accagggaca cgtccatcaa cacattttat    240
atggagctga gtggactgag atctgacgac acggccgtat attactgtgc gcgagagggt    300
tctactcacc acaattcttt cgacccctgg ggccagggaa ccctggtcac cgtctcctca    360

<210> SEQ ID NO 314
<211> LENGTH: 120
<212> TYPE: PRT
<213> ORGANISM: Artificial Sequence
<220> FEATURE:
<223> OTHER INFORMATION: Synthetic

<400> SEQUENCE: 314

Gln Val Gln Leu Val Gln Ser Gly Thr Glu Val Lys Lys Pro Gly Ala
 1               5                  10                  15

Ser Val Lys Val Ser Cys Lys Ala Ser Gly Tyr Thr Phe Thr Ala Tyr
                20                  25                  30

Tyr Met His Trp Val Arg Gln Ala Pro Gly Gln Gly Leu Asp Trp Met
            35                  40                  45

Gly Trp Ile Ser Pro Asn Ser Gly Phe Thr Asn Tyr Ala Gln Lys Phe
        50                  55                  60

Gln Gly Arg Val Thr Met Thr Arg Asp Thr Ser Ile Asn Thr Phe Tyr
65                  70                  75                  80

Met Glu Leu Ser Gly Leu Arg Ser Asp Asp Thr Ala Val Tyr Tyr Cys
                85                  90                  95

Ala Arg Glu Gly Ser Thr His His Asn Ser Phe Asp Pro Trp Gly Gln
            100                 105                 110

Gly Thr Leu Val Thr Val Ser Ser
            115                 120

<210> SEQ ID NO 315
<211> LENGTH: 24
<212> TYPE: DNA
<213> ORGANISM: Artificial Sequence
<220> FEATURE:
<223> OTHER INFORMATION: Synthetic

<400> SEQUENCE: 315
ggatacacct tcaccgccta ctat                                            24

<210> SEQ ID NO 316
<211> LENGTH: 8
<212> TYPE: PRT
<213> ORGANISM: Artificial Sequence
<220> FEATURE:
<223> OTHER INFORMATION: Synthetic

<400> SEQUENCE: 316

Gly Tyr Thr Phe Thr Ala Tyr Tyr
1               5

<210> SEQ ID NO 317
<211> LENGTH: 24
<212> TYPE: DNA
<213> ORGANISM: Artificial Sequence
<220> FEATURE:
<223> OTHER INFORMATION: Synthetic

<400> SEQUENCE: 317
atcagcccta acagtggttt caca                                            24

<210> SEQ ID NO 318
<211> LENGTH: 8
<212> TYPE: PRT
<213> ORGANISM: Artificial Sequence
<220> FEATURE:
<223> OTHER INFORMATION: Synthetic

<400> SEQUENCE: 318

Ile Ser Pro Asn Ser Gly Phe Thr
1               5

<210> SEQ ID NO 319
<211> LENGTH: 39
<212> TYPE: DNA
<213> ORGANISM: Artificial Sequence
<220> FEATURE:
<223> OTHER INFORMATION: Synthetic

<400> SEQUENCE: 319
gcgcgagagg gttctactca ccacaattct ttcgacccc                            39

<210> SEQ ID NO 320
<211> LENGTH: 13
<212> TYPE: PRT
<213> ORGANISM: Artificial Sequence
<220> FEATURE:
<223> OTHER INFORMATION: Synthetic

<400> SEQUENCE: 320

Ala Arg Glu Gly Ser Thr His His Asn Ser Phe Asp Pro
1               5                   10

<210> SEQ ID NO 321
<211> LENGTH: 342
<212> TYPE: DNA
<213> ORGANISM: Artificial Sequence
<220> FEATURE:
<223> OTHER INFORMATION: Synthetic

<400> SEQUENCE: 321

```
gaggtgcagc tggtggagtc tggaggaggc ttggtccaac cggggggtc cctgaggctc      60
tcctgtgcag cctctgggtt caccgtcggt actaacttca tgaattgggt ccgccaggct    120
ccagggaagg gctggagtg gtctcagcg atttatagcg gtggtaccgc taactacgca     180
gactccgtga agggccgatt caccatttcc agagacactt ccaggaacac gctgtatctt    240
caaatgaaca gcctgagaac tgaggacacg gccgtttatt attgtgcgag agggggggt    300
atggacgtct ggggccaagg gaccacggtc accgtctcct ca                        342
```

<210> SEQ ID NO 322
<211> LENGTH: 114
<212> TYPE: PRT
<213> ORGANISM: Artificial Sequence
<220> FEATURE:
<223> OTHER INFORMATION: Synthetic

<400> SEQUENCE: 322

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Val Gly Thr Asn
            20                  25                  30
Phe Met Asn Trp Val Arg Gln Ala Pro Gly Lys Gly Leu Glu Trp Val
        35                  40                  45
Ser Ala Ile Tyr Ser Gly Gly Thr Ala Asn Tyr Ala Asp Ser Val Lys
    50                  55                  60
Gly Arg Phe Thr Ile Ser Arg Asp Thr Ser Arg Asn Thr Leu Tyr Leu
65                  70                  75                  80
Gln Met Asn Ser Leu Arg Thr Glu Asp Thr Ala Val Tyr Tyr Cys Ala
                85                  90                  95
Arg Gly Gly Gly Met Asp Val Trp Gly Gln Gly Thr Thr Val Thr Val
            100                 105                 110
Ser Ser
```

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323

```
gggttcaccg tcggtactaa cttc                                            24
```

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

```
Gly Phe Thr Val Gly Thr Asn Phe
1               5
```

<210> SEQ ID NO 325
<211> LENGTH: 21
<212> TYPE: DNA
<213> ORGANISM: Artificial Sequence
<220> FEATURE:
<223> OTHER INFORMATION: Synthetic

<400> SEQUENCE: 325
atttatagcg gtggtaccgc t                                       21

<210> SEQ ID NO 326
<211> LENGTH: 7
<212> TYPE: PRT
<213> ORGANISM: Artificial Sequence
<220> FEATURE:
<223> OTHER INFORMATION: Synthetic

<400> SEQUENCE: 326

Ile Tyr Ser Gly Gly Thr Ala
1               5

<210> SEQ ID NO 327
<211> LENGTH: 24
<212> TYPE: DNA
<213> ORGANISM: Artificial Sequence
<220> FEATURE:
<223> OTHER INFORMATION: Synthetic

<400> SEQUENCE: 327
gcgagagggg ggggtatgga cgtc                                    24

<210> SEQ ID NO 328
<211> LENGTH: 8
<212> TYPE: PRT
<213> ORGANISM: Artificial Sequence
<220> FEATURE:
<223> OTHER INFORMATION: Synthetic

<400> SEQUENCE: 328

Ala Arg Gly Gly Gly Met Asp Val
1               5

<210> SEQ ID NO 329
<211> LENGTH: 354
<212> TYPE: DNA
<213> ORGANISM: Artificial Sequence
<220> FEATURE:
<223> OTHER INFORMATION: Synthetic

<400> SEQUENCE: 329
caggtccagc tggtgcagtc tggggctgag gtgaagaagc ctgggtcctc ggtgaaggtc    60
tcctgcaagg cttctggagg caccttcaac acctatgttc tcagctgggt gcgacaggcc   120
cctggacaag gcttgagtg gatgggagag atcatcccta tcttaggtgc agcaaactac   180
gcacagaact tccagggcag agtcactttt accacggacg aatccacgaa tacagcctac   240
atggacctga gcagcctaag atctgaggac acggccgtgt attactgtgc gagagatcgg   300
acctccgggg ggttcgaccc ctggggccag ggaaccctgg tcactgtctc ctca          354

<210> SEQ ID NO 330
<211> LENGTH: 118
<212> TYPE: PRT
<213> ORGANISM: Artificial Sequence
<220> FEATURE:
<223> OTHER INFORMATION: Synthetic

<400> SEQUENCE: 330

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Asn Thr Tyr
            20                  25                  30

Val Leu Ser Trp Val Arg Gln Ala Pro Gly Gln Gly Leu Glu Trp Met
        35                  40                  45

Gly Glu Ile Ile Pro Ile Leu Gly Ala Ala Asn Tyr Ala Gln Asn Phe
    50                  55                  60

Gln Gly Arg Val Thr Phe Thr Thr Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Arg Thr Ser Gly Gly Phe Asp Pro Trp Gly Gln Gly Thr
            100                 105                 110

Leu Val Thr Val Ser Ser
        115

<210> SEQ ID NO 331
<211> LENGTH: 24
<212> TYPE: DNA
<213> ORGANISM: Artificial Sequence
<220> FEATURE:
<223> OTHER INFORMATION: Synthetic

<400> SEQUENCE: 331
ggaggcacct tcaacaccta tgtt                                    24

<210> SEQ ID NO 332
<211> LENGTH: 8
<212> TYPE: PRT
<213> ORGANISM: Artificial Sequence
<220> FEATURE:
<223> OTHER INFORMATION: Synthetic

<400> SEQUENCE: 332

Gly Gly Thr Phe Asn Thr Tyr Val
1               5

<210> SEQ ID NO 333
<211> LENGTH: 24
<212> TYPE: DNA
<213> ORGANISM: Artificial Sequence
<220> FEATURE:
<223> OTHER INFORMATION: Synthetic

<400> SEQUENCE: 333
atcatcccta tcttaggtgc agca                                    24

<210> SEQ ID NO 334
<211> LENGTH: 8
<212> TYPE: PRT
<213> ORGANISM: Artificial Sequence
<220> FEATURE:
<223> OTHER INFORMATION: Synthetic

<400> SEQUENCE: 334

Ile Ile Pro Ile Leu Gly Ala Ala
1               5

<210> SEQ ID NO 335

```
<211> LENGTH: 33
<212> TYPE: DNA
<213> ORGANISM: Artificial Sequence
<220> FEATURE:
<223> OTHER INFORMATION: Synthetic

<400> SEQUENCE: 335
gcgagagatc ggacctccgg ggggttcgac ccc                             33

<210> SEQ ID NO 336
<211> LENGTH: 11
<212> TYPE: PRT
<213> ORGANISM: Artificial Sequence
<220> FEATURE:
<223> OTHER INFORMATION: Synthetic

<400> SEQUENCE: 336

Ala Arg Asp Arg Thr Ser Gly Gly Phe Asp Pro
 1               5                  10

<210> SEQ ID NO 337
<211> LENGTH: 357
<212> TYPE: DNA
<213> ORGANISM: Artificial Sequence
<220> FEATURE:
<223> OTHER INFORMATION: Synthetic

<400> SEQUENCE: 337
caggttcagc tggtgcagtc tggagctgag gtggagaagc ctggggcctc agtgaaggtc    60
tcctgcaagg cttctggtta catctttacc cactatggta tcagctgggt gcgacaggcc   120
cctggacaag gacttgagtg ggtgggctgg atcagccctt acaatggtta cacagactat   180
gcacagaaac tccagggcag agtcaccttg accacagaca catccacgac cacagcctac   240
atggagctga ggaacctgag atctgacgac acggccatgt attactgttc gagagggagg   300
ggcccttact ggtccttcga tctctggggc cgtggcaccc tggtcaccgt ctcctca      357

<210> SEQ ID NO 338
<211> LENGTH: 119
<212> TYPE: PRT
<213> ORGANISM: Artificial Sequence
<220> FEATURE:
<223> OTHER INFORMATION: Synthetic

<400> SEQUENCE: 338

Gln Val Gln Leu Val Gln Ser Gly Ala Glu Val Glu Lys Pro Gly Ala
 1               5                  10                  15

Ser Val Lys Val Ser Cys Lys Ala Ser Gly Tyr Ile Phe Thr His Tyr
                20                  25                  30

Gly Ile Ser Trp Val Arg Gln Ala Pro Gly Gln Gly Leu Glu Trp Val
            35                  40                  45

Gly Trp Ile Ser Pro Tyr Asn Gly Tyr Thr Asp Tyr Ala Gln Lys Leu
        50                  55                  60

Gln Gly Arg Val Thr Leu Thr Thr Asp Thr Ser Thr Thr Thr Ala Tyr
65                  70                  75                  80

Met Glu Leu Arg Asn Leu Arg Ser Asp Asp Thr Ala Met Tyr Tyr Cys
                85                  90                  95

Ser Arg Gly Arg Gly Pro Tyr Trp Ser Phe Asp Leu Trp Gly Arg Gly
                100                 105                 110

Thr Leu Val Thr Val Ser Ser
            115
```

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggttacatct ttacccacta tggt                                              24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Tyr Ile Phe Thr His Tyr Gly
 1               5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341 atcagcccttt acaatggtta caca                                             24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Ser Pro Tyr Asn Gly Tyr Thr
 1               5

<210> SEQ ID NO 343
<211> LENGTH: 36
<212> TYPE: DNA
<213> ORGANISM: Artificial Sequence
<220> FEATURE:
<223> OTHER INFORMATION: Synthetic

<400> SEQUENCE: 343
tcgagaggga ggggcccttta ctggtccttc gatctc                                36

<210> SEQ ID NO 344
<211> LENGTH: 12
<212> TYPE: PRT
<213> ORGANISM: Artificial Sequence
<220> FEATURE:
<223> OTHER INFORMATION: Synthetic

<400> SEQUENCE: 344

Ser Arg Gly Arg Gly Pro Tyr Trp Ser Phe Asp Leu
 1               5                  10

<210> SEQ ID NO 345
<211> LENGTH: 249
<212> TYPE: PRT

```
<213> ORGANISM: Artificial Sequence
<220> FEATURE:
<223> OTHER INFORMATION: hPD-L1-MMH
<220> FEATURE:
<223> OTHER INFORMATION: 1-221: aa 19-239 of NP_054862.1
<220> FEATURE:
<223> OTHER INFORMATION: 222-249: myc-myc-hexahistidine tag

<400> SEQUENCE: 345
```

Phe Thr Val Thr Val Pro Lys Asp Leu Tyr Val Val Glu Tyr Gly Ser
 1               5                  10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Glu Gln Lys
        210                 215                 220

Leu Ile Ser Glu Glu Asp Leu Gly Gly Glu Gln Lys Leu Ile Ser Glu
225                 230                 235                 240

Glu Asp Leu His His His His His His
                245

```
<210> SEQ ID NO 346
<211> LENGTH: 249
<212> TYPE: PRT
<213> ORGANISM: Artificial Sequence
<220> FEATURE:
<223> OTHER INFORMATION: MfPD-L1-MMH
<220> FEATURE:
<223> OTHER INFORMATION: 1-221:MfPD-L1
<220> FEATURE:
<223> OTHER INFORMATION: 222-249: myc-myc-hexahistidine tag

<400> SEQUENCE: 346
```

Phe Thr Val Thr Val Pro Lys Asp Leu Tyr Val Val Glu Tyr Gly Ser
 1               5                  10                  15

Asn Met Thr Ile Glu Cys Lys Phe Pro Val Glu Lys Gln Leu Asp Leu
            20                  25                  30

Thr Ser Leu Ile Val Tyr Trp Glu Met Glu Asp Lys Asn Ile Ile Gln

-continued

```
                35                  40                  45
Phe Val His Gly Glu Glu Asp Leu Lys Val Gln His Ser Asn Tyr Arg
 50                  55                  60
Gln Arg Ala Gln Leu Leu Lys Asp Gln Leu Ser Leu Gly Asn Ala Ala
 65                  70                  75                  80
Leu Arg Ile Thr Asp Val Lys Leu Gln Asp Ala Gly Val Tyr Arg Cys
                 85                  90                  95
Met Ile Ser Tyr Gly Gly Ala Asp Tyr Lys Arg Ile Thr Val Lys Val
                100                 105                 110
Asn Ala Pro Tyr Asn Lys Ile Asn Gln Arg Ile Leu Val Val Asp Pro
            115                 120                 125
Val Thr Ser Glu His Glu Leu Thr Cys Gln Ala Glu Gly Tyr Pro Lys
130                 135                 140
Ala Glu Val Ile Trp Thr Ser Ser Asp His Gln Val Leu Ser Gly Lys
145                 150                 155                 160
Thr Thr Thr Thr Asn Ser Lys Arg Glu Glu Lys Leu Leu Asn Val Thr
                165                 170                 175
Ser Thr Leu Arg Ile Asn Thr Thr Ala Asn Glu Ile Phe Tyr Cys Ile
            180                 185                 190
Phe Arg Arg Leu Asp Pro Glu Glu Asn His Thr Ala Glu Leu Val Ile
        195                 200                 205
Pro Glu Leu Pro Leu Ala Leu Pro Pro Asn Glu Arg Thr Glu Gln Lys
210                 215                 220
Leu Ile Ser Glu Glu Asp Leu Gly Gly Glu Gln Lys Leu Ile Ser Glu
225                 230                 235                 240
Glu Asp Leu His His His His His His
                245

<210> SEQ ID NO 347
<211> LENGTH: 448
<212> TYPE: PRT
<213> ORGANISM: Artificial Sequence
<220> FEATURE:
<223> OTHER INFORMATION: hPD-L1-hFc
<220> FEATURE:
<223> OTHER INFORMATION: 1-221: aa 19-239 of NP_054862.1
<220> FEATURE:
<223> OTHER INFORMATION: 222-448: aa 104-330 of P01857

<400> SEQUENCE: 347

Phe Thr Val Thr Val Pro Lys Asp Leu Tyr Val Val Glu Tyr Gly Ser
  1               5                  10                  15
Asn Met Thr Ile Glu Cys Lys Phe Pro Val Glu Lys Gln Leu Asp Leu
             20                  25                  30
Ala Ala Leu Ile Val Tyr Trp Glu Met Glu Asp Lys Asn Ile Ile Gln
         35                  40                  45
Phe Val His Gly Glu Glu Asp Leu Lys Val Gln His Ser Ser Tyr Arg
 50                  55                  60
Gln Arg Ala Arg Leu Leu Lys Asp Gln Leu Ser Leu Gly Asn Ala Ala
 65                  70                  75                  80
Leu Gln Ile Thr Asp Val Lys Leu Gln Asp Ala Gly Val Tyr Arg Cys
                 85                  90                  95
Met Ile Ser Tyr Gly Gly Ala Asp Tyr Lys Arg Ile Thr Val Lys Val
                100                 105                 110
Asn Ala Pro Tyr Asn Lys Ile Asn Gln Arg Ile Leu Val Val Asp Pro
            115                 120                 125
```

Val Thr Ser Glu His Glu Leu Thr Cys Gln Ala Glu Gly Tyr Pro Lys
    130                 135                 140

Ala Glu Val Ile Trp Thr Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg Thr Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 348
<211> LENGTH: 454
<212> TYPE: PRT
<213> ORGANISM: Artificial Sequence
<220> FEATURE:
<223> OTHER INFORMATION: hPD-L1-mFc
<220> FEATURE:
<223> OTHER INFORMATION: 1-221: aa 19-239 of NP_054862.1
<220> FEATURE:
<223> OTHER INFORMATION: 222-454: aa 98-330 of P01863

<400> SEQUENCE: 348

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

```
Ala Ala Leu Ile Val Tyr Trp Glu Met Glu Asp Lys Asn Ile Ile Gln
        35                  40                  45
Phe Val His Gly Glu Glu Asp Leu Lys Val Gln His Ser Ser Tyr Arg
    50                  55                  60
Gln Arg Ala Arg Leu Leu Lys Asp Gln Leu Ser Leu Gly Asn Ala Ala
65                  70                  75                  80
Leu Gln Ile Thr Asp Val Lys Leu Gln Asp Ala Gly Val Tyr Arg Cys
                85                  90                  95
Met Ile Ser Tyr Gly Gly Ala Asp Tyr Lys Arg Ile Thr Val Lys Val
            100                 105                 110
Asn Ala Pro Tyr Asn Lys Ile Asn Gln Arg Ile Leu Val Val Asp Pro
        115                 120                 125
Val Thr Ser Glu His Glu Leu Thr Cys Gln Ala Glu Gly Tyr Pro Lys
    130                 135                 140
Ala Glu Val Ile Trp Thr Ser Ser Asp His Gln Val Leu Ser Gly Lys
145                 150                 155                 160
Thr Thr Thr Thr Asn Ser Lys Arg Glu Glu Lys Leu Phe Asn Val Thr
                165                 170                 175
Ser Thr Leu Arg Ile Asn Thr Thr Thr Asn Glu Ile Phe Tyr Cys Thr
            180                 185                 190
Phe Arg Arg Leu Asp Pro Glu Glu Asn His Thr Ala Glu Leu Val Ile
        195                 200                 205
Pro Glu Leu Pro Leu Ala His Pro Pro Asn Glu Arg Thr Glu Pro Arg
    210                 215                 220
Gly Pro Thr Ile Lys Pro Cys Pro Pro Cys Lys Cys Pro Ala Pro Asn
225                 230                 235                 240
Leu Leu Gly Gly Pro Ser Val Phe Ile Phe Pro Pro Lys Ile Lys Asp
                245                 250                 255
Val Leu Met Ile Ser Leu Ser Pro Ile Val Thr Cys Val Val Val Asp
            260                 265                 270
Val Ser Glu Asp Asp Pro Asp Val Gln Ile Ser Trp Phe Val Asn Asn
        275                 280                 285
Val Glu Val His Thr Ala Gln Thr Gln Thr His Arg Glu Asp Tyr Asn
    290                 295                 300
Ser Thr Leu Arg Val Val Ser Ala Leu Pro Ile Gln His Gln Asp Trp
305                 310                 315                 320
Met Ser Gly Lys Glu Phe Lys Cys Lys Val Asn Asn Lys Asp Leu Pro
                325                 330                 335
Ala Pro Ile Glu Arg Thr Ile Ser Lys Pro Lys Gly Ser Val Arg Ala
            340                 345                 350
Pro Gln Val Tyr Val Leu Pro Pro Glu Glu Glu Met Thr Lys Lys
        355                 360                 365
Gln Val Thr Leu Thr Cys Met Val Thr Asp Phe Met Pro Glu Asp Ile
    370                 375                 380
Tyr Val Glu Trp Thr Asn Asn Gly Lys Thr Glu Leu Asn Tyr Lys Asn
385                 390                 395                 400
Thr Glu Pro Val Leu Asp Ser Asp Gly Ser Tyr Phe Met Tyr Ser Lys
                405                 410                 415
Leu Arg Val Glu Lys Lys Asn Trp Val Glu Arg Asn Ser Tyr Ser Cys
            420                 425                 430
Ser Val Val His Glu Gly Leu His Asn His His Thr Thr Lys Ser Phe
        435                 440                 445
```

Ser Arg Thr Pro Gly Lys
        450

<210> SEQ ID NO 349
<211> LENGTH: 379
<212> TYPE: PRT
<213> ORGANISM: Artificial Sequence
<220> FEATURE:
<223> OTHER INFORMATION: hPD-1-mFc
<220> FEATURE:
<223> OTHER INFORMATION: 1-146: aa 25-170 of NP_005009.2 with C93S
<220> FEATURE:
<223> OTHER INFORMATION: 147-379: aa 98-330 of P01863

<400> SEQUENCE: 349

Leu Asp Ser Pro Asp Arg Pro Trp Asn Pro Pro Thr Phe Ser Pro Ala
 1               5                  10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Ser Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Thr
    130                 135                 140

Leu Val Glu Pro Arg Gly Pro Thr Ile Lys Pro Cys Pro Pro Cys Lys
145                 150                 155                 160

Cys Pro Ala Pro Asn Leu Leu Gly Gly Pro Ser Val Phe Ile Phe Pro
                165                 170                 175

Pro Lys Ile Lys Asp Val Leu Met Ile Ser Leu Ser Pro Ile Val Thr
            180                 185                 190

Cys Val Val Val Asp Val Ser Glu Asp Pro Asp Val Gln Ile Ser
        195                 200                 205

Trp Phe Val Asn Asn Val Glu Val His Thr Ala Gln Thr Gln Thr His
    210                 215                 220

Arg Glu Asp Tyr Asn Ser Thr Leu Arg Val Val Ser Ala Leu Pro Ile
225                 230                 235                 240

Gln His Gln Asp Trp Met Ser Gly Lys Glu Phe Lys Cys Lys Val Asn
                245                 250                 255

Asn Lys Asp Leu Pro Ala Pro Ile Glu Arg Thr Ile Ser Lys Pro Lys
            260                 265                 270

Gly Ser Val Arg Ala Pro Gln Val Tyr Val Leu Pro Pro Pro Glu Glu
        275                 280                 285

Glu Met Thr Lys Lys Gln Val Thr Leu Thr Cys Met Val Thr Asp Phe
    290                 295                 300

Met Pro Glu Asp Ile Tyr Val Glu Trp Thr Asn Asn Gly Lys Thr Glu
305                 310                 315                 320

Leu Asn Tyr Lys Asn Thr Glu Pro Val Leu Asp Ser Asp Gly Ser Tyr
                325                 330                 335

```
Phe Met Tyr Ser Lys Leu Arg Val Glu Lys Asn Trp Val Glu Arg
            340                 345                 350

Asn Ser Tyr Ser Cys Ser Val Val His Glu Gly Leu His Asn His His
            355                 360                 365

Thr Thr Lys Ser Phe Ser Arg Thr Pro Gly Lys
            370                 375

<210> SEQ ID NO 350
<211> LENGTH: 373
<212> TYPE: PRT
<213> ORGANISM: Artificial Sequence
<220> FEATURE:
<223> OTHER INFORMATION: hPD-1-hFc
<220> FEATURE:
<223> OTHER INFORMATION: 1-146: aa 25-170 of NP_005009.2 with C93S
<220> FEATURE:
<223> OTHER INFORMATION: 147-373: aa 104-330 of P01857

<400> SEQUENCE: 350

Leu Asp Ser Pro Asp Arg Pro Trp Asn Pro Thr Phe Ser Pro Ala
 1               5                  10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
            35                  40                  45

Ser Asn Gln Thr Asp Lys Leu Ala Ala Phe Pro Glu Asp Arg Ser Gln
 50                  55                  60

Pro Gly Gln Asp Ser Arg Phe Arg Val Thr Gln Leu Pro Asn Gly Arg
65                   70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
            115                 120                 125

Thr Ala His Pro Ser Pro Ser Pro Arg Pro Ala Gly Gln Phe Gln Thr
130                 135                 140

Leu Val Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
            195                 200                 205

Glu Val His Asn Ala Lys Thr Lys Pro Arg Glu Glu Gln Tyr Asn Ser
210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Asp Glu Leu Thr Lys Asn Gln
            275                 280                 285

Val Ser Leu Thr Cys Leu Val Lys Gly Phe Tyr Pro Ser Asp Ile Ala
```

```
            290                 295                 300
Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
                340                 345                 350

Val Met His Glu Ala Leu His Asn His Tyr Thr Gln Lys Ser Leu Ser
                355                 360                 365

Leu Ser Pro Gly Lys
            370

<210> SEQ ID NO 351
<211> LENGTH: 290
<212> TYPE: PRT
<213> ORGANISM: Artificial Sequence
<220> FEATURE:
<223> OTHER INFORMATION: hPD-L1 NP_054862.1

<400> SEQUENCE: 351

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
```

<210> SEQ ID NO 352
<211> LENGTH: 288
<212> TYPE: PRT
<213> ORGANISM: Artificial Sequence
<220> FEATURE:
<223> OTHER INFORMATION: hPD-1 NP_005009.2

<400> SEQUENCE: 352

```
Met Gln Ile Pro Gln Ala Pro Trp Pro Val Val Trp Ala Val Leu Gln
  1               5                  10                  15

Leu Gly Trp Arg Pro Gly Trp Phe Leu Asp Ser Pro Asp Arg Pro Trp
             20                  25                  30

Asn Pro Pro Thr Phe Ser Pro Ala Leu Leu Val Val Thr Glu Gly Asp
         35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 353
<211> LENGTH: 454
<212> TYPE: PRT
<213> ORGANISM: Artificial Sequence
<220> FEATURE:
<223> OTHER INFORMATION: MfPD-L1-mFc
    aa1-221: Mf PD-L1 (aa 19-239 of XP_005581836.1)
    aa222-454: mFc tag (aa 98-330 of P01863)

<400> SEQUENCE: 353

```
Phe Thr Val Thr Val Pro Lys Asp Leu Tyr Val Val Glu Tyr Gly Ser
 1               5                  10                  15
Asn Met Thr Ile Glu Cys Lys Phe Pro Val Glu Lys Gln Leu Asp Leu
            20                  25                  30
Thr Ser Leu Ile Val Tyr Trp Glu Met Glu Asp Lys Asn Ile Ile Gln
        35                  40                  45
Phe Val His Gly Glu Glu Asp Leu Lys Val Gln His Ser Asn Tyr Arg
    50                  55                  60
Gln Arg Ala Gln Leu Leu Lys Asp Gln Leu Ser Leu Gly Asn Ala Ala
65                  70                  75                  80
Leu Arg Ile Thr Asp Val Lys Leu Gln Asp Ala Gly Val Tyr Arg Cys
                85                  90                  95
Met Ile Ser Tyr Gly Gly Ala Asp Tyr Lys Arg Ile Thr Val Lys Val
            100                 105                 110
Asn Ala Pro Tyr Asn Lys Ile Asn Gln Arg Ile Leu Val Val Asp Pro
        115                 120                 125
Val Thr Ser Glu His Glu Leu Thr Cys Gln Ala Glu Gly Tyr Pro Lys
    130                 135                 140
Ala Glu Val Ile Trp Thr Ser Ser Asp His Gln Val Leu Ser Gly Lys
145                 150                 155                 160
Thr Thr Thr Thr Asn Ser Lys Arg Glu Glu Lys Leu Leu Asn Val Thr
                165                 170                 175
Ser Thr Leu Arg Ile Asn Thr Thr Ala Asn Glu Ile Phe Tyr Cys Ile
            180                 185                 190
Phe Arg Arg Leu Asp Pro Glu Glu Asn His Thr Ala Glu Leu Val Ile
        195                 200                 205
Pro Glu Leu Pro Leu Ala Leu Pro Pro Asn Glu Arg Thr Glu Pro Arg
    210                 215                 220
Gly Pro Thr Ile Lys Pro Cys Pro Pro Cys Lys Cys Pro Ala Pro Asn
225                 230                 235                 240
Leu Leu Gly Gly Pro Ser Val Phe Ile Phe Pro Pro Lys Ile Lys Asp
                245                 250                 255
Val Leu Met Ile Ser Leu Ser Pro Ile Val Thr Cys Val Val Val Asp
            260                 265                 270
Val Ser Glu Asp Asp Pro Asp Val Gln Ile Ser Trp Phe Val Asn Asn
        275                 280                 285
Val Glu Val His Thr Ala Gln Thr Gln Thr His Arg Glu Asp Tyr Asn
    290                 295                 300
Ser Thr Leu Arg Val Val Ser Ala Leu Pro Ile Gln His Gln Asp Trp
305                 310                 315                 320
Met Ser Gly Lys Glu Phe Lys Cys Lys Val Asn Asn Lys Asp Leu Pro
                325                 330                 335
Ala Pro Ile Glu Arg Thr Ile Ser Lys Pro Lys Gly Ser Val Arg Ala
            340                 345                 350
Pro Gln Val Tyr Val Leu Pro Pro Pro Glu Glu Glu Met Thr Lys Lys
        355                 360                 365
Gln Val Thr Leu Thr Cys Met Val Thr Asp Phe Met Pro Glu Asp Ile
    370                 375                 380
Tyr Val Glu Trp Thr Asn Asn Gly Lys Thr Glu Leu Asn Tyr Lys Asn
385                 390                 395                 400
Thr Glu Pro Val Leu Asp Ser Asp Gly Ser Tyr Phe Met Tyr Ser Lys
                405                 410                 415
```

-continued

```
Leu Arg Val Glu Lys Lys Asn Trp Val Glu Arg Asn Ser Tyr Ser Cys
        420             425             430

Ser Val Val His Glu Gly Leu His Asn His His Thr Thr Lys Ser Phe
        435             440             445

Ser Arg Thr Pro Gly Lys
    450
```